(12) United States Patent
Nikolay et al.

(10) Patent No.: US 9,708,602 B2
(45) Date of Patent: Jul. 18, 2017

(54) SCREENING FOR INHIBITORS OF RIBOSOME BIOGENESIS

(71) Applicant: Universität Konstanz, Constance (DE)

(72) Inventors: Rainer Nikolay, Constance (DE); Elke Deuerling, Constance (DE)

(73) Assignee: UNIVERSITAET KONSTANZ, Konstanz (DE)

( * ) Notice: Subject to any disclaimer, the term of this patent is extended or adjusted under 35 U.S.C. 154(b) by 0 days.

(21) Appl. No.: 14/894,262

(22) PCT Filed: Jul. 9, 2014

(86) PCT No.: PCT/EP2014/064720
§ 371 (c)(1),
(2) Date: Nov. 25, 2015

(87) PCT Pub. No.: WO2015/004187
PCT Pub. Date: Jan. 15, 2015

(65) Prior Publication Data
US 2016/0122749 A1 May 5, 2016

(30) Foreign Application Priority Data
Jul. 9, 2013 (EP) ..................... 13175775

(51) Int. Cl.
| | | |
|---|---|---|
| *A61K 38/00* | (2006.01) | |
| *C12Q 1/18* | (2006.01) | |
| *C12N 15/62* | (2006.01) | |
| *C12N 15/10* | (2006.01) | |
| *C07K 14/195* | (2006.01) | |
| *G01N 33/542* | (2006.01) | |
| *C07K 14/435* | (2006.01) | |

(52) U.S. Cl.
CPC ........ *C12N 15/1041* (2013.01); *C07K 14/195* (2013.01); *C07K 14/43595* (2013.01); *C12Q 1/18* (2013.01); *G01N 33/542* (2013.01); *C07K 2319/60* (2013.01)

(58) Field of Classification Search
CPC .... A61K 38/00; C07K 14/195; C12N 15/041; C12N 15/62
See application file for complete search history.

(56) References Cited

FOREIGN PATENT DOCUMENTS

| WO | 0032619 A1 | 6/2000 |
|---|---|---|
| WO | 2009047760 A2 | 4/2009 |

OTHER PUBLICATIONS

Akrap, et al., "Forster distances for FRET between mCherry and other visible fluorescent proteins", Anal Biochem 402 (1), 105-106 (2010).
Datsenko, et al., "One-step inactivation of chromosomal genes in *Escherichia coli* K-12 using PCR products", PNAS vol. 97 (12), 6640-6645 (2000).
Hurt, et al., "A Novel in vivo assay reveals inhibition of ribosomal nuclear export in ran-cycle and nucleoporin mutants", Journal of Cell Biology vol. 144 (3), 389-401 (1999).
Jiang, et al., "Identification of novel *Escherichia coli* ribosome-associated proteins using isobaric tags and multidimensional protein identification techniques", Journal of Bacteriology, vol. 189 (9), 3434-3444 (2007).
Klostermeier, et al., "A three-fluorophore FRET assay for high-throughput screening of small-molecule inhibitors of ribosome assembly", Nucleic Acids Research vol. 32 (9), 2707-2715 (2004).
Llano-Sotelo, et al., "Fluorescently labeled ribosomes as a tool for analyzing antibiotic binding", RNA 15, 1597-1604 (2009).
Maguire, et al., "Inhibition of Bacterial Ribosome Assembly: a Suitable Drug Target?", Microbiology and Molecular Biology Reviews vol. 73 (1), 22-35 (2009).
Nikolay, et al., "Validation of a fluorescence-based screening concept to identify rebosome assembly defects in *Escherichia coli*", Nucleic Acids Research vol. 42 (12), e100, 12 pages (2014).
Patent Cooperation Treaty, International Searching Authority, Search Report for PCT/EP2014/064720, 3 pages, Oct. 29, 2014.
Shajani, et al., "Assembly of Bacterial Ribosomes", Annu. Rev. Biochem. 80, 501-526 (2011).
Stoter, et al., "CellProfiler and KNIME: Open Source Tools for High Content Screening", Target Identification and Validation in Drug Discovery: Methods and Protocols, Methods in Molecular Biology, vol. 986, 105-122 (2013).

*Primary Examiner* — Karen Cochrane Carlson
(74) *Attorney, Agent, or Firm* — Viksnins Harris & Padys PLLP

(57) ABSTRACT

The invention relates to a method and a prokaryotic cell for identifying a compound, which interferes with ribosome biogenesis, assembly and/or degradation. The cell expresses a first fusion protein comprising a first ribosomal protein, an amino acid linker and a first fluorescent protein, and a second fusion protein comprising a second ribosomal protein, an amino acid linker and a second fluorescent protein. The invention further relates to a gene construct comprising a first element encoding a first ribosomal protein fused to a first fluorescent protein by an amino acid linker, and a second element encoding a second ribosomal protein fused to a second fluorescent protein by an amino acid linker.

15 Claims, 18 Drawing Sheets

A

B

C

A

B

A

B

A

B

A

B

SEQUENCE LISTING

```
<160> NUMBER OF SEQ ID NOS: 29

<210> SEQ ID NO 1
<211> LENGTH: 7
<212> TYPE: PRT
<213> ORGANISM: Artificial Sequence
<220> FEATURE:
<223> OTHER INFORMATION: peptide sequence

<400> SEQUENCE: 1

Gly Thr Ser Gly Gly Ser Gly
1               5

<210> SEQ ID NO 2
<211> LENGTH: 8
<212> TYPE: PRT
<213> ORGANISM: Artificial Sequence
<220> FEATURE:
<223> OTHER INFORMATION: peptide sequence

<400> SEQUENCE: 2

Gly Ser Gly Ser Gly Ser Gly Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Tev protease cleavage site

<400> SEQUENCE: 3

Glu Asn Leu Tyr Phe Gln Gly
1               5

<210> SEQ ID NO 4
<211> LENGTH: 7
<212> TYPE: PRT
<213> ORGANISM: Artificial Sequence
```

```
<220> FEATURE:
<223> OTHER INFORMATION: Tev protease cleavage site

<400> SEQUENCE: 4

Glu Asn Leu Tyr Phe Gln Ser
1               5

<210> SEQ ID NO 5
<211> LENGTH: 65
<212> TYPE: DNA
<213> ORGANISM: Artificial Sequence
<220> FEATURE:
<221> NAME/KEY: source
<222> LOCATION: 1..65
<223> OTHER INFORMATION: /organism="Artificial Sequence"
      /note="primer"
      /mol_type="unassigned DNA"

<400> SEQUENCE: 5
gagcgtactg gtaaggctgc tcgtatcaaa gagcgtctta acggatccgg ttctggctct    60
ggtgg                                                                65

<210> SEQ ID NO 6
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /organism="Artificial Sequence"
      /note="primer"
      /mol_type="unassigned DNA"

<400> SEQUENCE: 6
ttggccagcc cttcttaaca ggatgtcgct taagcgaaat cgtgtaggct ggagctgctt    60
c                                                                    61

<210> SEQ ID NO 7
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /organism="Artificial Sequence"
      /note="primer"
      /mol_type="unassigned DNA"

<400> SEQUENCE: 7
gtcataaggc taacctgact gcacagatca acaaactggc tgggacgtcg ggtggaagc    59

<210> SEQ ID NO 8
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /organism="Artificial Sequence"
      /note="primer"
      /mol_type="unassigned DNA"

<400> SEQUENCE: 8
gcttgcgcgg gcttttcac aaagcttcag caaattggcg aatgaatatc ctccttagtt    60
c                                                                    61
```

-continued

```
<210> SEQ ID NO 9
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /organism="Artificial Sequence"
      /note="primer"
      /mol_type="unassigned DNA"

<400> SEQUENCE: 9
tctggcttcc caggcggaag aaagcttcgt agaagctgag gggacgtcgg gtggaagc        58

<210> SEQ ID NO 10
<211> LENGTH: 60
<212> TYPE: DNA
<213> ORGANISM: Artificial Sequence
<220> FEATURE:
<221> NAME/KEY: source
<222> LOCATION: 1..60
<223> OTHER INFORMATION: /organism="Artificial Sequence"
      /note="primer"
      /mol_type="unassigned DNA"

<400> SEQUENCE: 10
tctgcaactc gaactatttt ggggagtta tcaagcctta atgaatatcc tccttagttc        60

<210> SEQ ID NO 11
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /organism="Artificial Sequence"
      /note="primer"
      /mol_type="unassigned DNA"

<400> SEQUENCE: 11
tgaccgcttc aacaagcgtt tcaacatccc gggcagcaaa gggacgtcgg gtggaagc        58

<210> SEQ ID NO 12
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /organism="Artificial Sequence"
      /note="primer"
      /mol_type="unassigned DNA"

<400> SEQUENCE: 12
aaaaaagcgc cgtgcggcgc ttttttcgga atccggtca tgaatatcct ccttagttc        59

<210> SEQ ID NO 13
<211> LENGTH: 1086
<212> TYPE: DNA
<213> ORGANISM: Artificial Sequence
<220> FEATURE:
<221> NAME/KEY: source
<222> LOCATION: 1..1086
<223> OTHER INFORMATION: /organism="Artificial Sequence"
      /note="fusion construct"
      /mol_type="unassigned DNA"

<400> SEQUENCE: 13
atgagcaaca ttattaagca acttgaacaa gagcagatga agcaggacgt accttccttc        60
```

```
cgtccgggtg ataccgtgga agtgaaagta tgggttgttg aaggttccaa aaaacgtctg      120
caggcattcg agggcgtggt tatcgctatt cgtaaccgcg gtctgcactc tgcattcact      180
gttcgtaaaa tttccaacgg cgaaggcgtt gagcgtgtct tccagactca ctctccggta      240
gttgacagca tttctgtcaa acgtcgtggt gctgttcgta aagctaaaact gtactacctg     300 cgtgagcgta ctggtaaggc tgctcgtatc aaagagcgtc ttaacgggac gtcgggtgga      360
agcggtatgg tgagcaaggg cgaggagctg ttcaccgggg tggtgcccat cctggtcgag      420
ctggacggcg acgtaaacgg ccacaagttc agcgtgtccg gcgagggcga gggcgatgcc      480
acctacggca agctgaccct gaagttcatc tgcaccaccg gcaagctgcc cgtgccctgg      540
cccaccctcg tgaccaccct gacctacggc gtgcagtgct tcagccgcta ccccgaccac      600
atgaagcagc acgacttctt caagtccgcc atgcccgaag gctacgtcca ggagcgcacc      660
atcttcttca aggacgacgg caactacaag acccgcgccg aggtgaagtt cgagggcgac      720
accctggtga accgcatcga gctgaagggc atcgacttca aggaggacgg caacatcctg      780
gggcacaagc tggagtacaa ctacaacagc cacaacgtct atatcatggc cgacaagcag      840
aagaacggca tcaaggtgaa cttcaagatc cgccacaaca tcgaggacgg cagcgtgcag      900
ctcgccgacc actaccagca gaacacccc atcggcgacg gccccgtgct gctgcccgac       960
aaccactacc tgagcaccca gtccgccctg agcaaagacc ccaacgagaa gcgcgatcac     1020
atggtcctgc tggagttcgt gaccgccgcc gggatcactc tcggcatgga cgagctgtac     1080
aagtaa                                                                 1086

<210> SEQ ID NO 14
<211> LENGTH: 993
<212> TYPE: DNA
<213> ORGANISM: Artificial Sequence
<220> FEATURE:
<221> NAME/KEY: source
<222> LOCATION: 1..993
<223> OTHER INFORMATION: /organism="Artificial Sequence"
      /note="fusion construct"
      /mol_type="unassigned DNA"

<400> SEQUENCE: 14
ttggctaata tcaaatcagc taagaagcgc gccattcagt ctgaaaaggc tcgtaagcac       60
aacgcaagcc gtcgctctat gatgcgtact ttcatcaaga agtatacgc agctatcgaa       120 gctggcgaca aagctgctgc acagaaagca tttaacgaaa tgcaaccgat cgtggaccgt      180
caggctgcta aaggtctgat ccacaaaaac aaagctgcac gtcataaggc taacctgact      240
gcacagatca acaaactggc tgggacgtcg ggtggaagcg gtatggtgag caagggcgag      300
gaggataaca tggccatcat caaggagttc atgcgcttca aggtgcacat ggagggctcc      360
gtgaacggcc acgagttcga gatcgagggc gagggcgagg ccgccccta cgagggcacc      420 cagaccgcca gctgaaggt gaccaagggt ggccccctgc ccttcgcctg ggacatcctg      480
tcccctcagt tcatgtacgg ctccaaggcc tacgtgaagc accccgccga catccccgac      540
tacttgaagc tgtccttccc cgagggcttc aagtgggagc gcgtgatgaa cttcgaggac      600
ggcggcgtgg tgaccgtgac ccaggactcc tccctgcagg acggcgagtt catctacaag      660
gtgaagctgc gcggcaccaa cttcccctcc gacggccccg taatgcagaa gaagaccatg      720
ggctgggagg cctcctccga gcggatgtac cccgaggacg gcgccctgaa gggcgagatc      780
aagcagaggc tgaagctgaa ggacggcggc cactacgacg ctgaggtcaa gaccacctac      840
aaggccaaga agcccgtgca gctgcccggc gcctacaacg tcaacatcaa gttggacatc      900
```

```
acctcccaca acgaggacta caccatcgtg aacagtacg aacgcgccga gggccgccac    960
tccaccggcg gcatggacga gctgtacaag taa                                993

<210> SEQ ID NO 15
<211> LENGTH: 1455
<212> TYPE: DNA
<213> ORGANISM: Artificial Sequence
<220> FEATURE:
<221> NAME/KEY: source
<222> LOCATION: 1..1455
<223> OTHER INFORMATION: /organism="Artificial Sequence"
      /note="fusion construct"
      /mol_type="unassigned DNA"

<400> SEQUENCE: 15
atggcaactg tttccatgcg cgacatgctc aaggctggtg ttcacttcgg tcaccagacc     60
cgttactgga acccgaaaat gaagccgttc atcttcggtg cgcgtaacaa agttcacatc    120
atcaaccttg agaaaactgt accgatgttc aacgaagctc tggctgaact gaacaagatt    180
gcttctcgca aggtaaaat cctttttcgtt ggtactaaac gcgctgcaag cgaagcggtg     240
aaagacgctg ctctgagctg cgaccagttc ttcgtgaacc atcgctggct gggcggtatg    300
ctgactaact ggaaaaccgt tcgtcagtcc atcaaacgtc tgaaagacct ggaaactcag    360
tctcaggacg gtactttcga caagctgacc aagaaagaag cgctgatgcg cactcgtgag    420
ctggagaaac tggaaaacag cctgggcggt atcaagaca tgggcggtct gccggacgct    480
ctgtttgtaa tcgatgctga ccacgaacac attgctatca agaagcaaa caacctgggt    540 attccggtat ttgctatcgt tgataccaac tctgatccgg acggtgttga cttcgttatc    600
ccgggtaacg acgacgcaat ccgtgctgtg accctgtacc tggcgctgt tgctgcaacc    660 gtacgtgaag gccgttctca ggatctggct tcccaggcgg aagaaagctt cgtagaagct    720
gaggggacgt cgggtggaag cggtatggtg agcaagggcg aggaggataa catggccatc    780
atcaaggagt tcatgcgctt caaggtgcac atggagggct ccgtgaacgg ccacgagttc    840
gagatcgagg gcgagggcga gggccgcccc tacgagggca cccagaccgc caagctgaag    900
gtgaccaagg gtggcccct gcccttcgcc tgggacatcc tgtcccctca gttcatgtac    960
ggctccaagg cctacgtgaa gcaccccgcc gacatccccg actacttgaa gctgtccttc   1020
cccgagggct tcaagtggga gcgcgtgatg aacttcgagg acggcggcgt ggtgaccgtg   1080
acccaggact cctccctgca ggacggcgag ttcatctaca aggtgaagct gcgcggcacc   1140
aacttccccc ccgacggccc cgtaatgcag aagaagacca tgggctggga ggcctcctcc   1200
gagcggatgt accccgagga cggcgccctg aagggcgaga tcaagcagag gctgaagctg   1260
aaggacggcg gccactacga cgctgaggtc aagaccacct acaaggccaa gaagcccgtg   1320
cagctgcccg gcgcctacaa cgtcaacatc aagttggaca tcacctccca caacgaggac   1380
tacaccatcg tggaacagta cgaacgcgcc gagggccgcc actccaccgg cggcatggac   1440
gagctgtaca agtaa                                                    1455

<210> SEQ ID NO 16
<211> LENGTH: 951
<212> TYPE: DNA
<213> ORGANISM: Artificial Sequence
<220> FEATURE:
<221> NAME/KEY: source
<222> LOCATION: 1..951
<223> OTHER INFORMATION: /organism="Artificial Sequence"
      /note="fusion construct"
```

/mol_type="unassigned DNA"

<400> SEQUENCE: 16

```
atgaaaaaag atattcaccc gaaatacgaa gaaattactg ctagctgctc ttgcggtaac      60
gtaatgaaaa tccgctccac cgttggtcat gacctgaacc tcgacgtgtg cagcaagtgc     120
cacccgttct tcactggcaa acagcgtgat gttgctaccg gtggccgtgt tgaccgcttc     180
aacaagcgtt tcaacatccc gggcagcaaa gggacgtcgg gtggaagcgg tatggtgagc     240
aagggcgagg agctgttcac cggggtggtg cccatcctgg tcgagctgga cggcgacgta     300
aacggccaca gttcagcgt gtccggcgag ggcgagggcg atgccaccta cggcaagctg      360
accctgaagt tcatctgcac caccggcaag ctgcccgtgc cctggcccac cctcgtgacc     420
accctgacct acggcgtgca gtgcttcagc cgctaccccg accacatgaa gcagcacgac     480
ttcttcaagt ccgccatgcc cgaaggctac gtccaggagc gcaccatctt cttcaaggac     540
gacggcaact acaagacccg cgccgaggtg aagttcgagg gcgacaccct ggtgaaccgc     600
atcgagctga agggcatcga cttcaaggag gacggcaaca tcctggggca caagctggag     660
tacaactaca acagccacaa cgtctatatc atggccgaca gcagaagaa cggcatcaag      720
gtgaacttca agatccgcca caacatcgag gacggcagcg tgcagctcgc cgaccactac     780
cagcagaaca ccccccatcgg cgacggcccc gtgctgctgc ccgacaacca ctacctgagc    840
acccagtccg ccctgagcaa agaccccaac gagaagcgcg atcacatggt cctgctggag     900
ttcgtgaccg ccgccgggat cactctcggc atggacgagc tgtacaagta a              951
```

<210> SEQ ID NO 17
<211> LENGTH: 4988
<212> TYPE: DNA
<213> ORGANISM: Artificial Sequence
<220> FEATURE:
<221> NAME/KEY: source
<222> LOCATION: 1..4988
<223> OTHER INFORMATION: /organism="Artificial Sequence"
      /note="vector construct"
      /mol_type="unassigned DNA"

<400> SEQUENCE: 17

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctacctgac gctttttatc gcaactctct actgtttctc catacccgtt tttttgggct     480
agaaataatt ttgtttaact ttaagaagga gatatacccca tggctaatgc atgcaatggg     540
acgtcgggtg gaagcggtat ggtgagcaag ggcgaggagc tgttcaccgg ggtggtgccc     600
atcctggtcg agctggacgg cgacgtaaac ggccacaagt tcagcgtgtc cggcgagggc     660
gagggcgatg ccacctacgg caagctgacc ctgaagttca tctgcaccac cggcaagctg     720
cccgtgccct ggcccaccct cgtgaccacc ctgacctacg gcgtgcagtg cttcagccgc     780
taccccgacc acatgaagca gcacgacttc ttcaagtccg ccatgcccga aggctacgtc     840
caggagcgca ccatcttctt caaggacgac ggcaactaca agacccgcgc cgaggtgaag     900
```

```
ttcgagggcg acaccctggt gaaccgcatc gagctgaagg gcatcgactt caaggaggac      960
ggcaacatcc tggggcacaa gctggagtac aactacaaca gccacaacgt ctatatcatg     1020
gccgacaagc agaagaacgg catcaaggtg aacttcaaga tccgccacaa catcgaggac     1080
ggcagcgtgc agctcgccga ccactaccag cagaacaccc ccatcggcga cggccccgtg     1140
ctgctgcccg acaaccacta cctgagcacc cagtccgccc tgagcaaaga ccccaacgag     1200
aagcgcgatc acatggtcct gctggagttc gtgaccgccg ccgggatcac tctcggcatg     1260
gacgagctgt acaagtaagt gtaggctgga gctgcttcga agttcctata ctttctagag     1320
aataggaact tcggaatagg aacttcaaga tcccctcacg ctgccgcaag cactcagggc     1380
gcaagggctg ctaaaggaag cggaacacgt agaaagccag tccgcagaaa cggtgctgac     1440
cccggatgaa tgtcagctac tgggctatct ggacaaggga aaacgcaagc gcaaagagaa     1500
agcaggtagc ttgcagtggg cttacatggc gatagctaga ctgggcggtt ttatggacag     1560
caagcgaacc ggaattgcca gctggggcgc cctctggtaa ggttgggaag ccctgcaaag     1620
taaactggat ggctttcttg ccgccaagga tctgatggcg caggggatca agatctgatc     1680
aagagacagg atgaggatcg tttcgcatga ttgaacaaga tggattgcac gcaggttctc     1740
cggccgcttg ggtggagagg ctattcggct atgactgggc acaacagaca atcggctgct     1800
ctgatgccgc cgtgttccgg ctgtcagcgc agggcgcccc ggttcttttt gtcaagaccg     1860
acctgtccgg tgccctgaat gaactgcagg acgaggcagc gcggctatcg tggctggcca     1920
cgacgggcgt tccttgcgca gctgtgctcg acgttgtcac tgaagcggga agggactggc     1980
tgctattggg cgaagtgccg gggcaggatc tcctgtcatc tcaccttgct cctgccgaga     2040
aagtatccat catggctgat gcaatgcggc ggctgcatac gcttgatccg gctacctgcc     2100
cattcgacca ccaagcgaaa catcgcatcg agcgagcacg tactcggatg aagccggtc     2160
ttgtcgatca ggatgatctg gacgaagagc atcaggggct cgcgccagcc gaactgttcg     2220
ccaggctcaa ggcgcgcatg cccgacggcg aggatctcgt cgtgacccat ggcgatgcct     2280
gcttgccgaa tatcatggtg gaaaatggcc gcttttctgg attcatcgac tgtggccggc     2340
tgggtgtggc ggaccgctat caggacatag cgttggctac ccgtgatatt gctgaagagc     2400
ttggcggcga atgggctgac cgcttcctcg tgctttacgg tatcgccgct cccgattcgc     2460
agcgcatcgc cttctatcgc cttcttgacg agttcttctg agcgggactc tggggttcga     2520
aatgaccgac caagcgacgc ccaacctgcc atcacgagat ttcgattcca ccgccgcctt     2580
ctatgaaagg ttgggcttcg gaatcgtttt ccgggacgcc ggctggatga tcctccagcg     2640
cggggatctc atgctggagt tcttcgccca ccccagcttc aaaagcgctc tgaagttcct     2700
atactttcta gagaatagga acttcggaat aggaactaag gaggatattc ataagcttgg     2760
cgtaatcatg gtcatagctg tttcctgtgt gaaattgtta tccgctcaca attccacaca     2820
acatacgagc cggaagcata aagtgtaaag cctggggtgc ctaatgagtg agctaactca     2880
cattaattgc gttgcgctca ctgcccgctt tccagtcggg aaacctgtcg tgccagctgc     2940
attaatgaat cggccaacgc gcggggagag gcggtttgcg tattgggcgc tcttccgctt     3000
cctcgctcac tgactcgctg cgctcggtcg ttcggctgcg gcgagcggta tcagctcact     3060
caaaggcggt aatacggtta tccacagaat caggggataa cgcaggaaag aacatgtgag     3120
caaaaggcca gcaaaggcca ggaaccgta aaaaggccgc gttgctggcg ttttccata      3180
ggctccgccc ccctgacgag catcacaaaa atcgacgctc aagtcagagg tggcgaaacc     3240
```

| | |
|---|---|
| cgacaggact ataaagatac caggcgtttc cccctggaag ctccctcgtg cgctctcctg | 3300 |
| ttccgaccct gccgcttacc ggatacctgt ccgcctttct cccttcggga agcgtggcgc | 3360 |
| tttctcatag ctcacgctgt aggtatctca gttcggtgta ggtcgttcgc tccaagctgg | 3420 |
| gctgtgtgca cgaacccccc gttcagcccg accgctgcgc cttatccggt aactatcgtc | 3480 |
| ttgagtccaa cccggtaaga cacgacttat cgccactggc agcagccact ggtaacagga | 3540 |
| ttagcagagc gaggtatgta ggcggtgcta cagagttctt gaagtggtgg cctaactacg | 3600 |
| gctacactag aagaacagta tttggtatct gcgctctgct gaagccagtt accttcggaa | 3660 |
| aaagagttgg tagctcttga tccggcaaac aaaccaccgc tggtagcggt ggttttttg | 3720 |
| tttgcaagca gcagattacg cgcagaaaaa aaggatctca agaagatcct ttgatctttt | 3780 |
| ctacggggtc tgacgctcag tggaacgaaa actcacgtta agggattttg gtcatgagat | 3840 |
| tatcaaaaag gatcttcacc tagatccttt taaattaaaa atgaagtttt aaatcaatct | 3900 |
| aaagtatata tgagtaaact tggtctgaca gttaccaatg cttaatcagt gaggcaccta | 3960 |
| tctcagcgat ctgtctattt cgttcatcca tagttgcctg actccccgtc gtgtagataa | 4020 |
| ctacgatacg ggagggctta ccatctggcc ccagtgctgc aatgataccg cgagacccac | 4080 |
| gctcaccggc tccagattta tcagcaataa accagccagc cggaagggcc gagcgcagaa | 4140 |
| gtggtcctgc aactttatcc gcctccatcc agtctattaa ttgttgccgg gaagctagag | 4200 |
| taagtagttc gccagttaat agtttgcgca acgttgttgc cattgctaca ggcatcgtgg | 4260 |
| tgtcacgctc gtcgtttggt atggcttcat tcagctccgg ttcccaacga tcaaggcgag | 4320 |
| ttacatgatc ccccatgttg tgcaaaaaag cggttagctc cttcggtcct ccgatcgttg | 4380 |
| tcagaagtaa gttggccgca gtgttatcac tcatggttat ggcagcactg cataattctc | 4440 |
| ttactgtcat gccatccgta agatgctttt ctgtgactgg tgagtactca accaagtcat | 4500 |
| tctgagaata gtgtatgcgg cgaccgagtt gctcttgccc ggcgtcaata cgggataata | 4560 |
| ccgcgccaca tagcagaact ttaaaagtgc tcatcattgg aaaacgttct cggggcgaa | 4620 |
| aactctcaag gatcttaccg ctgttgagat ccagttcgat gtaacccact cgtgcaccca | 4680 |
| actgatcttc agcatctttt actttcacca gcgtttctgg gtgagcaaaa acaggaaggc | 4740 |
| aaaatgccgc aaaaaaggga ataagggcga cacggaaatg ttgaatactc atactcttcc | 4800 |
| tttttcaata ttattgaagc atttatcagg gttattgtct catgagcgga tacatatttg | 4860 |
| aatgtattta gaaaaataaa caaataggggg ttccgcgcac atttccccga aaagtgccac | 4920 |
| ctgctaagaa accattatta tcatgacatt aacctataaa aataggcgta tcacgaggcc | 4980 |
| ctttcgtc | 4988 |

<210> SEQ ID NO 18
<211> LENGTH: 4979
<212> TYPE: DNA
<213> ORGANISM: Artificial Sequence
<220> FEATURE:
<221> NAME/KEY: source
<222> LOCATION: 1..4979
<223> OTHER INFORMATION: /organism="Artificial Sequence"
      /note="vector construct"
      /mol_type="unassigned DNA"

<400> SEQUENCE: 18

| | |
|---|---|
| tcgcgcgttt cggtgatgac ggtgaaaacc tctgacacat gcagctcccg gagacggtca | 60 |
| cagcttgtct gtaagcggat gccggagca gacaagcccg tcaggcgcg tcagcgggtg | 120 |
| ttggcgggtg tcggggctgg cttaactatg cggcatcaga gcagattgta ctgagagtgc | 180 |

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctacctgac gcttttatc gcaactctct actgtttctc catacccgtt ttttgggct    480 agaaataatt ttgtttaact ttaagaagga gatatacccca tggctaatgc atgcaatggg    540
acgtcgggtg gaagcggtat ggtgagcaag ggcgaggagg ataacatggc catcatcaag    600
gagttcatgc gcttcaaggt gcacatggag ggctccgtga acggccacga gttcgagatc    660
gagggcgagg gcgagggccg cccctacgag ggcacccaga ccgccaagct gaaggtgacc    720
aagggtggcc ccctgccctt cgcctgggac atcctgtccc ctcagttcat gtacggctcc    780
aaggcctacg tgaagcaccc cgccgacatc cccgactact tgaagctgtc cttccccgag    840
ggcttcaagt gggagcgcgt gatgaacttc gaggacggcg gcgtggtgac cgtgacccag    900
gactcctccc tgcaggacgg cgagttcatc tacaaggtga agctgcgcgg caccaacttc    960
ccctccgacg gccccgtaat gcagaagaag accatgggct gggaggcctc ctccgagcgg   1020
atgtaccccg aggacggcgc cctgaagggc gagatcaagc agaggctgaa gctgaaggac   1080
ggcggccact acgacgctga ggtcaagacc acctacaagg ccaagaagcc cgtgcagctg   1140
cccggcgcct acaacgtcaa catcaagttg gacatcacct cccacaacga ggactacacc   1200
atcgtggaac agtacgaacg cgccgagggc cgccactcca ccggcggcat ggacgagctg   1260
tacaagtaag tgtaggctgg agctgcttcg aagttcctat actttctaga aataggaac    1320 ttcggaatag gaacttcaag atcccctcac gctgccgcaa gcactcaggg cgcaagggct   1380
gctaaaggaa gcggaacacg tagaaagcca gtccgcagaa acggtgctga ccccggatga   1440
atgtcagcta ctgggctatc tggacaaggg aaaacgcaag cgcaaagaga agcaggtag    1500 cttgcagtgg gcttacatgg cgatagctag actgggcggt tttatggaca gcaagcgaac   1560
cggaattgcc agctggggcg ccctctggta aggttgggaa gccctgcaaa gtaaactgga   1620
tggctttctt gccgccaagg atctgatggc gcagggatc aagatctgat caagagacag    1680
gatgaggatc gtttcgcatg attgaacaag atggattgca cgcaggttct ccggccgctt   1740
gggtggagag gctattcggc tatgactggg cacaacagac aatcggctgc tctgatgccg   1800
ccgtgttccg gctgtcagcg caggggcgcc cggttctttt tgtcaagacc gacctgtccg   1860
gtgccctgaa tgaactgcag gacgaggcag cgcggctatc gtggctggcc acgacgggcg   1920
ttccttgcgc agctgtgctc gacgttgtca ctgaagcggg aagggactgg ctgctattgg   1980
gcgaagtgcc ggggcaggat ctcctgtcat ctcaccttgc tcctgccgag aaagtatcca   2040
tcatggctga tgcaatgcgg cggctgcata cgcttgatcc ggctacctgc ccattcgacc   2100
accaagcgaa acatcgcatc gagcgagcac gtactcggat ggaagccggt cttgtcgatc   2160
aggatgatct ggacgaagag catcaggggc tcgcgccagc cgaactgttc gccaggctca   2220
aggcgcgcat gcccgacggc gaggatctcg tcgtgaccca tggcgatgcc tgcttgccga   2280
atatcatggt ggaaaatggc cgcttttctg gattcatcga ctgtggccgg ctgggtgtgg   2340
cggaccgcta tcaggacata gcgttggcta cccgtgatat tgctgaagag cttggcggcg   2400
aatgggctga ccgcttcctc gtgctttacg gtatcgccgc tcccgattcg cagcgcatcg   2460
ccttctatcg ccttcttgac gagttcttct gagcgggact ctggggttcg aaatgaccga   2520
```

```
ccaagcgacg cccaacctgc catcacgaga tttcgattcc accgccgcct tctatgaaag   2580
gttgggcttc ggaatcgttt tccgggacgc cggctggatg atcctccagc gcggggatct   2640
catgctggag ttcttcgccc accccagctt caaaagcgct ctgaagttcc tatactttct   2700
agagaatagg aacttcggaa taggaactaa ggaggatatt cataagcttg gcgtaatcat   2760
ggtcatagct gtttcctgtg tgaaattgtt atccgctcac aattccacac aacatacgag   2820
ccggaagcat aaagtgtaaa gcctggggtg cctaatgagt gagctaactc acattaattg   2880
cgttgcgctc actgcccgct ttccagtcgg gaaacctgtc gtgccagctg cattaatgaa   2940
tcggccaacg cgcggggaga ggcggtttgc gtattgggcg ctcttccgct tcctcgctca   3000
ctgactcgct gcgctcggtc gttcggctgc ggcgagcggt atcagctcac tcaaaggcgg   3060
taatacggtt atccacagaa tcaggggata acgcaggaaa gaacatgtga gcaaaaggcc   3120
agcaaaaggc caggaaccgt aaaaaggccg cgttgctggc gtttttccat aggctccgcc   3180
cccctgacga gcatcacaaa aatcgacgct caagtcagag gtggcgaaac ccgacaggac   3240
tataaagata ccaggcgttt ccccctggaa gctccctcgt gcgctctcct gttccgaccc   3300
tgccgcttac cggatacctg tccgcctttc tcccttcggg aagcgtggcg ctttctcata   3360
gctcacgctg taggtatctc agttcggtgt aggtcgttcg ctccaagctg ggctgtgtgc   3420
acgaaccccc cgttcagccc gaccgctgcg ccttatccgg taactatcgt cttgagtcca   3480
acccggtaag acacgactta tcgccactgg cagcagccac tggtaacagg attagcagag   3540
cgaggtatgt aggcggtgct acagagttct tgaagtggtg gcctaactac ggctacacta   3600
gaagaacagt atttggtatc tgcgctctgc tgaagccagt taccttcgga aaaagagttg   3660
gtagctcttg atccggcaaa caaaccaccg ctggtagcgg tggtttttttt gtttgcaagc   3720 agcagattac gcgcagaaaa aaaggatctc aagaagatcc tttgatcttt tctacggggt   3780
ctgacgctca gtggaacgaa aactcacgtt aagggatttt ggtcatgaga ttatcaaaaa   3840
ggatcttcac ctagatcctt ttaaattaaa aatgaagttt taaatcaatc taagtatat    3900 atgagtaaac ttggtctgac agttaccaat gcttaatcag tgaggcacct atctcagcga   3960
tctgtctatt tcgttcatcc atagttgcct gactccccgt cgtgtagata actacgatac   4020
gggagggctt accatctggc cccagtgctg caatgatacc gcgagaccca cgctcaccgg   4080
ctccagattt atcagcaata aaccagccag ccggaagggc cgagcgcaga agtggtcctg   4140
caactttatc cgcctccatc cagtctatta attgttgccg ggaagctaga gtaagtagtt   4200
cgccagttaa tagtttgcgc aacgttgttg ccattgctac aggcatcgtg gtgtcacgct   4260
cgtcgtttgg tatggcttca ttcagctccg gttcccaacg atcaaggcga gttacatgat   4320
cccccatgtt gtgcaaaaaa gcggttagct ccttcggtcc tccgatcgtt gtcagaagta   4380
agttggccgc agtgttatca ctcatggtta tggcagcact gcataattct cttactgtca   4440
tgccatccgt aagatgcttt tctgtgactg gtgagtactc aaccaagtca ttctgagaat   4500
agtgtatgcg gcgaccgagt tgctcttgcc cggcgtcaat acgggataat accgcgccac   4560
atagcagaac tttaaaagtg ctcatcattg gaaaacgttc ttcggggcga aaactctcaa   4620
ggatcttacc gctgttgaga tccagttcga tgtaacccac tcgtgcaccc aactgatctt   4680
cagcatcttt tactttcacc agcgtttctg ggtgagcaaa aacaggaagg caaaatgccg   4740
caaaaaaggg aataagggcg acacggaaat gttgaatact catactcttc ctttttcaat   4800
attattgaag catttatcag ggttattgtc tcatgagcgg atacatattt gaatgtattt   4860
agaaaaataa acaaataggg gttccgcgca catttccccg aaaagtgcca cctgctaaga   4920
```
aaccattatt atcatgacat taacctataa aaataggcgt atcacgaggc cctttcgtc    4979

<210> SEQ ID NO 19
<211> LENGTH: 4960
<212> TYPE: DNA
<213> ORGANISM: Artificial Sequence
<220> FEATURE:
<221> NAME/KEY: source
<222> LOCATION: 1..4960
<223> OTHER INFORMATION: /organism="Artificial Sequence"
      /note="vector construct"
      /mol_type="unassigned DNA"

<400> SEQUENCE: 19
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctacctgac gctttttatc gcaactctct actgtttctc catacccgtt ttttgggct      480 agaaataatt ttgtttaact ttaagaagga gatatacccc tggctaatgc atgcaatggg     540
acgtcgggtg gaagcggtat ggtcagcgtg attaagccgg aaatgaagat taaactgtgt     600
atgcgtggta cggtgaacgg tcataacttt gtgattgaag gcgaaggtaa aggcaacccg     660
tatgaaggta cccagattct ggatctgaat gttacgaaag gcgcaccgct gccgtttgct     720
tatgacatcc tgaccacggt cttcaatac ggtaaccgtc gttcaccaa atatccggcc       780 gatattcagg actactttaa gcaaaccttc ccggaaggct atcattggga acgcagcatg     840
acgtacgaag atcagggtat ttgcaccgca acgagcaata tctctatgcg tggcgattgc     900
tttttctatg atattcgctt tgacggtacc aacttcccgc gaatggccc ggtgatgcag       960 aagaaaaccc tgaaatggga accgagcacg gaaaagatgt acgtggaaga tggtgttctg    1020
aaaggcgacg ttaacatgcg tctgctgctg gaaggcggtg gccattatcg ctgcgatttc    1080
aaaaccacgt acaaggcaaa aaaggaagtc cgtctgccgg atgctcataa aattgaccac    1140
cgcattgaaa tcctgaaaca cgataaggac tataacaaag tcaagctgta cgaaaatgcg    1200
gtggcccgtt atagtatgct gccgtcccag gccaaataat gtacaagtaa gtgtaggctg    1260
gagctgcttc gaagttccta tactttctag agaataggaa cttcggaata ggaacttcaa    1320
gatcccctca cgctgccgca agcactcagg gcgcaagggc tgctaaagga gcggaacac     1380 gtagaaagcc agtccgcaga aacggtgctg accccggatg aatgtcagct actgggctat    1440
ctggacaagg gaaaacgcaa gcgcaaagag aaagcaggta gcttgcagtg gcttacatg     1500 gcgatagcta gactgggcgg ttttatggac agcaagcgaa ccggaattgc cagctggggc    1560
gccctctggt aaggttggga agccctgcaa agtaaactgg atggctttct tgccgccaag    1620
gatctgatgg cgcaggggat caagatctga tcaagagaca ggatgaggat cgtttcgcat    1680
gattgaacaa gatggattgc acgcaggttc tccggccgct tgggtggaga ggctattcgg    1740
ctatgactgg gcacaacaga caatcggctg ctctgatgcc gccgtgttcc ggctgtcagc    1800
gcaggggcgc ccggttcttt ttgtcaagac cgacctgtcc ggtgccctga atgaactgca    1860

```
ggacgaggca gcgcggctat cgtggctggc cacgacgggc gttccttgcg cagctgtgct    1920
cgacgttgtc actgaagcgg aagggactg gctgctattg ggcgaagtgc cggggcagga     1980
tctcctgtca tctcaccttg ctcctgccga gaaagtatcc atcatggctg atgcaatgcg    2040
gcggctgcat acgcttgatc cggctacctg cccattcgac caccaagcga acatcgcat    2100 cgagcgagca cgtactcgga tggaagccgg tcttgtcgat caggatgatc tggacgaaga    2160
gcatcagggg ctcgcgccag ccgaactgtt cgccaggctc aaggcgcgca tgcccgacgg    2220
cgaggatctc gtcgtgaccc atggcgatgc ctgcttgccg aatatcatgg tggaaaatgg    2280
ccgcttttct ggattcatcg actgtggccg gctgggtgtg gcggaccgct atcaggacat    2340
agcgttggct acccgtgata ttgctgaaga gcttggcggc gaatgggctg accgcttcct    2400
cgtgctttac ggtatcgccg ctcccgattc gcagcgcatc gccttctatc gccttcttga    2460
cgagttcttc tgagcgggac tctggggttc gaaatgaccg accaagcgac gcccaacctg    2520
ccatcacgag atttcgattc caccgccgcc ttctatgaaa ggttgggctt cggaatcgtt    2580
ttccgggacg ccgctggat gatcctccag cgcgggat tcatgctgga gttcttcgcc       2640 cacccagct tcaaaagcgc tctgaagttc ctatactttc tagagaatag gaacttcgga    2700
ataggaacta aggaggatat tcataagctt ggcgtaatca tggtcatagc tgtttcctgt    2760
gtgaaattgt tatccgctca caattccaca acatacga gccggaagca taaagtgtaa    2820
agcctggggt gcctaatgag tgagctaact cacattaatt gcgttgcgct cactgcccgc    2880
tttccagtcg ggaaacctgt cgtgccagct gcattaatga atcggccaac gcgcggggag    2940
aggcggtttg cgtattgggc gctcttccgc ttcctcgctc actgactcgc tgcgctcggt    3000
cgttcggctg cggcgagcgg tatcagctca ctcaaaggcg gtaatacggt tatccacaga    3060 atcagggat aacgcaggaa agaacatgtg agcaaaaggc cagcaaaagg ccaggaaccg    3120
taaaaaggcc gcgttgctgg cgtttttcca taggctccgc cccctgacg agcatcacaa    3180 aaatcgacgc tcaagtcaga ggtggcgaaa cccgacagga ctataaagat accaggcgtt    3240 tcccctgga agctccctcg tgcgctctcc tgttccgacc ctgccgctta ccggatacct    3300
gtccgccttt ctcccttcgg gaagcgtggc gctttctcat agctcacgct gtaggtatct    3360
cagttcggtg taggtcgttc gctccaagct gggctgtgtg cacgaacccc ccgttcagcc    3420
cgaccgctgc gccttatccg gtaactatcg tcttgagtcc aacccggtaa gacacgactt    3480
atcgccactg gcagcagcca ctggtaacag gattagcaga gcgaggtatg taggcggtgc    3540
tacagagttc ttgaagtggt ggcctaacta cggctacact agaagaacag tatttggtat    3600
ctgcgctctg ctgaagccag ttaccttcgg aaaaagagtt ggtagctctt gatccggcaa    3660
acaaaccacc gctggtagcg gtggtttttt tgtttgcaag cagcagatta cgcgcagaaa    3720
aaaaggatct caagaagatc ctttgatctt ttctacgggg tctgacgctc agtggaacga    3780
aaactcacgt taagggattt tggtcatgag attatcaaaa aggatcttca cctagatcct    3840
tttaaattaa aaatgaagtt ttaaatcaat ctaaagtata tatgagtaaa cttggtctga    3900
cagttaccaa tgcttaatca gtgaggcacc tatctcagcg atctgtctat ttcgttcatc    3960
catagttgcc tgactccccg tcgtgtagat aactacgata cgggagggct taccatctgg    4020
ccccagtgct gcaatgatac cgcgagaccc acgctcaccg gctccagatt tatcagcaat    4080
aaaccagcca gccggaaggg ccgagcgcag aagtggtcct gcaactttat ccgcctccat    4140
ccagtctatt aattgttgcc gggaagctag agtaagtagt cgccagtta atagtttgcg    4200 caacgttgtt gccattgcta caggcatcgt ggtgtcacgc tcgtcgtttg gtatggcttc    4260
```

```
attcagctcc ggttcccaac gatcaaggcg agttacatga tcccccatgt tgtgcaaaaa    4320
agcggttagc tccttcggtc ctccgatcgt tgtcagaagt aagttggccg cagtgttatc    4380
actcatggtt atggcagcac tgcataattc tcttactgtc atgccatccg taagatgctt    4440
ttctgtgact ggtgagtact caaccaagtc attctgagaa tagtgtatgc ggcgaccgag    4500
ttgctcttgc ccggcgtcaa tacgggataa taccgcgcca catagcagaa ctttaaaagt    4560
gctcatcatt ggaaaacgtt cttcggggcg aaaactctca aggatcttac cgctgttgag    4620
atccagttcg atgtaaccca ctcgtgcacc caactgatct tcagcatctt ttactttcac    4680
cagcgtttct gggtgagcaa aaacaggaag gcaaaatgcc gcaaaaaagg gaataagggc    4740
gacacggaaa tgttgaatac tcatactctt ccttttcaa tattattgaa gcatttatca     4800
gggttattgt ctcatgagcg gatacatatt tgaatgtatt tagaaaaata acaaataggg    4860
ggttccgcgc acatttcccc gaaaagtgcc acctgctaag aaaccattat tatcatgaca    4920
ttaacctata aaaataggcg tatcacgagg ccctttcgtc                          4960
```

<210> SEQ ID NO 20
<211> LENGTH: 4988
<212> TYPE: DNA
<213> ORGANISM: Artificial Sequence
<220> FEATURE:
<221> NAME/KEY: source
<222> LOCATION: 1..4988
<223> OTHER INFORMATION: /organism="Artificial Sequence"
        /note="vector construct"
        /mol_type="unassigned DNA"

<400> SEQUENCE: 20

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctacctgac gctttttatc gcaactctct actgtttctc cataccgttt tttttgggct     480
agaaataatt ttgtttaact ttaagaagga gatatacca tggctaatgc atgcaatggg     540
acgtcgggtg gaagcggtat ggtgagcaag ggcgaggagc tgttcaccgg ggtggtgccc     600
atcctggtcg agctggacgg cgacgtaaac ggccacaagt tcagcgtgtc cggcgagggc     660
gagggcgatg ccacctacgg caagctgacc ctgaagttca tctgcaccac cggcaagctg    720
cccgtgccct ggcccaccct cgtgaccacc ctgacctggg cgtgcagtg cttcagccgc     780 taccccgacc acatgaagca gcacgacttc ttcaagtccg ccatgcccga aggctacgtc     840
caggagcgca ccatcttctt caaggacgac ggcaactaca agacccgcgc cgaggtgaag    900
ttcgagggcg acaccctggt gaaccgcatc gagctgaagg gcatcgactt caaggaggac    960
ggcaacatcc tggggcacaa gctggagtac aactacatca gccacaacgt ctatatcacc    1020
gccgacaagc agaagaacgg catcaaggcc aacttcaaga tccgccacaa catcgaggac    1080
ggcagcgtgc agctcgccga ccactaccag cagaacaccc ccatcggcga cggccccgtg    1140
ctgctgcccg acaaccacta cctgagcacc cagtccaagc tgagcaaaga ccccaacgag    1200
```

```
aagcgcgatc acatggtcct gctggagttc gtgaccgccg ccgggatcac tctcggcatg    1260
gacgagctgt acaagtaagt gtaggctgga gctgcttcga agttcctata ctttctagag    1320
aataggaact tcggaatagg aacttcaaga tccccctcacg ctgccgcaag cactcagggc   1380
gcaagggctg ctaaaggaag cggaacacgt agaaagccag tccgcagaaa cggtgctgac    1440
cccggatgaa tgtcagctac tgggctatct ggacaaggga aaacgcaagc gcaaagagaa    1500
agcaggtagc ttgcagtggg cttacatggc gatagctaga ctgggcggtt ttatggacag    1560
caagcgaacc ggaattgcca gctggggcgc cctctggtaa ggttgggaag ccctgcaaag    1620
taaactggat ggcttcttg ccgccaagga tctgatggcg caggggatca agatctgatc     1680
aagagacagg atgaggatcg tttcgcatga ttgaacaaga tggattgcac gcaggttctc    1740
cggccgcttg ggtggagagg ctattcggct atgactgggc acaacagaca atcggctgct    1800
ctgatgccgc cgtgttccgg ctgtcagcgc agggggcgccc ggttcttttt gtcaagaccg   1860
acctgtccgg tgccctgaat gaactgcagg acgaggcagc gcggctatcg tggctggcca    1920
cgacgggcgt tccttgcgca gctgtgctcg acgttgtcac tgaagcggga agggactggc    1980
tgctattggg cgaagtgccg gggcaggatc tcctgtcatc tcaccttgct cctgccgaga    2040
aagtatccat catggctgat gcaatgcggc ggctgcatac gcttgatccg gctacctgcc    2100
cattcgacca ccaagcgaaa catcgcatcg agcgagcacg tactcggatg aagccggtc     2160 ttgtcgatca ggatgatctg gacgaagagc atcaggggct cgcgccagcc gaactgttcg    2220
ccaggctcaa ggcgcgcatg cccgacggcg aggatctcgt cgtgacccat ggcgatgcct    2280
gcttgccgaa tatcatggtg gaaaatggcc gcttttctgg attcatcgac gtggccggc     2340 tgggtgtggc ggaccgctat caggacatag cgttggctac ccgtgatatt gctgaagagc    2400
ttggcggcga atgggctgac cgcttcctcg tgctttacgg tatcgccgct cccgattcgc    2460
agcgcatcgc cttctatcgc cttcttgacg agttcttctg agcgggactc tggggttcga    2520
aatgaccgac caagcgacgc ccaacctgcc atcacgagat ttcgattcca ccgccgcctt    2580
ctatgaaagg ttgggcttcg gaatcgtttt ccgggacgcc ggctggatga tcctccagcg    2640
cggggatctc atgctggagt tcttcgccca ccccagcttc aaaagcgctc tgaagttcct    2700
atactttcta gagaatagga acttcggaat aggaactaag gaggatattc ataagcttgg    2760
cgtaatcatg gtcatagctg tttcctgtgt gaaattgtta tccgctcaca attccacaca    2820
acatacgagc cggaagcata aagtgtaaag cctggggtgc ctaatgagtg agctaactca    2880
cattaattgc gttgcgctca ctgcccgctt tccagtcggg aaacctgtcg tgccagctgc    2940
attaatgaat cggccaacgc gcggggagag gcggtttgcg tattgggcgc tcttccgctt    3000
cctcgctcac tgactcgctg cgctcggtcg ttcggctgcg gcgagcggta tcagctcact    3060
caaaggcggt aatacggtta tccacagaat caggggataa cgcaggaaag aacatgtgag    3120
caaaaggcca gcaaaaggcc aggaaccgta aaaaggccgc gttgctggcg ttttccata    3180 ggctccgccc cctgacgag catcacaaaa atcgacgctc aagtcagagg tggcgaaacc     3240
cgacaggact ataaagatac caggcgtttc cccctggaag ctccctcgtg cgctctcctg    3300
ttccgaccct gccgcttacc ggatacctgt ccgcctttct cccttcggga agcgtggcgc    3360
tttctcatag ctcacgctgt aggtatctca gttcggtgta ggtcgttcgc tccaagctgg    3420
gctgtgtgca cgaaccccc gttcagccg accgctgcgc cttatccggt aactatcgtc     3480
ttgagtccaa cccggtaaga cacgacttat cgccactggc agcagccact ggtaacagga    3540
ttagcagagc gaggtatgta ggcggtgcta cagagttctt gaagtggtgg cctaactacg    3600
```

```
gctacactag aagaacagta tttggtatct gcgctctgct gaagccagtt accttcggaa    3660
aaagagttgg tagctcttga tccggcaaac aaaccaccgc tggtagcggt ggttttttttg   3720 tttgcaagca gcagattacg cgcagaaaaa aaggatctca agaagatcct ttgatctttt    3780 ctacgggtc tgacgctcag tggaacgaaa actcacgtta agggattttg gtcatgagat     3840
tatcaaaaag gatcttcacc tagatccttt taaattaaaa atgaagtttt aaatcaatct    3900
aaagtatata tgagtaaact tggtctgaca gttaccaatg cttaatcagt gaggcaccta    3960
tctcagcgat ctgtctattt cgttcatcca tagttgcctg actccccgtc gtgtagataa    4020
ctacgatacg ggagggctta ccatctggcc ccagtgctgc aatgataccg cgagacccac    4080
gctcaccggc tccagattta tcagcaataa accagccagc cggaagggcc gagcgcagaa    4140
gtggtcctgc aactttatcc gcctccatcc agtctattaa ttgttgccgg gaagctagag    4200
taagtagttc gccagttaat agtttgcgca acgttgttgc cattgctaca ggcatcgtgg    4260
tgtcacgctc gtcgtttggt atggcttcat tcagctccgg ttcccaacga tcaaggcgag    4320
ttacatgatc ccccatgttg tgcaaaaaag cggttagctc cttcggtcct ccgatcgttg    4380
tcagaagtaa gttggccgca gtgttatcac tcatggttat ggcagcactg cataattctc    4440
ttactgtcat gccatccgta agatgctttt ctgtgactgg tgagtactca accaagtcat    4500
tctgagaata gtgtatgcgg cgaccgagtt gctcttgccc ggcgtcaata cgggataata    4560
ccgcgccaca tagcagaact ttaaaagtgc tcatcattgg aaaacgttct cggggcgaa    4620 aactctcaag gatcttaccg ctgttgagat ccagttcgat gtaacccact cgtgcaccca    4680
actgatcttc agcatctttt actttcacca gcgtttctgg gtgagcaaaa acaggaaggc    4740
aaaatgccgc aaaaaaggga ataagggcga cacggaaatg ttgaatactc atactcttcc    4800 ttttcaata ttattgaagc atttatcagg gttattgtct catgagcgga tacatatttg     4860
aatgtattta gaaaaataaa caaatagggg ttccgcgcac atttccccga aaagtgccac    4920
ctgctaagaa accattatta tcatgacatt aacctataaa aataggcgta tcacgaggcc    4980
ctttcgtc                                                            4988
```

<210> SEQ ID NO 21
<211> LENGTH: 4988
<212> TYPE: DNA
<213> ORGANISM: Artificial Sequence
<220> FEATURE:
<221> NAME/KEY: source
<222> LOCATION: 1..4988
<223> OTHER INFORMATION: /organism="Artificial Sequence"
     /note="vector construct"
     /mol_type="unassigned DNA"

<400> SEQUENCE: 21

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctacctgac gctttttatc gcaactctct actgtttctc catacccgtt ttttttgggct   480
```

-continued

| | | | | | |
|---|---|---|---|---|---|
| agaaataatt | ttgtttaact | ttaagaagga | gatataccca | tggctaatgc | atgcaatggg | 540 |
| acgtcgggtg | gaagcggtat | ggtgagcaag | ggcgaggagc | tgttcaccgg | ggtggtgccc | 600 |
| atcctggtcg | agctggacgg | cgacgtaaac | ggccacaagt | tcagcgtgtc | cggcgagggc | 660 |
| gagggcgatg | ccacctacgg | caagctgacc | ctgaagttca | tctgcaccac | cggcaagctg | 720 |
| cccgtgccct | ggcccaccct | cgtgaccacc | ttcggctacg | gcctgcagtg | cttcgcccgc | 780 |
| taccccgacc | acatgaagca | gcacgacttc | ttcaagtccg | ccatgcccga | aggctacgtc | 840 |
| caggagcgca | ccatcttctt | caaggacgac | ggcaactaca | agacccgcgc | cgaggtgaag | 900 |
| ttcgagggcg | acaccctggt | gaaccgcatc | gagctgaagg | gcatcgactt | caaggaggac | 960 |
| ggcaacatcc | tggggcacaa | gctggagtac | aactacaaca | gccacaacgt | ctatatcatg | 1020 |
| gccgacaagc | agaagaacgg | catcaaggtg | aacttcaaga | tccgccacaa | catcgaggac | 1080 |
| ggcagcgtgc | agctcgccga | ccactaccag | cagaacaccc | ccatcggcga | cggccccgtg | 1140 |
| ctgctgcccg | acaaccacta | cctgagctac | cagtccaagc | tgagcaaaga | ccccaacgag | 1200 |
| aagcgcgatc | acatggtcct | gctggagttc | gtgaccgccg | ccgggatcac | tctcggcatg | 1260 |
| gacgagctgt | acaagtaagt | gtaggctgga | gctgcttcga | agttcctata | ctttctagag | 1320 |
| aataggaact | tcggaatagg | aacttcaaga | tcccctcacg | ctgccgcaag | cactcagggc | 1380 |
| gcaagggctg | ctaaaggaag | cggaacacgt | agaaagccag | tccgcagaaa | cggtgctgac | 1440 |
| cccggatgaa | tgtcagctac | tgggctatct | ggacaaggga | aaacgcaagc | gcaaagagaa | 1500 |
| agcaggtagc | ttgcagtggg | cttacatggc | gatagctaga | ctgggcggtt | ttatggacag | 1560 |
| caagcgaacc | ggaattgcca | gctggggcgc | cctctggtaa | ggttgggaag | ccctgcaaag | 1620 |
| taaactggat | ggctttcttg | ccgccaagga | tctgatggcg | caggggatca | agatctgatc | 1680 |
| aagagacagg | atgaggatcg | tttcgcatga | ttgaacaaga | tggattgcac | gcaggttctc | 1740 |
| cggccgcttg | ggtggagagg | ctattcggct | atgactgggc | acaacagaca | atcggctgct | 1800 |
| ctgatgccgc | cgtgttccgg | ctgtcagcgc | aggggcgccc | ggttcttttt | gtcaagaccg | 1860 |
| acctgtccgg | tgccctgaat | gaactgcagg | acgaggcagc | gcggctatcg | tggctggcca | 1920 |
| cgacgggcgt | tccttgcgca | gctgtgctcg | acgttgtcac | tgaagcggga | agggactggc | 1980 |
| tgctattggg | cgaagtgccg | gggcaggatc | tcctgtcatc | tcaccttgct | cctgccgaga | 2040 |
| aagtatccat | catggctgat | gcaatgcggc | ggctgcatac | gcttgatccg | gctacctgcc | 2100 |
| cattcgacca | ccaagcgaaa | catcgcatcg | agcgagcacg | tactcggatg | gaagccggtc | 2160 |
| ttgtcgatca | ggatgatctg | gacgaagagc | atcaggggct | cgcgccagcc | gaactgttcg | 2220 |
| ccaggctcaa | ggcgcgcatg | cccgacggcg | aggatctcgt | cgtgacccat | ggcgatgcct | 2280 |
| gcttgccgaa | tatcatggtg | gaaaatggcc | gcttttctgg | attcatcgac | tgtggccggc | 2340 |
| tgggtgtggc | ggaccgctat | caggacatag | cgttggctac | ccgtgatatt | gctgaagagc | 2400 |
| ttggcggcga | atgggctgac | cgcttcctcg | tgctttacgg | tatcgccgct | cccgattcgc | 2460 |
| agcgcatcgc | cttctatcgc | cttcttgacg | agttcttctg | agcgggactc | tggggttcga | 2520 |
| aatgaccgac | caagcgacgc | ccaacctgcc | atcacgagat | ttcgattcca | ccgccgcctt | 2580 |
| ctatgaaagg | ttgggcttcg | gaatcgtttt | ccgggacgcc | ggctggatga | tcctccagcg | 2640 |
| cggggatctc | atgctggagt | tcttcgccca | ccccagcttc | aaaagcgctc | tgaagttcct | 2700 |
| atactttcta | gagaatagga | acttcggaat | aggaactaag | gaggatattc | ataagcttgg | 2760 |
| cgtaatcatg | gtcatagctg | tttcctgtgt | gaaattgtta | tccgctcaca | attccacaca | 2820 |
| acatacgagc | cggaagcata | aagtgtaaag | cctggggtgc | ctaatgagtg | agctaactca | 2880 |

```
cattaattgc gttgcgctca ctgcccgctt ccagtcggg aaacctgtcg tgccagctgc    2940
attaatgaat cggccaacgc gcggggagag gcggtttgcg tattgggcgc tcttccgctt    3000
cctcgctcac tgactcgctg cgctcggtcg ttcggctgcg gcgagcggta tcagctcact    3060
caaaggcggt aatacggtta tccacagaat caggggataa cgcaggaaag aacatgtgag    3120
caaaaggcca gcaaaaggcc aggaaccgta aaaaggccgc gttgctggcg ttttccata    3180 ggctccgccc cctgacgag catcacaaaa atcgacgctc aagtcagagg tggcgaaacc    3240
cgacaggact ataaagatac caggcgtttc cccctggaag ctccctcgtg cgctctcctg    3300
ttccgaccct gccgcttacc ggatacctgt ccgcctttct cccttcggga agcgtggcgc    3360
tttctcatag ctcacgctgt aggtatctca gttcggtgta ggtcgttcgc tccaagctgg    3420
gctgtgtgca cgaaccccc gttcagcccg accgctgcgc cttatccggt aactatcgtc    3480
ttgagtccaa cccggtaaga cacgacttat cgccactggc agcagccact ggtaacagga    3540
ttagcagagc gaggtatgta ggcggtgcta cagagttctt gaagtggtgg cctaactacg    3600
gctacactag aagaacagta tttggtatct gcgctctgct gaagccagtt accttcggaa    3660
aaagagttgg tagctcttga tccggcaaac aaaccaccgc tggtagcggt ggttttttg    3720 tttgcaagca gcagattacg cgcagaaaaa aaggatctca agaagatcct ttgatctttt    3780
ctacggggtc tgacgctcag tggaacgaaa actcacgtta agggattttg gtcatgagat    3840
tatcaaaaag gatcttcacc tagatccttt taaattaaaa atgaagtttt aaatcaatct    3900
aaagtatata tgagtaaact tggtctgaca gttaccaatg cttaatcagt gaggcaccta    3960
tctcagcgat ctgtctattt cgttcatcca tagttgcctg actccccgtc gtgtagataa    4020
ctacgatacg ggagggctta ccatctggcc ccagtgctgc aatgataccg cgagacccac    4080
gctcaccggc tccagattta tcagcaataa accagccagc cggaagggcc gagcgcagaa    4140
gtggtcctgc aactttatcc gcctccatcc agtctattaa ttgttgccgg gaagctagag    4200
taagtagttc gccagttaat agtttgcgca acgttgttgc cattgctaca ggcatcgtgg    4260
tgtcacgctc gtcgtttggt atggcttcat tcagctccgg ttcccaacga tcaaggcgag    4320
ttacatgatc ccccatgttg tgcaaaaaag cggttagctc cttcggtcct ccgatcgttg    4380
tcagaagtaa gttggccgca gtgttatcac tcatggttat ggcagcactg cataattctc    4440
ttactgtcat gccatccgta agatgctttt ctgtgactgg tgagtactca accaagtcat    4500
tctgagaata gtgtatgcgg cgaccgagtt gctcttgccc ggcgtcaata cgggataata    4560
ccgcgccaca tagcagaact ttaaaagtgc tcatcattgg aaaacgttct cggggcgaa    4620 aactctcaag gatcttaccg ctgttgagat ccagttcgat gtaacccact cgtgcaccca    4680
actgatcttc agcatctttt actttcacca gcgtttctgg gtgagcaaaa acaggaaggc    4740
aaaatgccgc aaaaaaggga ataagggcga cacggaaatg ttgaatactc atactcttcc    4800
tttttcaata ttattgaagc atttatcagg gttattgtct catgagcgga tacatatttg    4860
aatgtattta gaaaaataaa caaatagggg ttccgcgcac atttccccga aagtgccac    4920 ctgctaagaa accattatta tcatgacatt aacctataaa aataggcgta tcacgaggcc    4980
ctttcgtc                                                              4988
```

<210> SEQ ID NO 22
<211> LENGTH: 5743
<212> TYPE: DNA
<213> ORGANISM: Artificial Sequence
<220> FEATURE:

<221> NAME/KEY: source
<222> LOCATION: 1..5743
<223> OTHER INFORMATION: /organism="Artificial Sequence"
     /note="vector construct"
     /mol_type="unassigned DNA"

<400> SEQUENCE: 22

| | | | | | |
|---|---|---|---|---|---|
| atgcatttct | tccagactt | gttcaacagg | ccagccatta | cgctcgtcat | caaaatcact | 60 |
| cgcatcaacc | aaaccgttat | tcattcgtga | ttgcgcctga | gcgagacgaa | atacgcgatc | 120 |
| gctgttaaaa | ggacaattac | aaacaggaat | cgaatgcaac | cggcgcagga | acactgccag | 180 |
| cgcatcaaca | atattttcac | ctgaatcagg | atattcttct | aatacctgga | atgctgtttt | 240 |
| cccggggatc | gcagtggtga | gtaaccatgc | atcatcagga | gtacggataa | aatgcttgat | 300 |
| ggtcggaaga | ggcataaatt | ccgtcagcca | gtttagtctg | accatctcat | ctgtaacatc | 360 |
| attggcaacg | ctacctttgc | catgtttcag | aaacaactct | ggcgcatcgg | gcttcccata | 420 |
| caatcgatag | attgtcgcac | ctgattgccc | gacattatcg | cgagcccatt | tatacccata | 480 |
| taaatcagca | tccatgttgg | aatttaatcg | cggcctcgag | caagacgttt | cccgttgaat | 540 |
| atggctcata | acaccccttg | tattactgtt | tatgtaagca | gacagttttta | ttgttcatga | 600 |
| tgatatattt | ttatcttgtg | caatgtaaca | tcagagattt | tgagacacaa | cgtggctttg | 660 |
| ttgaataaat | cgaacttttg | ctgagttgaa | ggatcagatc | acgcatcttc | ccgacaacgc | 720 |
| agaccgttcc | gtggcaaagc | aaaagttcaa | aatcaccaac | tggtccacct | acaacaaagc | 780 |
| tctcatcaac | cgtggctccc | tcactttctg | gctggatgat | ggggcgattc | aggcctggta | 840 |
| tgagtcagca | acaccttctt | cacgaggcag | acctcagcgc | tagcggagtg | tatactggct | 900 |
| tactatgttg | gcactgatga | gggtgtcagt | gaagtgcttc | atgtggcagg | agaaaaaagg | 960 |
| ctgcaccggt | gcgtcagcag | aatatgtgat | acaggatata | ttccgcttcc | tcgctcactg | 1020 |
| actcgctacg | ctcggtcgtt | cgactgcggc | gagcggaaat | ggcttacgaa | cggggcggag | 1080 |
| atttcctgga | agatgccagg | aagatactta | acagggaagt | gagagggccg | cggcaaagcc | 1140 |
| gtttttccat | aggctccgcc | ccctgacaa | gcatcacgaa | atctgacgct | caaatcagtg | 1200 |
| gtggcgaaac | ccgacaggac | tataaagata | ccaggcgttt | ccctggcgg | ctccctcgtg | 1260 |
| cgctctcctg | ttcctgcctt | tcggtttacc | ggtgtcattc | cgctgttatg | gccgcgtttg | 1320 |
| tctcattcca | cgcctgacac | tcagttccgg | gtaggcagtt | cgctccaagc | tggactgtat | 1380 |
| gcacgaaccc | cccgttcagt | ccgaccgctg | cgccttatcc | ggtaactatc | gtcttgagtc | 1440 |
| caacccggaa | agacatgcaa | aagcaccact | ggcagcagcc | actggtaatt | gatttagagg | 1500 |
| agttagtctt | gaagtcatgc | gccggttaag | gctaaactga | aaggacaagt | tttggtgact | 1560 |
| gcgctcctcc | aagccagtta | cctcggttca | aagagttggt | agctcagaga | accttcgaaa | 1620 |
| aaccgccctg | caaggcggtt | ttttcgtttt | cagagcaaga | gattacgcgc | agaccaaaac | 1680 |
| gatctcaaga | agatcatctt | attaaggggt | ctgacgctca | gtggaacgaa | aactcacgtt | 1740 |
| aagggatttt | ggtcatgaga | ttatcaaaaa | ggatcttcac | ctagatcctt | ttaaattaaa | 1800 |
| aatgaagttt | taaatcaatc | taaagtatat | atgagtaaac | ttggtctgac | agttaccaat | 1860 |
| gcttaatcag | tgaggcacct | atctcagcga | tctgtctatt | tcgttcatcc | atagttgcct | 1920 |
| gactccccgt | cgtgtagata | actacgatac | gggagggctt | accatctggc | cccagtgctg | 1980 |
| caatgatacc | gcgagaccca | cgctcaccgg | ctccagattt | atcagcaata | aaccagccag | 2040 |
| ccggaagggc | cgagcgcaga | agtggtcctg | caactttatc | cgcctccatc | cagtctatta | 2100 |
| attgttgccg | ggaagctaga | gtaagtagtt | cgccagttaa | tagtttgcgc | aacgttgttg | 2160 |

```
ccattgctgc agatcgatgc ataatgtgcc tgtcaaatgg acgaagcagg gattctgcaa    2220
accctatgct actccgtcaa gccgtcaatt gtctgattcg ttaccaatta tgacaacttg    2280
acggctacat cattcacttt ttcttcacaa ccggcacgga actcgctcgg gctggccccg    2340
gtgcattttt taaatacccg cgagaaatag agttgatcgt caaaaccaac attgcgaccg    2400
acggtggcga taggcatccg ggtggtgctc aaaagcagct tcgcctggct gatacgttgg    2460
tcctcgcgcc agcttaagac gctaatccct aactgctggc ggaaaagatg tgacagacgc    2520
gacggcgaca agcaaacatg ctgtgcgacg ctggcgatat caaaattgct gtctgccagg    2580
tgatcgctga tgtactgaca agcctcgcgt acccgattat ccatcggtgg atggagcgac    2640
tcgttaatcg cttccatgcg ccgcagtaac aattgctcaa gcagatttat cgccagcagc    2700
tccgaatagc gcccttcccc ttgcccggcg ttaatgattt gcccaaacag gtcgctgaaa    2760
tgcggctggt gcgcttcatc cgggcgaaag aaccccgtat tggcaaatat tgacggccag    2820
ttaagccatt catgccagta ggcgcgcgga cgaaagtaaa cccactggtg ataccattcg    2880
cgagcctccg gatgacgacc gtagtgatga atctctcctg gcgggaacag caaaatatca    2940
cccggtcggc aaacaaattc tcgtccctga ttttttcacca cccccctgacc gcgaatggtg    3000 agattgagaa tataacccttt cattcccagc ggtcggtcga taaaaaaatc gagataaccg    3060
ttggcctcaa tcggcgttaa acccgccacc agatgggcat taaacgagta tcccggcagc    3120
aggggatcat tttgcgcttc agccatactt ttcatactcc cgccattcag agaagaaacc    3180
aattgtccat attgcatcag acattgccgt cactgcgtct tttactggct cttctcgcta    3240
accaaaccgg taaccccgct tattaaaagc attctgtaac aaagcgggac caaagccatg    3300
acaaaaacgc gtaacaaaag tgtctataat cacggcagaa aagtccacat tgattatttg    3360
cacggcgtca cactttgcta tgccatagca ttttttatcca taagattagc ggatcctacc    3420
tgacgctttt tatcgcaact ctctactgtt tctccatacc cgttttttg ggctagaaat    3480 aattttgttt aactttaaga aggagatata cccatggcta atgcatgcaa tgagaacctc    3540
tacttccaat cgatggtgag caagggcgag gaggataaca tggccatcat caaggagttc    3600
atgcgcttca aggtgcacat ggagggctcc gtgaacggcc acgagttcga gatcgagggc    3660
gagggcgagg gccgccccta cgagggcacc cagaccgcca agctgaaggt gaccaagggt    3720
ggccccctgc ccttcgcctg ggacatcctg tcccctcagt tcatgtacgg ctccaaggcc    3780
tacgtgaagc accccgccga catccccgac tacttgaagc tgtccttccc cgagggcttc    3840
aagtgggagc gcgtgatgaa cttcgaggac ggcggcgtgg tgaccgtgac ccaggactcc    3900
tccctgcagg acggcgagtt catctacaag gtgaagctgc gcggcaccaa cttcccctcc    3960
gacggccccg taatgcagaa gaagaccatg ggctgggagg cctcctccga gcggatgtac    4020
cccgaggacg gcgccctgaa gggcgagatc aagcagaggc tgaagctgaa ggacggcggc    4080
cactacgacg ctgaggtcaa gaccacctac aaggccaaga agcccgtgca gctgcccggc    4140
gcctacaacg tcaacatcaa gttggacatc acctcccaca acgaggacta caccatcgtg    4200
gaacagtacg aacgcgccga gggccgccac tccaccggcg gcatggacga gctgtacaag    4260
taagtgtagg ctggagctgc ttcgaagttc ctatactttc tagagaatag gaacttcgga    4320
ataggaactt caagatcccc tcacgctgcc gcaagcactc agggcgcaag ggctgctaaa    4380
ggaagcggaa cacgtagaaa gccagtccgc agaaacggtg ctgacccccgg atgaatgtca    4440 gctactgggc tatctggaca agggaaaacg caagcgcaaa gagaaagcag gtagcttgca    4500
```

```
gtgggcttac atggcgatag ctagactggg cggttttatg gacagcaagc gaaccggaat    4560
tgccagctgg ggcgccctct ggtaaggttg ggaagccctg caaagtaaac tggatggctt    4620
tcttgccgcc aaggatctga tggcgcaggg gatcaagatc tgatcaagag acaggatgag    4680
gatcgtttcg catgattgaa caagatggat tgcacgcagg ttctccggcc gcttgggtgg    4740
agaggctatt cggctatgac tgggcacaac agacaatcgg ctgctctgat gccgccgtgt    4800
tccggctgtc agcgcagggg cgcccggttc tttttgtcaa gaccgacctg tccggtgccc    4860
tgaatgaact gcaggacgag gcagcgcggc tatcgtggct ggccacgacg ggcgttcctt    4920
gcgcagctgt gctcgacgtt gtcactgaag cgggaaggga ctggctgcta ttgggcgaag    4980
tgccggggca ggatctcctg tcatctcacc ttgctcctgc cgagaaagta tccatcatgg    5040
ctgatgcaat gcggcggctg catacgcttg atccggctac ctgcccattc gaccaccaag    5100
cgaaacatcg catcgagcga gcacgtactc ggatggaagc cggtcttgtc gatcaggatg    5160
atctggacga agagcatcag gggctcgcgc cagccgaact gttcgccagg ctcaaggcgc    5220
gcatgcccga cggcgaggat ctcgtcgtga cccatggcga tgcctgcttg ccgaatatca    5280
tggtggaaaa tggccgcttt tctggattca tcgactgtgg ccggctgggt gtggcggacc    5340
gctatcagga catagcgttg gctacccgtg atattgctga agagcttggc ggcgaatggg    5400
ctgaccgctt cctcgtgctt tacggtatcg ccgctcccga ttcgcagcgc atcgccttct    5460
atcgccttct tgacgagttc ttctgagcgg actctgggg ttcgaaatga ccgaccaagc    5520
gacgcccaac ctgccatcac gagatttcga ttccaccgcc gccttctatg aaaggttggg    5580
cttcggaatc gttttccggg acgccggctg atgatcctc cagcgcgggg atctcatgct    5640
ggagttcttc gcccaccccca gcttcaaaag cgctctgaag ttcctatact ttctagagaa    5700
taggaacttc ggaataggaa ctaaggagga tattcataag ctt                        5743

<210> SEQ ID NO 23
<211> LENGTH: 4988
<212> TYPE: DNA
<213> ORGANISM: Artificial Sequence
<220> FEATURE:
<221> NAME/KEY: source
<222> LOCATION: 1..4988
<223> OTHER INFORMATION: /organism="Artificial Sequence"
      /note="vector construct"
      /mol_type="unassigned DNA"

<400> SEQUENCE: 23
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctacctgac gcttttatc gcaactctct actgtttctc catacccgtt ttttgggct     480 agaaataatt ttgtttaact ttaagaagga gatataccca tggctaatgc atgcaatgag     540
aacctctact ccaatcgat ggtgagcaag ggcgaggagc tgttcaccgg ggtggtgccc     600
atcctggtcg agctggacgg cgacgtaaac ggccacaagt tcagcgtgtc cggcgagggc     660
gagggcgatg ccacctacgg caagctgacc ctgaagttca tctgcaccac cggcaagctg     720
```

```
cccgtgccct ggcccaccct cgtgaccacc ttcggctacg gcctgcagtg cttcgcccgc    780
taccccgacc acatgaagca gcacgacttc ttcaagtccg ccatgcccga aggctacgtc    840
caggagcgca ccatcttctt caaggacgac ggcaactaca agacccgcgc cgaggtgaag    900
ttcgagggcg acaccctggt gaaccgcatc gagctgaagg gcatcgactt caaggaggac    960
ggcaacatcc tggggcacaa gctggagtac aactacaaca gccacaacgt ctatatcatg   1020
gccgacaagc agaagaacgg catcaaggtg aacttcaaga tccgccacaa catcgaggac   1080
ggcagcgtgc agctcgccga ccactaccag cagaacaccc ccatcggcga cggccccgtg   1140
ctgctgcccg acaaccacta cctgagctac cagtccaagc tgagcaaaga ccccaacgag   1200
aagcgcgatc acatggtcct gctggagttc gtgaccgccg ccgggatcac tctcggcatg   1260
gacgagctgt acaagtaagt gtaggctgga gctgcttcga agttcctata ctttctagag   1320
aataggaact tcggaatagg aacttcaaga tcccctcacg ctgccgcaag cactcagggc   1380
gcaagggctg ctaaaggaag cggaacacgt agaaagccag tccgcagaaa cggtgctgac   1440
cccggatgaa tgtcagctac tgggctatct ggacaaggga aaacgcaagc gcaaagagaa   1500
agcaggtagc ttgcagtggg cttacatggc gatagctaga ctgggcggtt ttatggacag   1560
caagcgaacc ggaattgcca gctggggcgc cctctggtaa ggttgggaag ccctgcaaag   1620
taaactggat ggctttcttg ccgccaagga tctgatggcg caggggatca agatctgatc   1680
aagagacagg atgaggatcg tttcgcatga ttgaacaaga tggattgcac gcaggttctc   1740
cggccgcttg ggtggagagg ctattcggct atgactgggc acaacagaca atcggctgct   1800
ctgatgccgc cgtgttccgg ctgtcagcgc agggcgcgcc ggttcttttt gtcaagaccg   1860
acctgtccgg tgccctgaat gaactgcagg acgaggcagc gcggctatcg tggctggcca   1920
cgacgggcgt tccttgcgca gctgtgctcg acgttgtcac tgaagcggga agggactggc   1980
tgctattggg cgaagtgccg gggcaggatc tcctgtcatc tcaccttgct cctgccgaga   2040
aagtatccat catggctgat gcaatgcggc ggctgcatac gcttgatccg gctacctgcc   2100
cattcgacca ccaagcgaaa catcgcatcg agcgagcacg tactcggatg gaagccggtc   2160
ttgtcgatca ggatgatctg gacgaagagc atcaggggct cgcgccagcc gaactgttcg   2220
ccaggctcaa ggcgcgcatg cccgacggcg aggatctcgt cgtgacccat ggcgatgcct   2280
gcttgccgaa tatcatggtg gaaaatggcc gcttttctgg attcatcgac tgtggccggc   2340
tgggtgtggc ggaccgctat caggacatag cgttggctac ccgtgatatt gctgaagagc   2400
ttggcggcga atgggctgac cgcttcctcg tgctttacgg tatcgccgct cccgattcgc   2460
agcgcatcgc cttctatcgc cttcttgacg agttcttctg agcgggactc tggggttcga   2520
aatgaccgac caagcgacgc ccaacctgcc atcacgagat ttcgattcca ccgccgcctt   2580
ctatgaaagg ttgggcttcg gaatcgtttt ccgggacgcc ggctggatga tcctccagcg   2640
cggggatctc atgctggagt tcttcgccca ccccagcttc aaaagcgctc tgaagttcct   2700
atactttcta gagaatagga acttcggaat aggaactaag gaggatattc ataagcttgg   2760
cgtaatcatg gtcatagctg tttcctgtgt gaaattgtta tccgctcaca attccacaca   2820
acatacgagc cggaagcata aagtgtaaag cctggggtgc ctaatgagtg agctaactca   2880
cattaattgc gttgcgctca ctgcccgctt tccagtcggg aaacctgtcg tgccagctgc   2940
attaatgaat cggccaacgc gcggggagag gcggtttgcg tattgggcgc tcttccgctt   3000
cctcgctcac tgactcgctg cgctcggtcg ttcggctgcg gcgagcggta tcagctcact   3060
```

```
caaaggcggt aatacggtta ccacagaat cagggataa cgcaggaaag aacatgtgag      3120
caaaaggcca gcaaaaggcc aggaaccgta aaaaggccgc gttgctggcg ttttccata      3180 ggctccgccc ccctgacgag catcacaaaa atcgacgctc aagtcagagg tggcgaaacc    3240
cgacaggact ataaagatac caggcgtttc cccctggaag ctccctcgtg cgctctcctg    3300
ttccgaccct gccgcttacc ggatacctgt ccgcctttct cccttcggga agcgtggcgc    3360
tttctcatag ctcacgctgt aggtatctca gttcggtgta ggtcgttcgc tccaagctgg    3420
gctgtgtgca cgaaccccc gttcagcccg accgctgcgc cttatccggt aactatcgtc     3480
ttgagtccaa cccggtaaga cacgacttat cgccactggc agcagccact ggtaacagga    3540
ttagcagagc gaggtatgta ggcggtgcta cagagttctt gaagtggtgg cctaactacg    3600
gctacactag aagaacagta tttggtatct gcgctctgct gaagccagtt accttcggaa    3660
aaagagttgg tagctcttga tccggcaaac aaaccaccgc tggtagcggt ggtttttttg    3720
tttgcaagca gcagattacg cgcagaaaaa aaggatctca agaagatcct ttgatctttt    3780 ctacgggtc tgacgctcag tggaacgaaa actcacgtta agggattttg gtcatgagat     3840
tatcaaaaag gatcttcacc tagatccttt taaattaaaa atgaagtttt aaatcaatct    3900
aaagtatata tgagtaaact tggtctgaca gttaccaatg cttaatcagt gaggcaccta    3960
tctcagcgat ctgtctattt cgttcatcca tagttgcctg actccccgtc gtgtagataa    4020
ctacgatacg ggagggctta ccatctggcc ccagtgctgc aatgataccg cgagacccac    4080
gctcaccggc tccagattta tcagcaataa accagccagc cggaagggcc gagcgcagaa    4140
gtggtcctgc aactttatcc gcctccatcc agtctattaa ttgttgccgg gaagctagag    4200
taagtagttc gccagttaat agtttgcgca acgttgttgc cattgctaca ggcatcgtgg    4260
tgtcacgctc gtcgtttggt atggcttcat tcagctccgg ttcccaacga tcaaggcgag    4320
ttacatgatc ccccatgttg tgcaaaaaag cggttagctc cttcggtcct ccgatcgttg    4380
tcagaagtaa gttggccgca gtgttatcac tcatggttat ggcagcactg cataattctc    4440
ttactgtcat gccatccgta agatgctttt ctgtgactgg tgagtactca accaagtcat    4500
tctgagaata gtgtatgcgg cgaccgagtt gctcttgccc ggcgtcaata cgggataata    4560
ccgcgccaca tagcagaact ttaaaagtgc tcatcattgg aaaacgttct cggggcgaa    4620 aactctcaag gatcttaccg ctgttgagat ccagttcgat gtaacccact cgtgcaccca    4680
actgatcttc agcatctttt actttcacca gcgtttctgg gtgagcaaaa acaggaaggc    4740
aaaatgccgc aaaaaaggga ataagggcga cacggaaatg ttgaatactc atactcttcc    4800 ttttcaata ttattgaagc atttatcagg gttattgtct catgagcgga tacatatttg     4860
aatgtattta gaaaaataaa caatagggg ttccgcgcac atttccccga aaagtgccac     4920
ctgctaagaa accattatta tcatgacatt aacctataaa aataggcgta tcacgaggcc    4980
ctttcgtc                                                             4988
```

<210> SEQ ID NO 24
<211> LENGTH: 58
<212> TYPE: DNA
<213> ORGANISM: Artificial Sequence
<220> FEATURE:
<221> NAME/KEY: source
<222> LOCATION: 1..58
<223> OTHER INFORMATION: /organism="Artificial Sequence"
      /note="primer"
      /mol_type="unassigned DNA"

<400> SEQUENCE: 24

```
acgttacacc cagctcatcg agcgcctggg tctgcgtcgc gggacgtcgg gtggaagc       58
```

<210> SEQ ID NO 25
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /organism="Artificial Sequence"
    /note="primer"
    /mol_type="unassigned DNA"

<400> SEQUENCE: 25

```
aggggccact caggccccct tttctgaaac tcgcaagaaa tgaatatcct ccttagttc    59
```

<210> SEQ ID NO 26
<211> LENGTH: 69
<212> TYPE: DNA
<213> ORGANISM: Artificial Sequence
<220> FEATURE:
<221> NAME/KEY: source
<222> LOCATION: 1..69
<223> OTHER INFORMATION: /organism="Artificial Sequence"
    /note="primer"
    /mol_type="unassigned DNA"

<400> SEQUENCE: 26

```
atgggtgcag gtgttgcagt tgaccaggct ggcctgagcg cttctgtaaa cgggacgtcg    60
ggtggaagc                                                            69
```

<210> SEQ ID NO 27
<211> LENGTH: 75
<212> TYPE: DNA
<213> ORGANISM: Artificial Sequence
<220> FEATURE:
<221> NAME/KEY: source
<222> LOCATION: 1..75
<223> OTHER INFORMATION: /organism="Artificial Sequence"
    /note="primer"
    /mol_type="unassigned DNA"

<400> SEQUENCE: 27

```
aagcattata cgtggggggta agattgtaga caaaatcacc gcccacgtaa aggcaatgaa    60
tatcctcctt agttc                                                     75
```

<210> SEQ ID NO 28
<211> LENGTH: 332
<212> TYPE: PRT
<213> ORGANISM: Artificial Sequence
<220> FEATURE:
<223> OTHER INFORMATION: fusion protein

<400> SEQUENCE: 28

```
Met Ser Leu Ser Thr Glu Ala Thr Ala Lys Ile Val Ser Glu Phe Gly
1               5                   10                  15

Arg Asp Ala Asn Asp Thr Gly Ser Thr Glu Val Gln Val Ala Leu Leu
            20                  25                  30

Thr Ala Gln Ile Asn His Leu Gln Gly His Phe Ala Glu His Lys Lys
        35                  40                  45

Asp His His Ser Arg Arg Gly Leu Leu Arg Met Val Ser Gln Arg Arg
    50                  55                  60

Lys Leu Leu Asp Tyr Leu Lys Arg Lys Asp Val Ala Arg Tyr Thr Gln
65                  70                  75                  80
```

```
Leu Ile Glu Arg Leu Gly Leu Arg Arg Gly Thr Ser Gly Ser Gly
                85                  90                  95

Met Val Ser Lys Gly Glu Asp Asn Met Ala Ile Ile Lys Glu Phe
            100                 105                 110

Met Arg Phe Lys Val His Met Glu Gly Ser Val Asn Gly His Glu Phe
        115                 120                 125

Glu Ile Glu Gly Glu Gly Glu Gly Arg Pro Tyr Glu Gly Thr Gln Thr
    130                 135                 140

Ala Lys Leu Lys Val Thr Lys Gly Gly Pro Leu Pro Phe Ala Trp Asp
145                 150                 155                 160

Ile Leu Ser Pro Gln Phe Met Tyr Gly Ser Lys Ala Tyr Val Lys His
                165                 170                 175

Pro Ala Asp Ile Pro Asp Tyr Leu Lys Leu Ser Phe Pro Glu Gly Phe
            180                 185                 190

Lys Trp Glu Arg Val Met Asn Phe Glu Asp Gly Gly Val Val Thr Val
        195                 200                 205

Thr Gln Asp Ser Ser Leu Gln Asp Gly Glu Phe Ile Tyr Lys Val Lys
    210                 215                 220

Leu Arg Gly Thr Asn Phe Pro Ser Asp Gly Pro Val Met Gln Lys Lys
225                 230                 235                 240

Thr Met Gly Trp Glu Ala Ser Ser Glu Arg Met Tyr Pro Glu Asp Gly
                245                 250                 255

Ala Leu Lys Gly Glu Ile Lys Gln Arg Leu Lys Leu Lys Asp Gly Gly
            260                 265                 270

His Tyr Asp Ala Glu Val Lys Thr Thr Tyr Lys Ala Lys Lys Pro Val
        275                 280                 285

Gln Leu Pro Gly Ala Tyr Asn Val Asn Ile Lys Leu Asp Ile Thr Ser
    290                 295                 300

His Asn Glu Asp Tyr Thr Ile Val Glu Gln Tyr Glu Arg Ala Glu Gly
305                 310                 315                 320

Arg His Ser Thr Gly Gly Met Asp Glu Leu Tyr Lys
                325                 330

<210> SEQ ID NO 29
<211> LENGTH: 467
<212> TYPE: PRT
<213> ORGANISM: Artificial Sequence
<220> FEATURE:
<223> OTHER INFORMATION: fusion protein

<400> SEQUENCE: 29

Met Ala Lys Leu Thr Lys Arg Met Arg Val Ile Arg Glu Lys Val Asp
1               5                   10                  15

Ala Thr Lys Gln Tyr Asp Ile Asn Glu Ala Ile Ala Leu Leu Lys Glu
            20                  25                  30

Leu Ala Thr Ala Lys Phe Val Glu Ser Val Asp Val Ala Val Asn Leu
        35                  40                  45

Gly Ile Asp Ala Arg Lys Ser Asp Gln Asn Val Arg Gly Ala Thr Val
    50                  55                  60

Leu Pro His Gly Thr Gly Arg Ser Val Arg Val Ala Val Phe Thr Gln
65                  70                  75                  80

Gly Ala Asn Ala Glu Ala Ala Lys Ala Ala Gly Ala Glu Leu Val Gly
                85                  90                  95

Met Glu Asp Leu Ala Asp Gln Ile Lys Lys Gly Glu Met Asn Phe Asp
            100                 105                 110
```

```
Val Val Ile Ala Ser Pro Asp Ala Met Arg Val Val Gly Gln Leu Gly
            115                 120                 125

Gln Val Leu Gly Pro Arg Gly Leu Met Pro Asn Pro Lys Val Gly Thr
    130                 135                 140

Val Thr Pro Asn Val Ala Glu Ala Val Lys Asn Ala Lys Ala Gly Gln
145                 150                 155                 160

Val Arg Tyr Arg Asn Asp Lys Asn Gly Ile Ile His Thr Thr Ile Gly
                165                 170                 175

Lys Val Asp Phe Asp Ala Asp Lys Leu Lys Glu Asn Leu Glu Ala Leu
            180                 185                 190

Leu Val Ala Leu Lys Lys Ala Lys Pro Thr Gln Ala Lys Gly Val Tyr
        195                 200                 205

Ile Lys Lys Val Ser Ile Ser Thr Thr Met Gly Ala Gly Val Ala Val
        210                 215                 220

Asp Gln Ala Gly Leu Ser Ala Ser Val Asn Gly Thr Ser Gly Gly Ser
225                 230                 235                 240

Gly Met Val Ser Val Ile Lys Pro Glu Met Lys Ile Lys Leu Cys Met
                245                 250                 255

Arg Gly Thr Val Asn Gly His Asn Phe Val Ile Glu Gly Glu Gly Lys
            260                 265                 270

Gly Asn Pro Tyr Glu Gly Thr Gln Ile Leu Asp Leu Asn Val Thr Glu
        275                 280                 285

Gly Ala Pro Leu Pro Phe Ala Tyr Asp Ile Leu Thr Thr Val Phe Gln
        290                 295                 300

Tyr Gly Asn Arg Ala Phe Thr Lys Tyr Pro Ala Asp Ile Gln Asp Tyr
305                 310                 315                 320

Phe Lys Gln Thr Phe Pro Glu Gly Tyr His Trp Glu Arg Ser Met Thr
                325                 330                 335

Tyr Glu Asp Gln Gly Ile Cys Thr Ala Thr Ser Asn Ile Ser Met Arg
            340                 345                 350

Gly Asp Cys Phe Phe Tyr Asp Ile Arg Phe Asp Gly Thr Asn Phe Pro
        355                 360                 365

Pro Asn Gly Pro Val Met Gln Lys Lys Thr Leu Lys Trp Glu Pro Ser
        370                 375                 380

Thr Glu Lys Met Tyr Val Glu Asp Gly Val Leu Lys Gly Asp Val Asn
385                 390                 395                 400

Met Arg Leu Leu Leu Glu Gly Gly Gly His Tyr Arg Cys Asp Phe Lys
                405                 410                 415

Thr Thr Tyr Lys Ala Lys Lys Glu Val Arg Leu Pro Asp Ala His Lys
            420                 425                 430

Ile Asp His Arg Ile Glu Ile Leu Lys His Asp Lys Asp Tyr Asn Lys
        435                 440                 445

Val Lys Leu Tyr Glu Asn Ala Val Ala Arg Tyr Ser Met Leu Pro Ser
        450                 455                 460

Gln Ala Lys
465
```

SCREENING FOR INHIBITORS OF RIBOSOME BIOGENESIS

RELATED APPLICATIONS

This application is a National Stage Application under 35 U.S.C. §371 of International Application Number PCT/EP2014/064720, filed on Jul. 9, 2014, which claims priority to European Application Number 13175775.9, filed on Jul. 9, 2013, the contents of which are incorporated by reference herein.

SEQUENCE LISTING

The instant application contains a Sequence Listing which has been submitted electronically in ASCII format and is hereby incorporated by reference in its entirety. Said ASCII copy, created on Jul. 9, 2014, is named 18050_010US1_SL.txt and is 66,394 bytes in size.

FIELD OF THE INVENTION

The invention relates to a method and a prokaryotic cell for identifying a compound, which interferes with ribosome biogenesis, assembly and/or degradation. The cell expresses a first fusion protein comprising a first ribosomal protein, an amino acid linker and a first fluorescent protein, and a second fusion protein comprising a second ribosomal protein, an amino acid linker and a second fluorescent protein. The invention further relates to a gene construct comprising a first element encoding a first ribosomal protein fused to a first fluorescent protein by an amino acid linker, and a second element encoding a second ribosomal protein fused to a second fluorescent protein by an amino acid linker.

BACKGROUND OF THE INVENTION

A considerable number of diseases affecting humans as well as animals are caused by microorganisms, in particular by bacteria. With the discovery of antibiotics, these diseases could be effectively treated, not only curing patients but also reducing the spread of bacterial infections. In certain cases, the use of antibiotics even enabled the extermination of diseases, at least locally. However, since some years an increasing number of bacterial resistances against antibiotics are observed, with some bacteria developing multiple resistances. The occurrence of such pathogens makes it difficult to successfully treat even rather harmless infections, which can nevertheless become life-threatening e.g. to small children or elderly people having weak immune systems. In addition, the resistances lead to the reoccurrence of infections especially in the United States of America and Europe, which had almost disappeared in these regions, as e.g. tuberculosis.

Therefore, there is a need of new compounds having antibiotic effects, i.e. inhibiting bacterial growth and proliferation, and preferably causing bacterial cell death.

SUMMARY

In a first aspect, the invention relates to a prokaryotic cell expressing a first fusion protein comprising a first ribosomal protein, an amino acid linker and a first fluorescent protein, and a second fusion protein comprising a second ribosomal protein, an amino acid linker and a second fluorescent protein, wherein the first fusion protein is expressed from the endogenous gene locus of the first ribosomal protein and the second fusion protein is expressed from the endogenous gene locus of the second ribosomal protein.

In a second aspect the invention relates to a method for identifying a compound, which interferes with ribosome biogenesis, assembly and/or degradation, comprising culturing a prokaryotic cell of the invention, measuring the fluorescence signal of the first and second fluorescent protein, adding the compound to the cell, and re-measuring the fluorescence signal of the first and second fluorescent protein, wherein a change in the fluorescence signal of the first and/or second fluorescent protein indicates that the compound interferes with ribosome biogenesis, assembly and/or degradation.

In a further aspect, the invention relates to a method of screening a library of compounds to identify one or more members having antibiotic properties, comprising culturing a prokaryotic cell of the invention, measuring the fluorescence signal of the first and second fluorescent protein, contacting the cell with at least one compound of the library, and re-measuring the fluorescence signal of the first and second fluorescent protein, wherein a change in the fluorescence signal of the first and/or second fluorescent protein indicates that the compound has antibiotic properties.

In a further aspect, the invention relates to a method for monitoring ribosome biogenesis, assembly and/or degradation comprising culturing prokaryotic cells of the invention and monitoring the fluorescence signal of the first and second fluorescent protein, wherein a change in the fluorescence signal indicates an alteration in ribosome biogenesis, assembly and/or degradation.

In a further aspect, the invention relates to the use of a prokaryotic cell of the invention for detecting and/or quantifying ribosome biogenesis, assembly and/or degradation in vitro.

In a further aspect, the invention relates to a gene construct comprising a first element encoding a first ribosomal protein fused to a first fluorescent protein by an amino acid linker, and a second element encoding a second ribosomal protein fused to a second fluorescent protein by an amino acid linker.

In a further aspect, the invention relates to a kit comprising a prokaryotic cell expressing a first fusion protein comprising a protein of a small ribosomal subunit, an amino acid linker and a first fluorescent protein from the endogenous gene locus of the protein of the small ribosomal subunit, and a second fusion protein comprising a protein of a large ribosomal subunit, an amino acid linker and a second fluorescent protein from the endogenous gene locus of the protein of the large ribosomal subunit, and a prokaryotic cell expressing a fusion protein comprising a first ribosomal protein, an amino acid linker and a first fluorescent protein from the endogenous gene locus of the first ribosomal protein and a second fusion protein comprising a second ribosomal protein, an amino acid linker and a second fluorescent protein from the endogenous gene locus of the second ribosomal protein, wherein the first ribosomal protein and the second ribosomal protein are different ribosomal proteins of the small or large ribosomal subunit.

BRIEF DESCRIPTION OF THE DRAWINGS

FIG. 3 (ii) Polysome profiles derived from: (K) MCrgS, (L) MCrgSΔsQ, (M) MCrgSΔIC. Sucrose gradient fractions of samples K-M were analyzed for mAzami- and mCherry specific fluorescence and normalized results are given in bar charts for: (N) MCrgS(O) MCrgSΔsQ (P) MCrgSΔIC. Superposition of $A_{254}$ profiles and corresponding fluorescence bar charts: (Q) MCrgS, (R) MCrgSΔsQ, (S) MCrgSΔIC. The inserts show fluorescence analysis of all available fractions from each sucrose gradient run. Bars with black lines: normalized mCherry fluorescence; Black bars: normalized mAzami fluorescence. Fluorescence was normalized to the first polysome peak ("disome") where subunits are supposed to be present in 1:1 ratio.

DETAILED DESCRIPTION OF THE INVENTION

Figure 1:
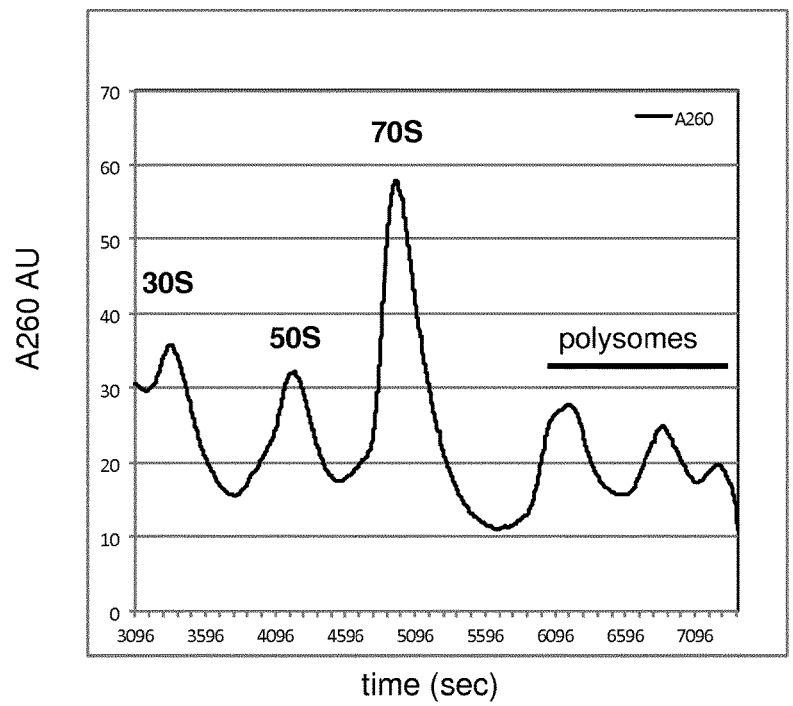
FIG. 1 shows a ribosome profile obtained from RN55b, resembling the profile of a wild-type strain (A), a fluorescence analysis of sucrose gradient fractions from RN55b detected using a fluorescence plate reader (B) and an overlay of both (C). Red and green fluorescence was set to 1 in the 70S peaks, where both subunits are present in equimolar amounts. The overlay shows that the measured fluorescence intensities reflect the amounts of large and small ribosomal subunits.
Figure 1:
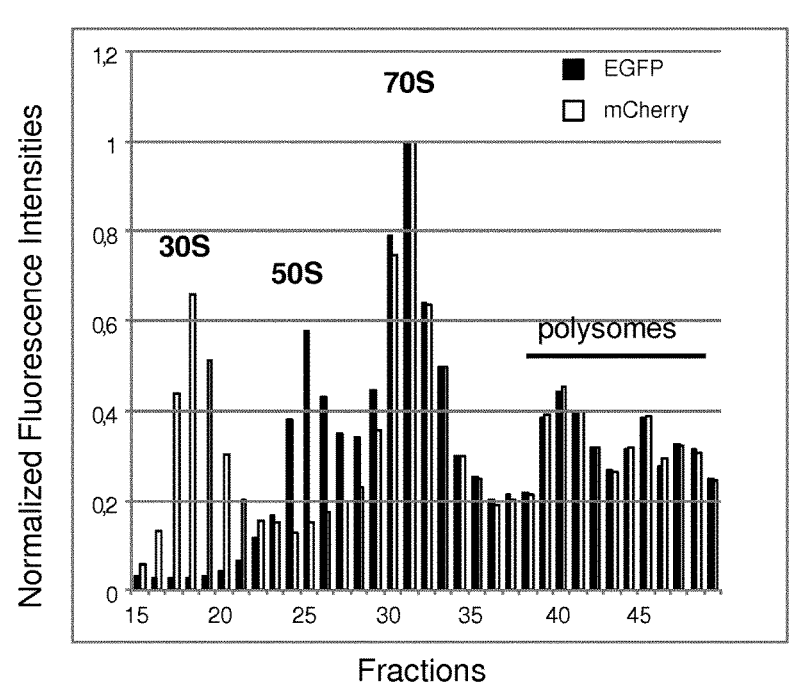
Figure 1:
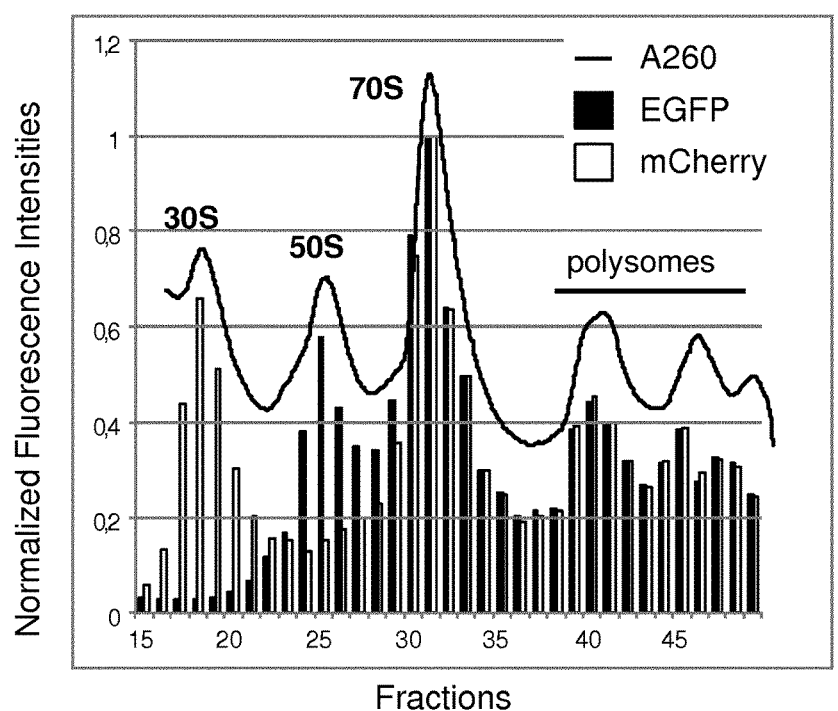

In a first aspect, the invention relates to a prokaryotic cell expressing a first fusion protein comprising a first ribosomal protein, an amino acid linker and a first fluorescent protein, and a second fusion protein comprising a second ribosomal protein, an amino acid linker and a second fluorescent protein, wherein the first fusion protein is expressed from the endogenous gene locus of the first ribosomal protein and the second fusion protein is expressed from the endogenous gene locus of the second ribosomal protein.

Ribosomes are essential components of every living cell and functionally conserved among the three kingdoms of life. They serve as catalytic platforms that translate the genetic information of the DNA into proteins, which as a whole constitute the functional proteome of a cell. The bacterial ribosome (70S) is a heterogeneous particle composed of RNA and protein elements and consists of two different units called small ribosomal subunit (30S) and large ribosomal subunit (50S). The small ribosomal subunit contains 21 ribosomal proteins (RPS 1 to 21) and one 16S ribosomal RNA (rRNA), whereas the large ribosomal subunit contains two rRNAs (23S and 5S) and 33 ribosomal proteins (RPL 1 to 36). All components of the 70S ribosome, except for the protein RPL7/12, which occurs in four copies, are present only once. During the translation process, both subunits join to form a mature, actively translating 70S ribosome. Ribosome assembly and maturation are dominated by three main events, which partially overlap: 1.) the transcription and processing of rRNAs, 2.) the coordinated binding of ribosomal proteins and 3.) chemical modifications of the rRNA and the proteins. The term "ribosome biogenesis" as used herein refers to the generation of the ribosome's components including the ribosomal proteins and the rRNA molecules. The term "ribosome assembly" as used herein comprises the grouping of the ribosomal proteins to form the small and large ribosomal subunit, respectively. The term "70S formation" refers to the joining of one large and one small ribosomal subunit to form the entire ribosome for the purpose of translation. The term "ribosome degradation" as used herein refers to the disassembly and decomposition of the ribosome's compounds. Together ribosome biogenesis, assembly and degradation determine the turnover of the ribosomal components.

The cell of the invention allows directly detecting and monitoring ribosome biogenesis, assembly and degradation, in particular it is suitable for identifying and characterizing ribosomal subunit assembly defects quantitatively and qualitatively. Depending on the ribosomal proteins chosen for labeling, different aspects of ribosomal biogenesis, assembly and degradation can be observed. In particular, the cell may simultaneously express a first fusion protein comprising a protein of the small ribosomal subunit and a first fluorescent protein and a second fusion protein comprising a protein of the large ribosomal subunit and a second fluorescent protein, wherein the ribosomal proteins are added late during the process of ribosome assembly. In this case, the expressed fusion proteins provide distinct markers of ribosomal subunits (30S and 50S, respectively) and the complete ribosome (70S). Thus, such a cell provides a fast and easy tool, especially for highthrough-put screening, for identifying compounds interfering with ribosome biogenesis and 70S assembly. Likewise, the cell may simultaneously express a first fusion protein comprising a protein of the small ribosomal subunit and a first fluorescent protein, and a second fusion protein comprising a protein of the large ribosomal subunit and a second fluorescent protein, wherein the ribosomal proteins are added early during the process of ribosome assembly. In this case, the labeled ribosomal proteins visualize not only the assembled subunits and the complete 70S ribosome, but also the various primary stages during ribosome assembly. This allows determining, e.g. by accumulation of subunit precursors of a particular stage, at which point during subunit or 70S assembly a given compound interferes with ribosome generation. In addition, in vivo analysis of cells expressing fluorescently labeled early assembling ribosomal proteins provides information regarding the turnover of ribosomes and ribosomal subunits. Taken together, this allows a detailed characterization of compounds interfering with ribosome and subunit biogenesis, assembly and degradation. In addition, the cell may simultaneously express a first fusion protein comprising a first ribosomal protein, which is e.g. integrated early during ribosome assembly, and a first fluorescent protein, and a second fusion protein comprising a second ribosomal protein, which is e.g. integrated late during ribosome assembly, and a second fluorescent protein, wherein both ribosomal proteins belong to the same subunit, i.e. to the small subunit or to the large subunit. This allows for a detailed analysis of each subunit separately. In particular, the change of fluorescent signals from reporter strains expressing labeled ribosomal proteins of the small and large subunit, respectively, may be observed in parallel. Thereby it is possible to determine the subunit specific effects of compounds interfering with ribosome assembly in specific detail. In particular, interdependencies between the two ribosomal subunits during assembly may be identified.

Figure 16:
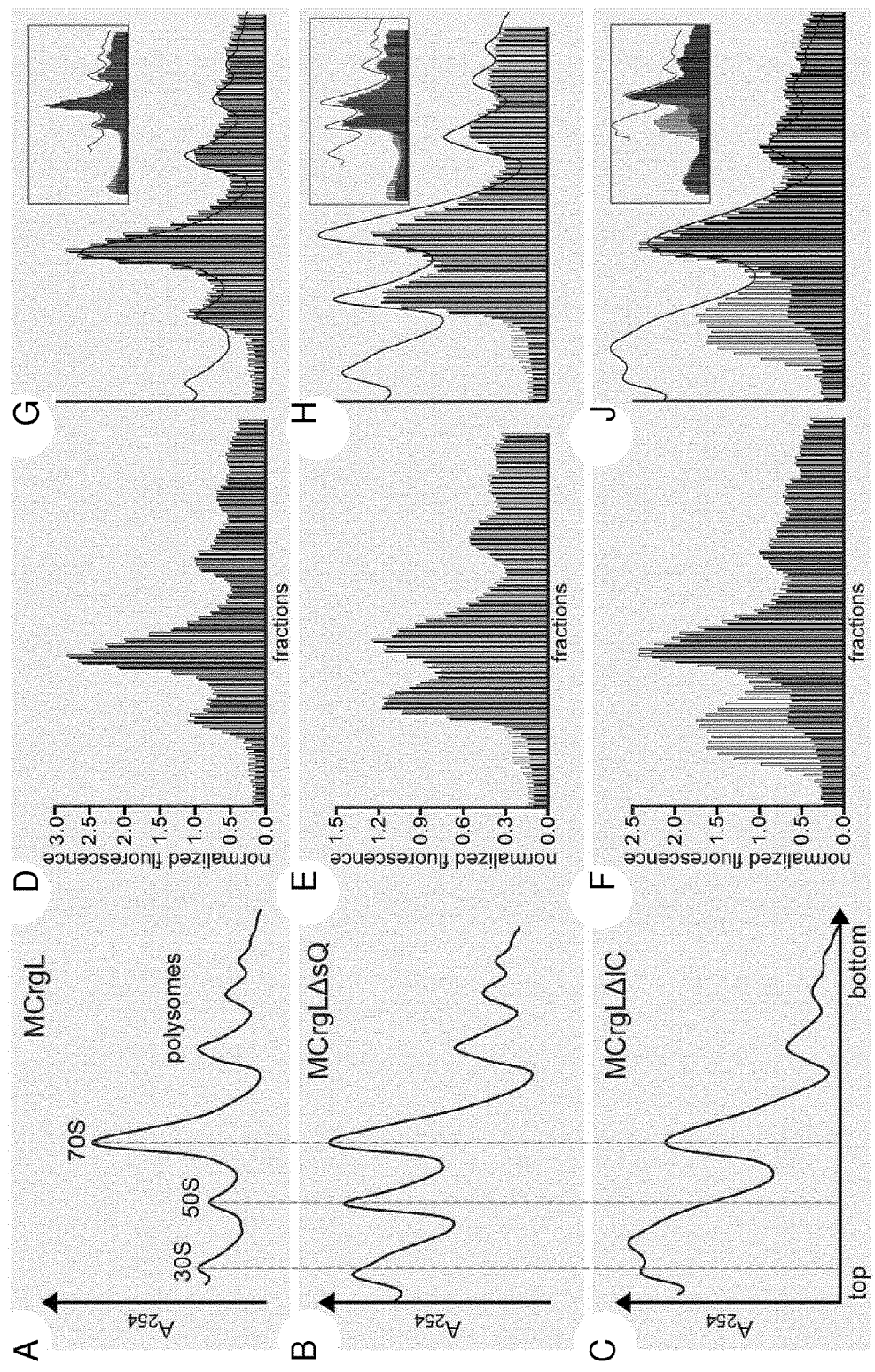
FIG. 16 shows polysome profiles derived from: (A) MCrgL, (B) MCrgLΔsQ, (C) MCrgLΔIC. Sucrose gradient fractions of samples A-C were analyzed for mAzami- and mCherry specific fluorescence and normalized results are given in bar charts for: (D) MCrgL (E) MCrgLΔsQ (F) MCrgLΔIC. Superposition of $A_{254}$ profiles and corresponding fluorescence bar charts: (G) MCrgL, (H) MCrgLΔsQ, (J) MCrgLΔIC.
Figure 16:
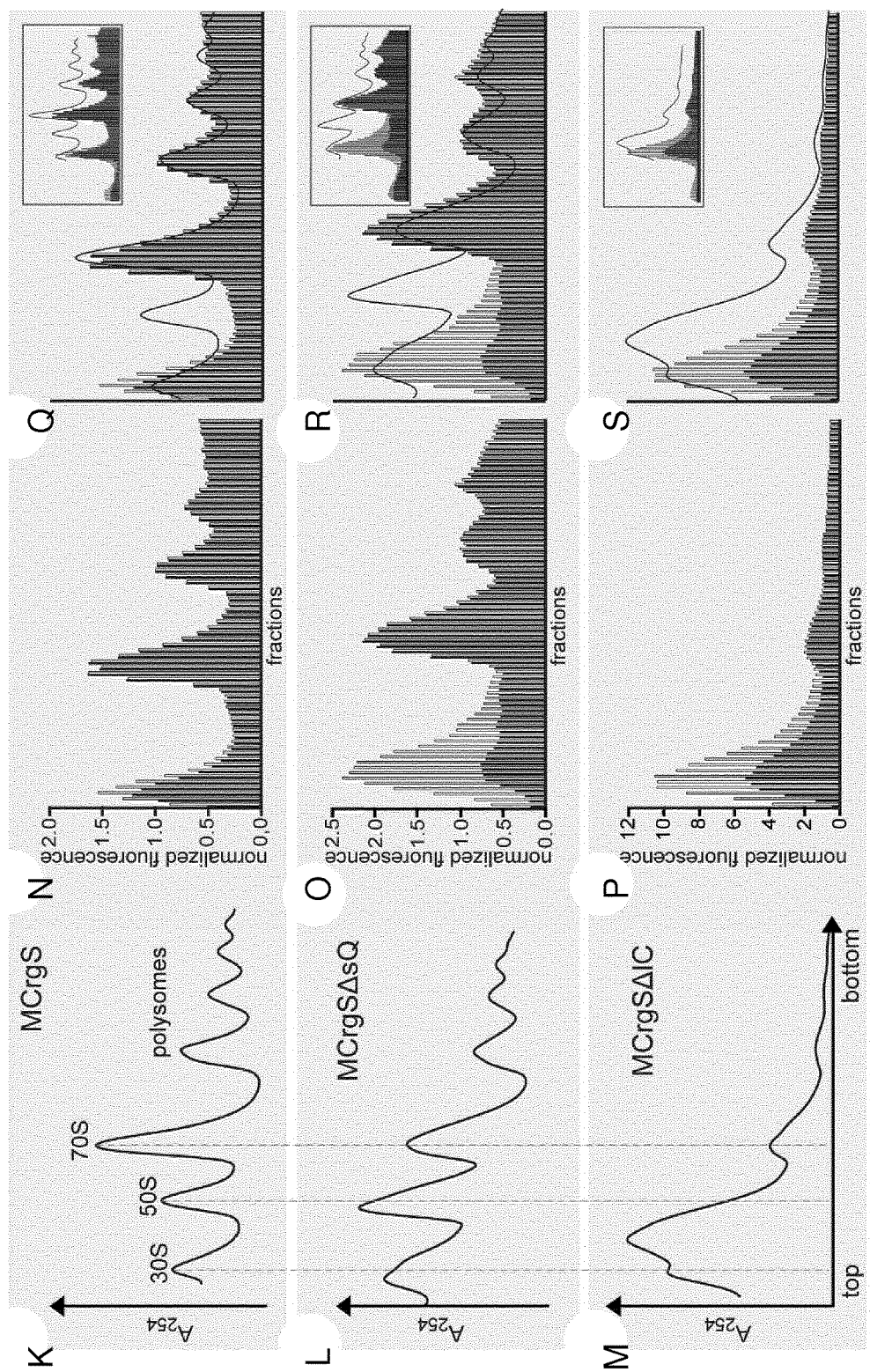

Detecting and monitoring of the ribosomal subunits and the assembled ribosome can be carried out using different techniques. For example, the fluorescence of the first and second protein can be detected within intact cells i.e. living or fixed cell cultures. Alternatively, the cells may be lysed prior to detection of the fluorescence signal of the fusion proteins. Cell lysates are easy to handle and fluorescence can be measured using spectrofluorometers with cuvettes providing fast and reliable results. Moreover, since after lysis the ribosomes comprising the fluorescent proteins are no longer encapsulated by the cell wall, the fluorescence signal is much stronger compared to intact cells. In addition, fluorescence may be detected from isolated ribosomes e.g. after centrifugation and sucrose gradient fractionation. This allows to separate ribosome particles from the other components of the cell and, additionally, to segregate 30S-, 50S subunits, 70S ribosomes and polysomes. A fluorescence analysis of segregated ribosomes from the cell of the invention shows that the fluorescence signal exactly correlates with the ribosomal subunits. In particular, the signal of the first fluorescent protein, when fused to a protein of the small ribosomal subunit, is detected in the fraction of small ribosomal subunits and the fluorescence signal of the second fluorescent protein, when fused to a protein of the large ribosomal subunit, is detected in the fractions of the large ribosomal subunit. In addition both fluorescent signals are detected in the fractions comprising assembled ribosomes and polysomes, since these comprise both, small and large ribosomal subunits (FIG. 1). Likewise, the fluorescent signal is restricted to the fractions of the small ribosomal subunit when both fusion proteins are derived from the small ribosomal subunit, and it is restricted to the fractions of the large ribosomal subunit when both fusion proteins are derived from the large ribosomal subunit (FIG. 16). Fluorometric analysis can be carried out e.g. by use of fluorometers, fluorospectrometers, fluorescent microscopes and laser scanning microscopes.

The cell of the invention expresses the fusion proteins from the endogenous loci of the protein of the small ribosomal subunit and of the protein of the large ribosomal subunit, respectively. To achieve this, a nucleic acid encoding for the linker and the fluorescent protein was introduced immediately behind the endogenous gene encoding the ribosomal protein (Knock-In). By doing so, the stop codon terminating the endogenous gene of the ribosomal protein was deleted. Consequently, the ribosomal protein, the linker and the fluorescent protein are produced as one single fusion protein. Alternatively, a nucleic sequence encoding the entire fusion protein may be introduced into the endogenous genetic locus replacing the native encoding sequence of the respective ribosomal protein. In any case, the expression of each fusion protein is under the control of the respective endogenous promoter and, thus, is expressed in a manner identical to the endogenous ribosomal protein.

In general, the synthesis of ribosomes consumes up to 40% of the whole cell energy. Accordingly, ribosome biogenesis is a strictly regulated process which allows appropriate protein translation rates at all circumstances but prevents unfavorable loss of energy. The mechanisms controlling ribosome biogenesis comprise the so-called "stringent control", which detects the absence of particular amino acids, the so-called "growth rate control", which senses low nutrient supply of carbon, and a "feedback control" in which free rRNAs and ribosomal proteins delay their own synthesis. Due to these control mechanisms, the production of ribosomal proteins is tightly connected to the assembly of the ribosomal subunits. For example, defects in the assembly of one ribosomal subunit result in an increased amount of free ribosomal proteins of the respective subunit, in case the ribosomal proteins are subject to an autogenous control. These free ribosomal proteins, in turn, inhibit the translation of ribosomal subunit proteins. Hence, the reduced production of a single ribosomal protein indicates a defect in the generation of the ribosomal subunit it belongs to. By fusing a fluorescent protein to a ribosomal protein and expressing both under the endogenous regulatory elements of the ribosomal protein, the fluorescent signal serves as readout for ribosome subunit biogenesis and assembly.

Importantly, the fusion proteins, when integrated into the cells' ribosomes do not interfere with protein synthesis, since cell growth remains normal under the expression of the ribosomal fusion proteins. This was not necessarily expected, since fluorescent proteins are rather large compared to the ribosomal proteins and knockouts of ribosomal proteins are known to exhibit strongly impaired growth.

In summary, the cell of the invention allows observing ribosome formation and turnover as well as protein translation, even in living cells. Additionally, it enables the detection of defects in ribosome subunit biogenesis, assembly and degradation. Therefore, the cell of the invention is particularly suitable to determine conditions improving or impairing prokaryotic protein synthesis and to identify compounds inhibiting or suppressing prokaryotic protein synthesis, which provides interesting potential antimicrobial substances.

Figure 2:
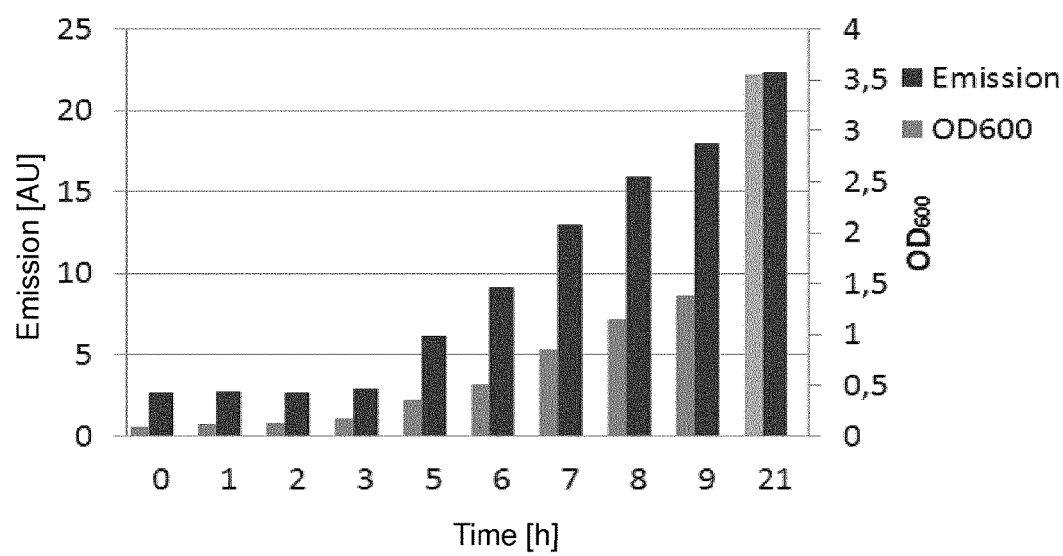
FIG. 2 shows cell density (OD 600) and fluorescence signal from wild-type MC4100 cells and MC4100 cells expressing RPL19-EGFP (A) and RPS20-EYFP (B). Density and fluorescence was measured in intervals of 1 h showing a continuous increase in both until stationary growth phase is reached.
Figure 2:
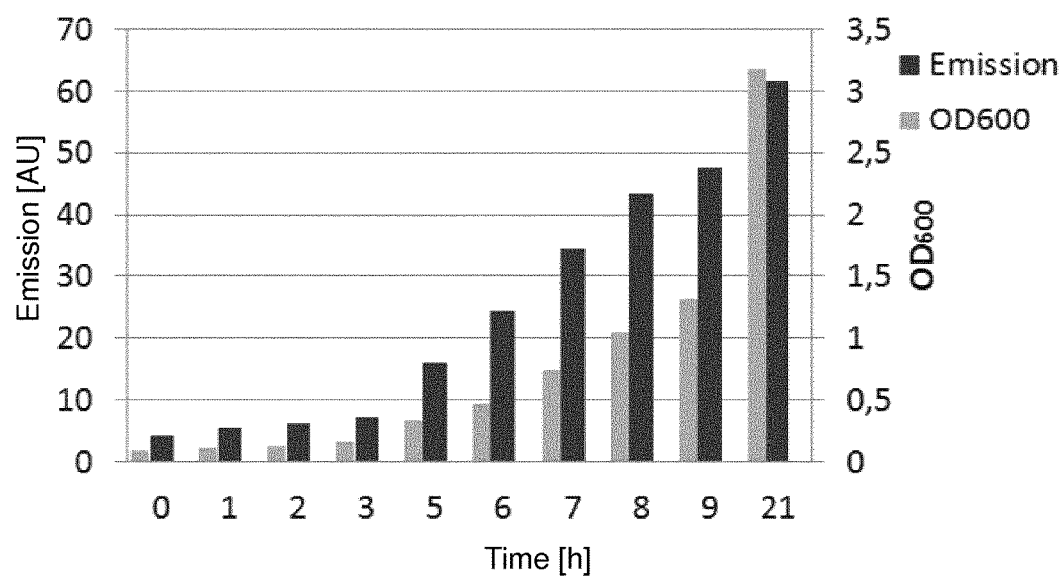

In a preferred embodiment, the first ribosomal protein is a protein of a small ribosomal subunit and the second ribosomal protein is a protein of a large ribosomal subunit. Accordingly, in a further aspect, the invention relates to a prokaryotic cell expressing a first fusion protein comprising a protein of a small ribosomal subunit, an amino acid linker and a first fluorescent protein, and a second fusion protein comprising a protein of a large ribosomal subunit, an amino acid linker and a second fluorescent protein, wherein the first fusion protein is expressed from the endogenous gene locus of the protein of the small ribosomal subunit and the second fusion protein is expressed from the endogenous gene locus of the protein of the large ribosomal subunit. The fusion proteins comprise at least one protein of the small ribosomal subunit and at least one protein of the large ribosomal subunit, each bound to a fluorescent protein by an amino acid linker. These fusion proteins become incorporated into the cells' ribosomes such that the ribosomes can be detected through the fluorescence of the fusion proteins. Since the fusion proteins specifically comprise a protein of the small ribosomal subunit and a protein of the large ribosomal subunit, respectively, it is not only possible to detect the assembled ribosome, but also the individual subunits. Thus, using the cell of the invention, detection and visualization of the small ribosomal subunit (30S), the large ribosomal subunit (50S) and the assembled ribosome (70S) is possible. Accordingly, the prokaryotic cell of the invention enables the observation of biogenesis, assembly and degradation of each ribosomal subunit and the formation of the ribosome (70S). Moreover, as a further consequence of the stringent regulation of ribosome production, under physiological conditions almost all ribosomes are actively involved in protein translation, i.e. bound to mRNA and generating proteins. Therefore, the fluorescence signal from both ribosomal subunits together provides additional information about the amount of active ribosomes in the cell and about the extent of translation. This is, for example, evident from the development of the fluorescent signal during bacterial cell growth. The fluorescence intensity was highest during the exponential growing phase when the amount of ribosomes per cell and the protein translation rate is known to be highest. Likewise, the fluorescent signal decreased with entry of the cells into the stationary phase, when protein translation stagnates (FIG. 2). Accordingly, the cell of the invention is further suitable for monitoring active protein translation.

In an alternative preferred embodiment, the first ribosomal protein and the second ribosomal protein are different ribosomal proteins of a small or large ribosomal subunit. In this case, each subunit can be analyzed individually. In particular, a cell expressing two labeled ribosomal proteins of the small subunit and another cell expressing two labeled ribosomal proteins of the large subunit may be cultured in parallel. Upon adding a compound, which is supposed to interfere with ribosome biogenesis, assembly or degradation, the change in fluorescence in both cultures can be compared, providing specific information on the effect of the compound to each subunit. Moreover, using this embodiment, the effects of the compound can be analyzed with a thorough resolution of the individual stages during ribosome generation. Alternatively, one reporter strain may be provided expressing two labeled ribosomal proteins of the small subunit and two labeled ribosomal proteins of the large subunit from the respective endogenous gene loci within one cell (knock-In of four different genes). To reliably observe the different subunits, the signals of the fluorescent proteins comprised in the four different fusion proteins need to be clearly distinguishable.

In a particular preferred embodiment, the first ribosomal protein is an early assembling ribosomal protein and the second ribosomal protein is a late assembling ribosomal protein. Thereby, various stages of subunit assembly can be monitored.

In a preferred embodiment, the first fluorescent protein and the second fluorescent protein are located towards the surface of the assembled ribosome. To achieve this, the fusion proteins comprise proteins of the small and/or large ribosomal subunit, which have at least one terminus, the C- and/or the N-terminus, located towards the outer surface of the assembled ribosome. Further, the nucleic acid encoding the fluorescent protein is fused to said terminus, such that it becomes located towards the surface when integrated into the ribosome. This reduces the risk of interactions of the fluorescent protein with the proteins of the ribosome and, thus, the risk of interference with ribosome assembly. In addition, the fluorescence signal is expected to be improved, if the fluorescent protein is located on the ribosomes surface, since interaction with ribosomal proteins might impair the signal.

For most ribosomal proteins, the C-terminus is located towards the surface of the assembled ribosome. Accordingly, in a further preferred embodiment, the first fluorescent protein is fused to the C-terminus of the first ribosomal protein and/or the second fluorescent protein is fused to the C-terminus of the second ribosomal protein. In particular, the first fluorescent protein may be fused to the C-terminus of the protein of the small ribosomal subunit and/or the second fluorescent protein may be fused to the C-terminus of the protein of the large ribosomal subunit.

In a further preferred embodiment, the protein of the small ribosomal subunit is selected from the group consisting of RPS2, RPS3, RPS5, RPS6, RPS10, RPS15, RPS16, RPS17, RPS18, RPS19 and RPS20 and/or the large ribosomal subunit is selected from the group consisting of RPL1, RPL2, RPL3, RPL4, RPL5, RPL6, RPL9, RPL10, RPL11, RPL13, RPL14, RPL15, RPL16, RPL17, RPL18, RPL19, RPL20, RPL21, RPL22, RPL23, RPL24, RPL25, RPL27, RPL30, RPL31, RPL32, RPL33 and RPL34. In *E. coli* these ribosomal proteins are known to have C-termini, which are located towards the surface of the ribosome. Since ribosomal proteins, ribosome structure, and ribosome assembly are highly conserved throughout all prokaryotic species, this also accounts for homolog proteins of other prokaryotic species. Likewise, in case the first and second ribosomal protein belong to the small ribosomal subunit, they are preferably selected from the group consisting of RPS2, RPS3, RPS5, RPS6, RPS10, RPS15, RPS16, RPS17, RPS18, RPS19 and RPS20 and in case the first and second ribosomal protein belong to the large ribosomal subunit, they are preferably selected from the group consisting of RPL1, RPL2, RPL3, RPL4, RPL5, RPL6, RPL9, RPL10, RPL11, RPL13, RPL14, RPL15, RPL16, RPL17, RPL18, RPL19, RPL20, RPL21, RPL22, RPL23, RPL24, RPL25, RPL27, RPL30, RPL31, RPL32, RPL33 and RPL34.

In a preferred embodiment, the protein of the small ribosomal subunit and/or the protein of the large ribosomal subunit are ribosomal proteins, which are added late or even last during ribosome assembly. The fusion proteins expressed in the cell of the invention become integrated into the subunits and finally into the ribosomes. Therefore, the assembly of the ribosome can be monitored by detecting the fluorescence signal. If ribosome assembly is disturbed, e.g. because one or more ribosomal proteins are not produced or an rRNA is non-functional, this will lead to a change in the fluorescence signal from one or both fusion proteins. Moreover, ribosome assembly follows a strict hierarchical order of primary, secondary and tertiary binding proteins. Accordingly, if the ribosomal protein of the fusion protein is a secondary or tertiary binding protein, defects in earlier assembly states will prevent the binding of the fusion protein to the ribosome. This results in the occurrence of free fusion proteins, which can be detected, e.g. by chromatographic techniques or ribosome isolation. In addition, due to the feedback regulation of ribosomal protein synthesis (e.g. autogenous control), the free fusion proteins will block their own synthesis resulting in a decreased fluorescence signal. The sequence of binding of ribosomal proteins has been determined for several species, e.g. by in vitro reconstruction, which provides so-called assembly maps depicting the interaction of individual ribosomal proteins and the sequence of their assembly. In *E. coli*, for example, it has been shown that RPS14, RPS21, RPS10, RPS3 and RPS2 are the last ribosomal proteins to be assembled in the small ribosomal subunit (Shajani et al., 2011).

In a preferred embodiment, the protein of the small ribosomal subunit and/or the protein of the large ribosomal subunit are ribosomal proteins, which are added early during ribosome assembly. By labeling ribosomal proteins added to the assembling ribosome early during ribosome generation, the various pre-stages during subunit and ribosome assembly can be visualized. This allows for a detailed analysis of ribosome generation. In particular, it may be determined at which stage of ribosome assembly, a compound interfering with ribosome generation, exerts its effect. This also enables the identification of subunit specific inhibiting compounds. In addition, in vivo analysis allow for observation of ribosome turnover.

In a preferred embodiment, the protein of the small ribosomal subunit and the protein of the large ribosomal subunit are not intimately involved in the translation process. Fusion proteins comprising ribosomal proteins, which do not participate in protein synthesis, are less likely to interfere with other ribosomal proteins or the rRNA, which might lead to translation deficiencies of the ribosome. Whether a given ribosomal protein is directly involved in protein translation can be predicted from the atomic structure of the ribosome, which is known for many prokaryotic species, including *E. coli*. Due to the strong homology of ribosomal structures between different prokaryotic species, predictions can even be drawn for species of which the ribosomal atomic structure has not yet been determined.

In a preferred embodiment, the protein of the small ribosomal subunit is selected from the group consisting of RPS2, RPS10, RPS12, RPS15, RPS19, and RPS20, and/or the protein of the large ribosomal subunit is selected from the group consisting of RPL1, RPL3, RPL10, RPL11, RPL19, and RPL31. These ribosomal proteins were found to be particularly suitable for providing fusion proteins with fluorescent proteins. In particular preferred embodiment, the protein of the small ribosomal subunit is RPS20, RPS2 or RPS15 and the protein of the large ribosomal subunit is RPL19, RPL10, RPL31 or RPL1. Combinations of fusion proteins comprising RPS2 and RPL19; RPS2 and RPL31; RPS20 and RPL19; RPS20 and RPL31; RPS2 and RPL10; RPS15 and RPL1, RPS15 and RPS2; and RPL1 and RPL19 show strong and reliable fluorescence while neither interfering with protein synthesis nor bacterial growth.

In a preferred embodiment, the cell is selected from the group consisting of *Escherichia coli, Salmonella* spec, *Bacillus subtilis, Thermus thermophilus, Staphylococcus aureus* and *Streptococcus pneumoniae*. The quaternary structure of the ribosome, as well as the amino acid sequence and the three-dimensional folding of the individual ribosomal proteins are highly conserved between different species, especially between prokaryotic species. Thus, fusion proteins which have been found to reliably label ribosomal subunits and ribosomes in a prokaryotic cell of a specific species, e.g. *E. coli*, are expected to likewise reliably label ribosome subunits and ribosomes using the corresponding ribosomal protein of a different prokaryotic species. However, for certain applications specific species may be preferred. For example, *E. coli* and *B. subtilis* are long and well-known experimental organisms, which are easy to culture and well-suited to perform high through-put screenings. Moreover, due to the similarity between the ribosomal molecules and processes of different prokaryotic species, compounds, which show antimicrobial (also referred to herein as antibiotic) properties against *E. coli* might well display these effects also with respect to other prokaryotic cells, in particular pathogens. Nevertheless, for carrying out a screening for compounds having antibiotic properties against specific pathogens, the respective pathogens may be directly employed, e.g. *Staphylococcus aureus, Streptococcus pneumoniae* or *Salmonella* spec.

In a preferred embodiment, the cell is selected from the *E. coli* strains MC4100 and BL21. In case the cell of the invention is an *E. coli* cell, it is preferably chosen from a MC4100 or BL21 background, since both strains are particularly suitable for genetic manipulation, e.g. phage transduction. Moreover, BL21 cells are free of the endogenous proteases Lon and ompT, such that the probability of a separation of the ribosomal protein and the fluorescent protein by enzymatic digestion is reduced.

In a preferred embodiment, the first and the second fluorescent protein are each selected from the group consisting of EBFP, ECFP, mTurquoise, mAzami-green, EGFP, sfGFP, TagGFP2, EYFP, Venus, mCherry, Tag-REP and mKate2. Fluorescent proteins, originally isolated from diverse maritime organisms, are powerful and frequently used tools in the field of molecular biology. They are generated through endogenous cellular protein synthesis and emit light after excitation with a certain wavelength, importantly, however, without the need of an additional substrate or chemical agent. Improvements of native fluorescent proteins have been achieved by optimizing their folding, expression and optical-physical properties. Newly developed fluorescent proteins showing strong and stable fluorescence are particularly suitable for detecting fusion proteins in vivo applications and upon ribosome isolation, because of the usually low amounts of total protein left after sucrose gradient separation. Alternatively Bimolecular Fluorescence complementation (BiFC) may be used, wherein the proteins of the small and large ribosomal subunits are fused to corresponding fragments of a fluorescent protein. Upon ribosome assembly, the two fragments come into close proximity, such that the fragments assemble to a functional fluorescent molecule. The N-terminal fragment usually comprises approximately two thirds and the C-terminal fragment one third of the original fluorescent protein. Ribosomes from *E. coli* strains expressing RPL19-NGFP and RPS20-CGFP fusion proteins showed green fluorescence.

In a preferred embodiment, the first fluorescent protein and the second fluorescent protein are distinguishable by fluorometric analysis. To detect both ribosomal subunits, i.e. the small and the large ribosomal subunit, simultaneously, the first and second fluorescent protein should be distinguishable by fluorometric techniques, e.g. they should emit light at distinct wavelength. Preferably, their emission maxima are at least 15 nm, more preferred at least 20 nm, most preferred at least 100 nm apart. Emission maxima of this distance allow a reliable distinction of the fluorescence signal from the first and second fluorescent protein, and enables quantification of small ribosomal subunits and large ribosomal subunits.

In a further preferred embodiment, the first fluorescent protein and the second fluorescent protein have distinct excitation wavelengths. This allows the distinct excitation of the first or second fluorescent protein e.g. by laser confocal microscopy, further increasing the accuracy of the fluorescence detection. This is particularly useful when detecting fluorescence on a cellular level.

In an alternative preferred embodiment, the first fluorescent protein and the second fluorescent protein form a Forster resonance energy transfer (FRET) pair. Fluorescent resonance energy transfer, also known as Forster resonance energy transfer (FRET) is a process in which non-radiative emitting energy of a donor molecule excites an acceptor molecule, if both are located within a specific distance. After excitation of the donor, the energy is transferred to the acceptor by dipole-dipole interactions, following the interaction law of Coulomb. Thereby, the acceptor chromophore is elevated to the excited state and can emit the energy by fluorescence. During the FRET process no photon is emitted. It is important that the excitation spectrum of the acceptor and the emission spectrum of the donor overlap in order to enable an excitation of the acceptor by donor emission energy. Besides, donor and acceptor transmissions, dipoles have to be correctly oriented to each other to allow the energy transmission. For example, the assembling of the small subunit and the large subunit of the ribosome, can be measured, if the acceptor is bound to one subunit and the donor to the other subunit. Only if both subunits form a translating 70S ribosome, acceptor and donor are close enough to undergo FRET.

In a further preferred embodiment, the first ribosomal protein and the second ribosomal protein are located within at least 10 nm when assembled in a ribosome or a ribosomal subunit. In particular, the protein of the small ribosomal subunit and the protein of the large ribosomal subunit may be located within at least 10 nm when assembled in the complete ribosome. An important variable to calculate the efficiency of a particular FRET pair, is the "first radius" ($R_0$). It describes the distance between donor and acceptor at which still 50% of the donor emission energy is transmitted to the acceptor. The distance between donor and acceptor in which FRET is possible, depends on the photo spectral properties of the two fluorophores and is in a range of about 1 to 10 nm.

In a further preferred embodiment, the first fluorescent protein and the second fluorescent protein are selected from ECFP and EYFP, EGFP and mCherry or TagGFP2 and TagRFP. With respect to an optimal Förster radius certain FRET pairs have been developed: EGFP (donor)-EYFP (acceptor) with $R_0$=5.64 nm, ECFP-EYFP with $R_0$=4.90 nm and EGFP-mCherry with $R_0$=5.24 nm. Generally, red shifted proteins are excellent FRET acceptors, because of the high excitation wavelength. mCherry is particularly preferred, because it further has a relatively high extinction coefficient and is photostable.

In a preferred embodiment, the first fusion protein comprises RPS20-mCherry (encoding sequence SEQ ID N.: 14) or RPS2-mCherry (encoding sequence SEQ ID NO.: 15) and the second fusion protein comprises RPL19-EGFP (encoding sequence SEQ ID NO.: 13), or RPL31-EGFP (encoding sequence SEQ ID NO.: 16). Combination of these specific fusion proteins resulted in the development of four different strains, in which biogenesis, assembly and degradation of ribosomal subunits and assembled ribosomes was reliably detected and monitored. The respective strains are MC4100rpsT-mcherry,rplS-egfp expressing RPS20-mCherry and RPL19-EGFP; MC4100rplS-egfp,rpsT-mcherry-kan expressing RPL19-EGFP and RPS20-mCherry (RN29; deposited at Leibniz Institute DSMZ-German Collection of Microorganisms and Cell Cultures, Braunschweig, Germany: Deposit number: DSM 27256 on May 29, 2013), MC4100rpsB-mcherry,rplS-egfp expressing RPS2-mCherry and RPL19-EGFP (RN55b; deposited at Leibniz Institute DSMZ-German Collection of Microorganisms and Cell Cultures, Braunschweig, Germany: Deposit number: DSM 27255 on May 29, 2013), and MC4100rpsB-mcherry,rpmE-egfp expressing RPS2-mCherry and RPL31-EGFP.

In a preferred embodiment, the first fusion protein comprises RPS15-mCherry (encoding sequence SEQ ID NO.: 28) and the second fusion protein comprises RPL1-mAzami (encoding SEQ ID NO.: 29). The reporter strain expressing these fusion proteins is MC4100rpsO-mCherry,rplA-mAzami (RN115).

In a preferred embodiment, the first fusion protein comprises RPS15-mCherry and the second fusion protein comprises RPS2-mAzami. Likewise, the first fusion protein may comprise RPL1-mCherry and the second fusion protein RPL19-mAzami. The respective reporter strains, MC4100rplA-mCherry,rplS-mAzami and MC4100rpsO-mCherry,rpsB-mAzami are suitable to specifically visualize the small and large ribosomal subunit, respectively.

In a preferred embodiment, the amino acid linker consists of about 5 to 10 amino acids, preferably of about 6 to 8 amino acids. The term "linker" as used herein, refers to an amino acid sequence connecting the ribosomal protein with the fluorescent protein. The linker ensures that both proteins can fold correctly without interfering with each other. Moreover, the linker provides sufficient flexibility for the ribosomal protein to be incorporated into the ribosome, thereby also ensuring the functionality of the ribosome despite the integration of the fusion protein. Moreover, the fluorescence emitted from the fluorescent protein is not impaired by interference with the ribosomal protein. To keep the ribosomal protein and the fluorescent protein in proximity while still providing sufficient flexibility for both proteins, the linker has a preferable length of 5 to 10, more preferred of 6 to 8 amino acids.

In a preferred embodiment, the amino acid linker is resistant to proteolytic digestion. This ensures that the fluorescent protein is not separated from the ribosomal protein by proteases present in the cell. Otherwise, the fluorescence signal may become disconnected from the ribosome, which might impair reliability and sensitivity of the fluorescence measurements. Linkers comprising SEQ ID NO:. 1 (Gly-Thr-Ser-Gly-Gly-Ser-Gly) or SEQ ID NO.: 2 (Gly-Ser-Gly-Ser-Gly-Ser-Gly-Gly) were found to be resistant to proteolytic digestion.

In an alternative embodiment, the amino acid linker comprises a Tev restriction site. Fusion proteins comprising fluorescent proteins forming a FRET pair are particularly suitable to monitor ribosome assembly, since a FRET signal is only generated if the two fusion proteins come into close proximity i.e. upon ribosome assembly. To control the reliability of the FRET signal, a tobacco etch virus protease restriction site (Tev site) can be integrated into the linker, such that the fluorescent protein can be deliberately separated from the ribosomal protein, which should eliminate FRET. The Tev protease cleavage site may consist of SEQ ID NO.: 3: Glu-Asn-Leu-Tyr-Phe-Gln-Gly or SEQ ID NO.: 4: Glu-Asn-Leu-Tyr-Phe-Gln-Ser. Accordingly, the linker preferably comprises SEQ ID NO.: 3 or 4.

In a preferred embodiment, the amino acids of the linker have a polar and/or small residue. Linkers containing such amino acids are particularly flexible and hardly show any interaction with the ribosomal protein, the fluorescent protein or other proteins of the ribosome upon assembly. Such amino acids include G, T, S and A.

In a further preferred embodiment, the amino acid linker is selected from the group consisting of SEQ ID NO.: 1, SEQ ID NO.: 2, SEQ ID NO.: 3 and SEQ ID NO.: 4. These linkers have been found to be particularly suitable to connect the fluorescent protein.

In a preferred embodiment, the first ribosomal protein and/or the second ribosomal protein is fused to an affinity-tag or an epitope tag. In particular, the protein of the small ribosomal subunit and/or the protein of the large ribosomal subunit may be fused to an affinity-tag or an epitope tag. Such tags can be used to isolate the fusion protein e.g. by chromatography. The term "tag" as used herein refers to a peptide sequence attached to a protein, which can be used to isolate this protein from a sample. Such tags include maltose binding protein (MBP), glutathione-S-transferase (GST), poly(his)tag, FLAG-tag, S-NYC-tag, HA-tag and MYC-tag.

In a further aspect, the invention relates to a method for identifying a compound, which interferes with ribosome biogenesis, assembly and/or degradation, comprising culturing a prokaryotic cell of the invention, measuring the fluorescence signal of the first and second fluorescent protein, adding the compound to the cell, and re-measuring the fluorescence signal of the first and second fluorescent protein, wherein a change in the fluorescence signal of the first and/or second fluorescent protein indicates that the compound interferes with ribosome biogenesis, assembly and/or degradation. When culturing a cell which expresses a first fusion protein comprising a protein of a small ribosomal subunit and a first fluorescent protein and a second fusion protein comprising a protein of a large ribosomal subunit and a second fluorescent protein, the fusion proteins become incorporated into the ribosomal subunits and finally into the mature ribosome. Accordingly, the fluorescence signal emitted from the first and second fusion protein represent the small (30S) and large (50S) ribosomal subunits, respectively. Thus, by detecting the fluorescent signal from the fusion proteins, the respective subunits as well as the assembled ribosome can be monitored. Likewise, culturing a cell, which expresses two different ribosomal proteins labeled by fusion to a fluorescent protein, each subunit can be monitored separately and in detail. The fluorescence emitted from the fusion proteins can be measured e.g. using a fluorometer or a fluorescence microscope. Importantly, using the cells of the invention, the fluorescence emitted from the fusion proteins can be measured in vivo. After establishing the cell suspension, the fluorescence signal is initially measured to monitor ribosomal biogenesis and assembly under control, e.g. physiological conditions. The measured fluorescence signal, e.g. the fluorescence intensity, serves as a reference value. Subsequently, a compound to be investigated is added to the cell suspension and the fluorescence signal re-measured. The measured signal is then compared to the fluorescence signal detected in the absence of the compound, i.e. to the reference value. An alteration in the fluorescence signal of the first and/or second fluorescent protein indicates a change in the biogenesis of the small and/or large subunits and/or in the assembly of the ribosome. For example, a disruption of the formation of the small ribosomal subunit upon addition of the compound causes a reduced fluorescence signal from the first fluorescent protein. Likewise, a defect in the biogenesis or degradation of the large ribosomal subunit causes an alteration of the fluorescence signal from the second fluorescent protein. Accordingly, a change in the fluorescence signal of the first and/or second fluorescent protein indicates that the compound interferes with ribosome biogenesis, and/or degradation. Moreover, using a first and second fluorescent protein forming a FRET pair, the assembly of the ribosome can be specifically monitored. A change in the FRET signal upon addition of the compound to the culture indicates that the small and the large ribosome subunit fail to come into close proximity and thus indicates a defect in ribosomal assembly. Therefore, the method of the invention is suitable to determine whether a given compound interferes with ribosome biogenesis, assembly and/or degradation. Likewise, the method can be used to identify a compound having such properties from a plurality of compounds, e.g. from a compound library.

In a preferred embodiment, the method further comprises culturing a second prokaryotic cell of the invention, which serves as a negative control and to which no compound is added, wherein a difference in the fluorescence intensity of the first and/or second fluorescent protein compared to the negative control indicates that the compound interferes with ribosome biogenesis, assembly and/or degradation. The second prokaryotic cell serves as a further control, since the fluorescence signal detected from this cell represents the biogenesis and assembly of the ribosome under control conditions, i.e. in the absence of the compound (negative control). This allows an endpoint analysis by methods, which are more sensitive compared to in vivo fluorescence detection. For example, the cells may be lysed and the fluorescence analyzed using a spectrofluorometer, or fluorescence micro plate reader. Upon cell lysis, the fluorescence signal is much stronger and thus allows a more sensitive detection. Likewise, the ribosomes may be isolated, and the ribosomal subunits and the assembled ribosomes separated. This provides more detailed information on the effect of the compound on biogenesis and assembly of the subunits and on ribosome formation. In addition, this preferred embodiment may be carried out without the need of elaborate in vivo imaging techniques. In combination with in vivo monitoring, however, it provides an immediate confirmation of the in vivo data increasing the accuracy and reliability of the entire method.

Figure 3:
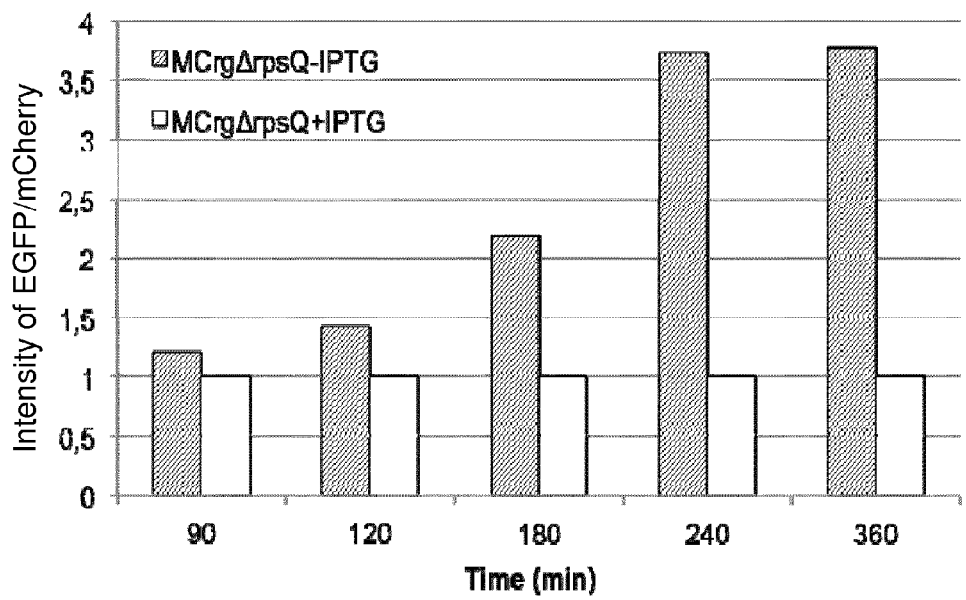
FIG. 3 shows detection of deficits in ribosome biogenesis and assembly. The ratio of the fluorescence signal of fusion proteins of the large (GFP) and small (mCherry) ribosomal subunit increased upon deletion of RPS17 (MCrgΔrpsQ, IPTG−) compared to wild-type conditions (MCrgΔrpsQ, IPTG+).

In a preferred embodiment measuring the fluorescence signal comprises calculating the quotient of the intensity of the first fluorescent protein and the intensity of the second fluorescent protein. In case the cell of the invention expresses at least two fusion proteins comprising a protein of the small and large ribosomal subunit, respectively, each ribosomal subunit (30S and 50S) is represented by one specific fluorescence signal. Therefore, the quotient of the fluorescence signals of the first and second fusion protein represents the proportion of both subunits. In cells growing under physiological conditions, the number of small ribosomal subunits and large ribosomal subunits would be expected to be identical due to the stringent control of ribosome biogenesis. However, since the different fluorescent proteins show individual fluorescence intensities the proportion of the fluorescence signal of the first and second fluorescent protein is not necessarily 1:1. Therefore, the quotient of the fluorescence intensities of the first and second fluorescent protein measured under physiological conditions may be defined as 1 and compared to the quotient of the fluorescent intensities of the first and second fluorescent protein measured after addition of the compound of interest and calculated as percentage of the reference value. Accordingly, a change in the quotient indicates a change in the proportion of small and large ribosomal subunits. For example, in case the compound inhibits the formation of the small ribosomal subunit, the fluorescence intensity of the first fluorescent protein will decrease such that the quotient of the first and second fluorescence signal will decrease as well. Likewise, in case the compound inhibits the formation of the large ribosomal subunit, the fluorescence intensity from the second fluorescent protein will decrease, such that the quotient of the intensities of the first and second fluorescent protein will increase (FIG. 3). In addition, in case the compound interferes with the biogenesis of both subunits, an overall change in fluorescence intensity will be detected, as for example in the presence of chloramphenicol. The data acquired from measuring the fluorescence signal may be processed and further calculated using KNIME software (Stöter et al. 2013).

Figure 6:
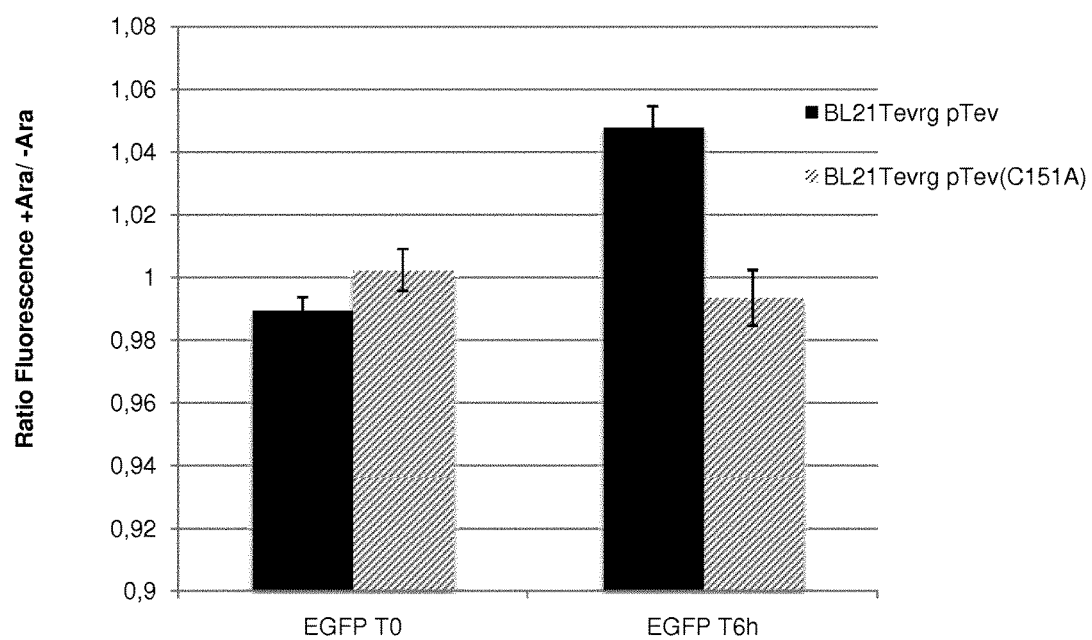
FIG. 6 shows experiments using Tev protease. $BL_{Tev}$rg cells transformed with a plasmid encoding Tev protease ($BL_{Tev}$rg pTev) and a catalytic inactive variant of Tev protease ($BL_{Tev}$rg pTevC151A) were grown to stationary phase in LB medium containing 2% Glucose. Cells were diluted with LB medium without (−Ara) and with 0.015% arabinose (+Ara) to OD 600=0.05 and transferred into wells of a 96-well plate in triplicates. Fluorescence was detected in a Tecan infinity F-500 plate reader before (T=0) and after 6 hours of incubation (T6 h). GFP fluorescence of $BL_{Tev}$rg pTev and $BL_{Tev}$rg pTevC151A in presence and absence of Ara were determined. Fluorescence values of Ara treated cells were divided by values obtained from untreated (ratios+Ara/−Ara) cells of the same strain and normalized to 1 for $BL_{Tev}$rg pTevC151A at T0 and T6 h.

In a preferred embodiment measuring the fluorescence comprises detecting a FRET signal. This is particularly preferred to detect defects in ribosome formation, since FRET takes place when the first and second fluorescent protein come into close proximity e.g. within ≤10 nm. This occurs when the subunits are assembled (in case both labeled ribosomal proteins belong to the same subunit) or when the small and large subunits form the 70S ribosome (in case the first and second ribosomal protein belong to different ribosomal subunits). Thus, a lack of FRET indicates a defect in ribosome formation. For example, although all proteins of the small and large ribosomal subunit are generated and both subunits form normally, deficiencies or the absence of one of the rRNAs can cause defects in and/or prevent assembly of the small and large subunit into a 70S ribosome. This situation can be simulated by artificially separating the fluorescent protein from the ribosomal protein e.g. by incorporating a Tev protease cleavage site into the amino acid linker and bringing the fusion protein into contact with a Tev protease (FIG. 6).

In a preferred embodiment, the fluorescence is measured during the phase of exponential growth. Bacterial growth occurs in four subsequent phases comprising the lag phase, the exponential or log phase, the stationary phase and the death phase. During the exponential phase cell growth and proliferation is optimal with the number of cells doubling per unit of time. This, however, is only possible in optimal growth conditions, in particular in the presence of sufficient nutrient supply and moderate cell density. Once exponential growth is no longer supported by the growth conditions, the culture enters the stationary phase reducing proliferation such that the overall cell number is kept constant. During the exponential phase the number of ribosomes present in the cell is highest. Accordingly, the fluorescence intensity from the fluorescent proteins is highest during this phase. Moreover, the result of any test regarding biological activity is most reliable when performed during optimal physiological conditions since this reduces the chance of alterations due to physiological adoptions of the cells to suboptimal growth conditions.

In a preferred embodiment, the fluorescence is measured for 5 to 15 hours, preferably for 8 to 12 hours, more preferred for about 10 hours. By repeatedly measuring the fluorescence for several hours, a fluorescent profile can be established. This provides detailed information on the biogenesis, assembly and degradation of ribosomes and their subunits. In addition, such a profile provides a more reliable reference for the fluorescence signals measured upon addition of the compound of interest, further improving the accuracy and the reliability of the method of the invention.

In a preferred embodiment, the fluorescence before and/or after adding the compound to the cell is measured in intervals of about 4 to 5 hours. Alternatively to high through-put screenings with endpoint analysis, large numbers of compounds and, thus, cell cultures may be analyzed by use of automated micro plate readers processing multiple 384-well plates at a time. In this case analysis in intervals of several hours can provide additional information on the time course of a compound's effect, thereby increasing the screening's reliability. For example, fluorescence may be measured just before adding a compound of interest to the cell culture ($T_0$), after about 4 hours of incubation and, once more, after 8 hours of incubation. Within this time, defects in ribosome assembly etc. will have manifested in a distinct change of fluorescence. However, in a particular preferred embodiment, the fluorescence before and/or after adding the compound to the cell is measured in intervals of 5 to 20 minutes, preferably of 10 to 15 minutes, more preferred of about 10 minutes. Such short measuring intervals are of particular advantage for investigating individual compounds, e.g. for re-investigating positive hits found in a high through-put screening. Repeatedly measuring the fluorescence signal provides more detailed information about the effect of the compound on ribosome biogenesis and formation, especially on the chronology of the interference. For example, monitoring the fluorescence signal upon the addition of the compound of interest by interval measurements provides information about the course of effect of the compound on ribosome biogenesis and assembly. Additionally, a profile of ribosome biogenesis and assembly may be established and compared to the reference profile recorded in the absence of the compound, e.g. under physiological conditions.

In a preferred embodiment, the method further comprises measuring cell density, preferably before and after adding the compound to the cell. Cell density is an expression of cell growth and proliferation. Since optimal cell growth requires high protein synthesis, cell growth and ribosome biogenesis are tightly co-regulated with increasing amounts of ribosomes produced when needed due to constant proliferation. Likewise, prokaryotic cells reduce growing or even stop dividing in case of impaired protein synthesis e.g. due to defects in ribosome biogenesis or assembly. Thus, measuring cell density provides further information as to the effect of a compound. Incorporating this step into the method of the invention, therefore, reduces the occurrence of false positive and false negative hits, thus, increasing the method's reliability.

In a preferred embodiment, the method further comprises the step of lysing the cell and re-measuring the fluorescence signal of the first and second fluorescent protein, wherein a change in the fluorescence signal of the first and/or second fluorescent protein indicates that the compound interferes with ribosome biogenesis, assembly and/or degradation. When measured in vivo, the intensity of the fluorescence signals from the fusion proteins is reduced, inter alia by the cell's organelles and, in particular, the cell wall, which absorb part of the fluorescence signal emitted from the fluorescent proteins. Moreover, the overall fluorescent signal, which can be detected from the cell suspension, is decreasing with increasing cell density. Therefore, endpoint analyses are preferred, in which cells are lysed such that the ribosomes are no longer enclosed by a cell wall improving the fluorescence signal. This leads to more sensitive and reliable results. When using lysates, a sample of cells to which no compound was should be used as a negative control.

In a further aspect, the invention relates to a method of screening a library of compounds to identify one or more members having antibiotic properties, comprising culturing a prokaryotic cell of the invention, measuring the fluorescence signal of the first and second fluorescent protein, contacting the cell with at least one compound of the library, and re-measuring the fluorescence signal of the first and second fluorescent protein, wherein a change in the fluorescence signal of the first and/or second fluorescent protein indicates that the compound has antibiotic properties. The cell of the invention is particularly suited for carrying out a high through-put screening for compounds interfering with ribosome biogenesis, assembly and/or degradation. The cells can be cultured in multi-well plates of e.g. 96- to 384-wells, such that large libraries of compounds can be screened. Such libraries may comprise small molecule compounds, phytochemical compounds or already established and approved drugs. Compounds that are identified by the method of the invention as interfering with ribosome biogenesis, assembly and/or degradation, represent potential antimicrobials/antibiotics. Several known antibiotics have a bactriostatic effect or even kill bacteria by inhibiting protein synthesis. However, all of these target protein synthesis itself i.e. elongation of the amino acid chain. For example, kirromycin and fusidic acid interfere with elongation factors and clindamycin and chloramphenicol inhibit peptidyl transferase activity. In contrast, the methods of the invention are suitable for identifying a new class of compounds targeting protein synthesis at a different molecular level, namely by inhibiting ribosome biogenesis and/or assembly. Thus, the compounds which are identified by the methods of the invention, target a different biological process compared to the established antibiotics. Therefore, they are expected to overcome the established antibiotic resistances providing a promising pharmaceutical tool to fight the increasing occurrence and spread of multiple resistant pathogens.

In a preferred embodiment, the cells are cultured in multi-well plates, preferably in 96- or 384-well plates. The cells of the invention have been shown to efficiently grow in multi-well plates. Moreover, the fluorescence signal from the cells of the invention can be detected by micro plate readers equipped with fluorometric devices. Thus, fast and efficient screenings of large sets of different compounds, e.g. substance libraries, is possible.

In a further aspect, the invention relates to a method for monitoring ribosome biogenesis, assembly and/or degradation comprising culturing prokaryotic cells of the invention and monitoring the fluorescence signal of the first and second fluorescent protein, wherein a change in the fluorescence signal indicates an alteration in ribosome biogenesis, assembly and/or degradation. The cells of the invention can also be used to observe/monitor ribosome biogenesis, assembly and/or degradation in vivo. For example, dependent on the environmental conditions, such as temperature, nutrient supply or pH value, the biogenesis and assembly as well as degradation of ribosomes may alter. To observe and follow these processes, the fluorescence signal from the cell of the invention is monitored in vivo, preferably in intervals of 5 to 20 minutes over 5 to 15 hours. Given sufficient nutrient supply and space for increasing the cell population, the monitoring may last much longer, even spanning days. This provides real time data on the biogenesis, assembly and degradation of ribosomes and their subunits, preferably under different environmental conditions or even in the presence of specific compounds.

Alternatively, the fluorescence signal may be monitored by harvesting and lysing the cells and measuring the fluorescence signal of the first and second fluorescent protein, e.g. in the cell lysate. To further analyze ribosome biogenesis in more detail, the ribosomes may be isolated from the harvested cells, e.g. by sucrose gradient centrifugation and subsequent fractionation. This allows a separation of small ribosomal subunits (30S), large ribosomal subunits (50S), 70S ribosomes and polysomes. Analyzing the fluorescence signal of the different fractions of the sucrose gradient shows that the fluorescence signal from the first and second fluorescent protein strongly correlates with the ribosomal subunit to which the ribosomal protein of the fusion protein belongs. In particular, as can be seen from FIG. 1, the fluorescence from the first fluorescent protein, when fused to a protein of the small ribosomal subunit, is detected in the fractions comprising the 30S subunit, the 70S ribosomes and the polysomes, whereas the fluorescence from the second fluorescent protein, when fused to a protein of the large ribosomal subunit, is detected in the fractions comprising the 50S subunit, the 70S ribosomes and the polysomes. Strikingly, the intensity of the fluorescence signal from the first and second fluorescent protein is almost equal in the fraction of the 70S ribosomes and the polysomes, corresponding to the fact that the ribosomes consist of one small subunit and one large subunit (FIG. 1). Accordingly, in a preferred embodiment, the monitoring comprises isolating the ribosomes and measuring the fluorescence signal of the first and second fluorescent protein in the isolated ribosomes.

In a preferred embodiment, the method may be carried out according to any of the preferred embodiments described above.

In a further aspect, the invention is directed to the use of a prokaryotic cell of the invention for detecting ribosome assembly defects in vitro.

In a further aspect, the invention is directed to the use of a prokaryotic cell of the invention for detecting and/or quantifying ribosome biogenesis, assembly and/or degradation in vitro.

In a further aspect, the invention is directed to the use of a prokaryotic cell of the invention for monitoring and/or quantifying protein translation in vitro.

In a further aspect, the invention is directed to a gene construct comprising a first element encoding a first ribosomal protein fused to a first fluorescent protein by an amino acid linker, and a second element encoding a second ribosomal protein fused to a second fluorescent protein by an amino acid linker. Preferably, the first ribosomal protein is a protein of a small ribosomal subunit and the second ribosomal protein is a protein of the large ribosomal subunit. Alternatively, the first and second ribosomal protein may be different proteins of the same ribosomal subunit, the small or the large subunit. Upon introduction of the construct into a cell, the cell produces the respective fusion proteins. Since the fusion proteins comprise functional ribosomal proteins they become incorporated into the cell's ribosomes such that the ribosomes can be detected and monitored by their fluorescence signal within the cell.

In addition, the construct may be used to provide isolated proteins of the small and large ribosomal subunit fused to a fluorescent protein, respectively. Such proteins can be employed in cell-free translation assay e.g. comprising the cell extract from *E. coli* but lacking ribosomes, amino acids and mRNA. Together with the fusion protein, non-labeled ribosomal proteins, rRNA, tRNA and mRNA are introduced into the cell-free translation assay. By detecting the fluorescent signal from the fusion proteins, translation can be monitored in real time and quantified. Since the ribosomes are assembled in the course of protein translation, the combination of small and large ribosomal subunits represents active translation. 70S formation is best detected using FRET, because FRET specifically occurs as soon as both subunits become localized together.

Accordingly, in a further aspect, the invention relates to a method for quantifying protein translation comprising providing a cell-free translation assay, adding a first fusion protein comprising a protein of a small ribosomal subunit, an amino acid linker and a first fluorescent protein, and a second fusion protein comprising a protein of a large ribosomal subunit, an amino acid linker and a second fluorescent protein, wherein the first and second fluorescent protein form a FRET pair, wherein FRET indicates the formation of a functional ribosome and, thus, translation.

Using this method, in vitro translation may be optimized e.g. by adapting environmental conditions or by adding substances, which promote the process of translation. Likewise, such in vitro assays may be used for identifying compounds inhibiting protein synthesis.

In a preferred embodiment, the method further comprises quantifying the amount of produced protein. This provides an additional readout, which can be correlated with the fluorescence signal, providing further information on translation in general and substances promoting or inhibiting protein synthesis in particular. The amount of synthesized protein may be quantified by supplying one of the amino acids as a labeled derivative, e.g. as a radioactive labeled derivative.

In a further aspect, the invention relates to a kit comprising (I) a prokaryotic cell expressing (i) a first fusion protein comprising a protein of a small ribosomal subunit, an amino acid linker and a first fluorescent protein from the endogenous gene locus of the protein of the small ribosomal subunit, and (ii) a second fusion protein comprising a protein of a large ribosomal subunit, an amino acid linker and a second fluorescent protein from the endogenous gene locus of the protein of the large ribosomal subunit, and (II) a further prokaryotic cell expressing (i) a fusion protein comprising a first ribosomal protein, an amino acid linker and a first fluorescent protein from the endogenous gene locus of the first ribosomal protein and (ii) a second fusion protein comprising a second ribosomal protein, an amino acid linker and a second fluorescent protein from the endogenous gene locus of the second ribosomal protein, wherein the first ribosomal protein and the second ribosomal protein are different ribosomal proteins of the small or large ribosomal subunit.

In a further aspect, the invention relates to a kit comprising (I) a prokaryotic cell expressing (i) a first fusion protein comprising a late assembling protein of a small ribosomal subunit, an amino acid linker and a first fluorescent protein from the endogenous gene locus of the protein of the small ribosomal subunit, and (ii) a second fusion protein comprising a late assembling protein of a large ribosomal subunit, an amino acid linker and a second fluorescent protein from the endogenous gene locus of the protein of the large ribosomal subunit, (II) a prokaryotic cell expressing (i) a first fusion protein comprising an early assembling protein of a small ribosomal subunit, an amino acid linker and a first fluorescent protein from the endogenous gene locus of the protein of the small ribosomal subunit, and (ii) a second fusion protein comprising an early assembling protein of a large ribosomal subunit, an amino acid linker and a second fluorescent protein from the endogenous gene locus of the protein of the large ribosomal subunit, (III) a prokaryotic cell expressing (i) a first fusion protein comprising a first ribosomal protein of the small ribosomal subunit, an amino acid linker and a first fluorescent protein from the endogenous gene locus of the first ribosomal protein and (ii) a second fusion protein comprising a second ribosomal protein of the small ribosomal subunit, an amino acid linker and a second fluorescent protein from the endogenous gene locus of the second ribosomal protein, and (IV) a prokaryotic cell expressing (i) a first fusion protein comprising a first ribosomal protein of the large ribosomal subunit, an amino acid linker and a first fluorescent protein from the endogenous gene locus of the first ribosomal protein and (ii) a second fusion protein comprising a second ribosomal protein of the large ribosomal subunit, an amino acid linker and a second fluorescent protein from the endogenous gene locus of the second ribosomal protein. These four reporter strains provide a tool kit to identify and characterize ribosomal subunit assembly defects both, quantitatively and qualitatively, by a combination of fluorescence-based in vivo and in vitro analyses. In particular, strains expressing late assembling ribosomal proteins of the small and large subunit (I) (e.g. MCrg: L19-EGFP; S2-mCherry) allow detection of intact portions of large and small ribosomal subunits. Comparison with unperturbed reporter strain allows identification of ribosome subunit specific assembly defects. Strains expressing early assembling ribosomal proteins of the small and large subunit (II) (e.g. MCrg*: L1mAzami; S15-mCherry) allow fluorescence based monitoring of intact subunits and intermediates of all maturation states. In vivo analysis allows determination of subunit specific turnover. Finally, the kit comprises a pair of strains expressing two different fluorescently labelled ribosomal proteins of the same subunit (e.g. MCrgL: L1-mCherry;L19-mAzami and MCrgS: S15-mCherry;S2-mAzami) with one early and one late assembly r-protein of the same subunit labelled with mCherry and mAzami, respectively. Grown in parallel, these strains allow quantification of subunit assembly defects. It is possible to analyze known ribosome-targeting antibiotics for their ability to induce assembly defects and to identify and characterize new primary inhibitors of ribosome assembly.

EXAMPLES

I. *E. coli* Expressing Fusion Proteins of Late Assembling Ribosomal Proteins of the Small and Large Ribosomal Subunit I.1 Structure Based Selection of Ribosomal Proteins for Fluorescent Protein Fusions To provide a methodology that allows monitoring protein translation in vitro and in vivo, a system was developed based on the following criteria. The method directly depicts translational activity, independently whether protein synthesis is carried out within a cell or in a cell-free assay. The read out is fluorescence-based, scalable and compatible with high throughput procedures. Quantification of translational activity is possible. To achieve these characteristics, the place of cellular protein synthesis, namely the ribosome, was directly targeted, by labeling both, the small and the large ribosomal subunit. Therefore, ribosomal proteins of the small and the large ribosomal subunit were fused to genetically encoded fluorescent proteins. Since a Fluorescence Resonance Energy Transfer (FRET) based read out should be possible, ribosomal proteins fulfilling the following requirements were selected. Within the assembled ribosome, the ribosomal proteins are localized in close proximity to the subunit interface and to each other (e.g. below 10 nm). They are exposed to the surface of the assembled ribosome, preferably with the C-terminus. In addition, ribosomal proteins were selected, that are not directly involved in protein translation or interfering with the binding of ribosome associated factors. An analysis of high-resolution structures of bacterial ribosomes of *E. coli* indicated that several ribosomal proteins fulfilled the above mentioned criteria, including RPS20, RPS 2, RPL19, RPL10 and RPL31.

I.2. Generation of Reporter Strains

I.2.1 MC4100rpsT-mcherry,rplS-egfp

Figure 4:
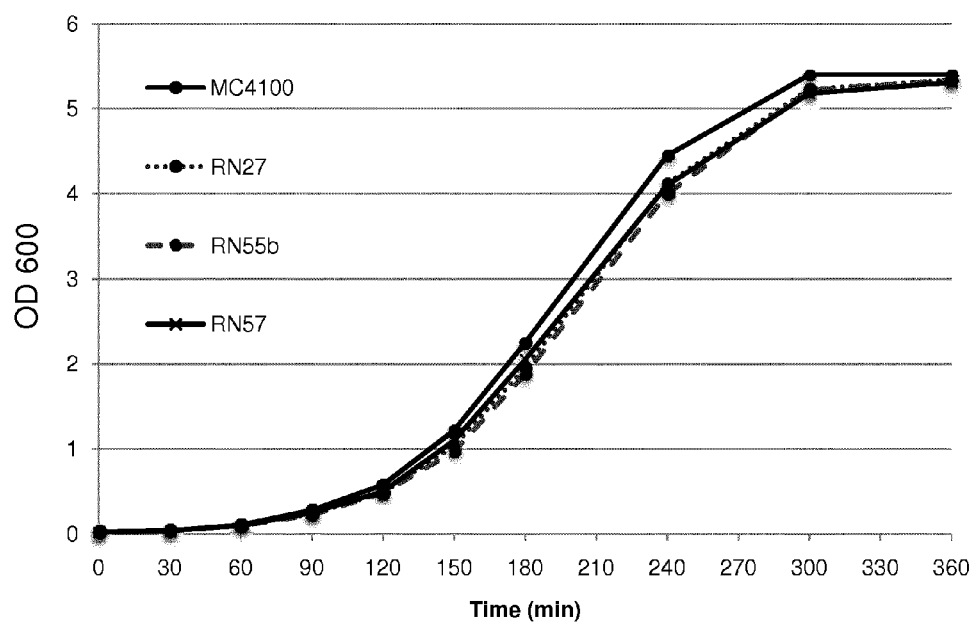
FIG. 4 shows representative growth curves of MC4100, RN27, RN55b and RN57 strains. Cells were grown at 37° C. and samples were taken every 30 min.

In a first approach MC4100 Knock-In strains were generated, harboring genomic insertions of a mcherry coding sequence in frame with rpsT and a egfp coding sequence in frame with rplS, respectively. Recombination was carried out using the lambda red technique (Datsenko and Wanner, 2000). Both strains were viable and exclusively expressed either RPS20-mCherry (MCr/RN34), or RPL19-EGFP (MCg/RN27). With the help of phage transduction, a strain harboring both knock-in constructs (MCrg) was created, expressing mCherry coupled small ribosomal subunits (SSUs) and EGFP coupled large ribosomal subunits (LSUs). Strains expressing the individual fusion proteins showed red (MCr), green (MCg), or red and green (MCrg) fluorescence. The fluorescence appeared to be cytoplasmically distributed, however, not homogeneously but accentuated, showing areas of higher and lower fluorescence intensity. Noteworthy, the distribution of red and green fluorescence was not identical, indicating that SSUs and LSUs are at least partially spatially separated, eventually for purpose of subunit biogenesis. Having obtained viable single and double knock-in strains, it was determined whether these strains behaved as the MC4100 wild-type strain. Stationary cultures of MC4100, MCr (RN34), MCg (RN27) and MCrg (RN29) cells were diluted to $OD_{600}$=0.05 and grown at 37° C. to stationary phase. Evaluation of the growth curves showed that wild-type and reporter strains had basically identical generation times. Likewise, the strains RN27, RN55b and RN57 showed growing curves comparable to that of wild type (MC4100) (FIG. 4). Thus, the modified ribosomes of the reporter strains operated as good as their wild-type counterparts, at least under optimal growth conditions. Therefore, growth behavior was further tested in spot tests under various stress conditions, e.g. heat (42° C., 37° C., 30° C.), osmotic stress (in the presence of 0.5 M NaCl) and translational stress (in the presence of Chloramphenicol). It turned out that both, wild-type and reporter strains, performed similarly under these conditions, demonstrating that the ribosomal fusion proteins do not have any inhibitory influence on ribosome activity. In particular, the reporter strains did not show any growth defect at low temperature, which is known to indicate ribosomal assembly defects. In addition, cell lysates and ribosomes isolated using sucrose cushion centrifugation, were analyzed by SDS-PAGE. This revealed that ribosomes of all mutant strains contained additional Coomassie-stained protein bands. While ribosomes of MCr (RN24) showed an additional protein band migrating at 40 kDa, the ones of MCg (RN27) contained a 45 kDa band, corresponding to the calculated molecular weights of RPS20-mCherry and RPL19-EGFP, respectively. MCrg (RN29) ribosomes contained both extra bands. This clearly shows that the ribosomal fusion proteins of the individual strains are incorporated in the ribosomes. Finally, ribosomes of MC4100 and MCrg were analyzed by sucrose gradient centrifugation and subsequent polysome analysis. The ribosome profiles obtained from both strains did not show any apparent difference, indicating that the reporter strains have wild-type like amounts of 30S, 50S, 70S ribosomes and polysomes. Taken together, physiological and biochemical characterization showed that the reporter strains and their ribosomes are basically indistinguishable from their wild-type counterparts in each category tested.

I.2.2 Generated Reporter Strains

Using the above describes techniques various reporter strains were generated and tested with respect to cell viability and fluorescence signal:

| strain | fusion proteins | referred to as |
|---|---|---|
| MC4100 -rpsT-mcherry-kan | RPS20-mCherry | MCr/RN34 |
| MC4100 rpsB-egfp | RPS2-EGFP | RN56b |
| MC4100 -rpsB-mcherry | RPS2-mCherry | RN57 |
| MC4100 rpmE-egfp, rpsB-mcherry | RPL31-EGFP RPS2-mCherry | RN72 |
| MC4100 rplS-egfp, rpsT-Tev-mcherry | RPL19-EGFP RPS20-Tev-mCherry | RN45/MC$_{Tev}$rg |
| MC4100 rplS-egfp, rpsT-mcherry-kan | RPL19-EGFP RPS20-mCherry | RN29 |
| MC4100 rplS-egfp, rpsT-mcherry | RPL19-EGFP RPS20-mCherry | RN50/MCrg/MC-RG1 |
| MC4100 rplS-egfp, rpsB-mcherry, rpsQ::kanR | RPL19-EGFP RPS2-mCherry | RN88/MCrgΔ |
| MC4100 rplS-egfp, rpsB-mcherry | RPL19-EGFP RPS2-mCherry | RN55b/MC-RG2 |
| MC4100 rplS-egfp | RPL19-EGFP | RN27/MCg |
| MC4100 rplS-ecfp, rpsT-eyfp-kanR | RPL19-ECFP RPS20-EYFP | RN53/MCyc |
| BL21rplS-egfp, rpsT-Tev-mcherry | RPL19-EGFP RPS20-Tev-mCherry | RN46/BL$_{Tev}$rg |
| BL21rplS-egfp, rpsT-mcherry | RPL19-EGFP RPS20-mCherry | RN81/BLrg |
| BL21rplS-ecfp, rpsT-eyfp | RPL19-ECFP RPS20- EYFP | BLyc |
| MC4100rpsT-eyfp-kan | RPS20-EYFP | MCy/RN12 |
| MC4100rplS-ecfp-kan | RPL19-ECFP | MCc/RN49 |
| MC4100rpsO-mcherry | RPS15-mCherry | MCr*/RN93.1 |
| MC4100rplA-mazami | RPL1-mAzami | MCg*/RN119.1 |
| MC4100rpsO-mcherry, rplA-mazami | RPS15-mCherry RPL1-mAzami | MCrg*/RN115 |
| MC4100rpsO-mcherry, rplA-mazami, rpsQ::kanR | RPS15-mCherry RPL1-mAzami | MCrg*ΔsQ/RN116 |
| MC4100rpsO-mcherry, rplA-mazami, rplC::kanR | RPS15-mCherry RPL1-mAzami | MCrg*ΔsC/RN117 |
| MC4100rplA-mcherry, rplS-mazami | RPL1-mCherry RPL19-mAzami | MCrgL/RN120.1 |
| MC4100rpsO-mcherry, rpsB-mazami | RPS15-mCherry RPS2-mAzami | MCrgS/RN121.1 |
| MC4100rplA-mcherry, rplS-mazami, rpsQ::kanR | RPL1-mCherry RPL19-mAzami | MCrgLΔsQ/RN124 |
| MC4100rplA-mcherry,rplS-mazami, rplC::kanR | RPL1-mCherry RPL19-mAzami | MCrgLΔIC/RN125 |
| MC4100rpsO-mcherry, rpsB-mazami, rpsQ::kanR | RPS15-mCherry RPS2-mAzami | MCrgSΔsQ/RN122 |
| MC4100rpsO-mcherry, rpsB-mazami, rplC::kanR | RPS15-mCherry RPS2-mAzami | MCrgSΔIC/RN123 |

For amplification of ribosomal protein genes the following primers were used

| | | | |
|---|---|---|---|
| rplS | Forward #1580 | gagcgtactggtaaggctgctcgtatcaaagagcgtcttaac GGATCCggttctggctctggtgg | SEQ ID NO.: 5 |
| | Reverse #1581 | ttggccagcccttcttaacaggatgtcgcttaagcga-aatcGTGTAGGCTGGAGCTGCTTC | SEQ ID NO.: 6 |
| rpsT | forward #1578 | gtcataaggctaacctgactgcacagatcaaca-aactggctGGGACGTCGGGTGGAAGC | SEQ ID NO.: 7 |
| | Reverse #1579 | GCTTGCGCGGGCTTTTTCACAAAGCTT-CAGCAAATTGGCGAatgaatatcctccttagttc | SEQ ID NO.: 8 |
| rpsB | Forward #1987 | tctggcttcccaggcggaagaaagcttcgtagaagct-gagGGGACGTCGGGTGGAAGC | SEQ ID NO.: 9 |
| | Reverse #1988 | tctgcaactcgaactatttttggggagttatcaagcct-taATGAATATCCTCCTTAGTTC | SEQ ID NO.: 10 |
| rpmE | Forward #1984 | tgaccgcttcaacaagcgtttcaacatcccgggcag-caaaGGGACGTCGGGTGGAAGC | SEQ ID NO.: 11 |
| | Reverse #1351 | AAAAAGCGCCGTGCGGCGCTTTTTTCG GAAATCCGGTCATGAATATCCTCCTTAGT | SEQ ID NO.: 12 |
| rpsO | Forward #1348 | acgttacacccagctcatcgagcgcctgggtctgcgtcgcGG-GACGTCGGGTGGAAGC | SEQ ID NO.: 24 |
| | Reverse #1466 | agggccactcaggccccctttttctgaaactcgcaagaaAT-GAATATCCTCCTTAGTTC | SEQ ID NO.: 25 |

| | | | |
|---|---|---|---|
| rplA | Forward #2460 | atgggtgcaggtgttgcagttgaccaggctggcctgagcgcttctgt aaacGGGACGTCGGGTGGAAGC | SEQ ID NO.: 26 |
| | Reverse #2461 | aagcattatacgtgggggtaagattgtagacaaaatcaccgccca cgtaaaggcaATGAATATCCTCCTTAGTTC | SEQ ID NO.: 27 |

I.3. 70S-Specific FRET Signal in EGFP and mCherry Labeled Ribosomes

Figure 5:
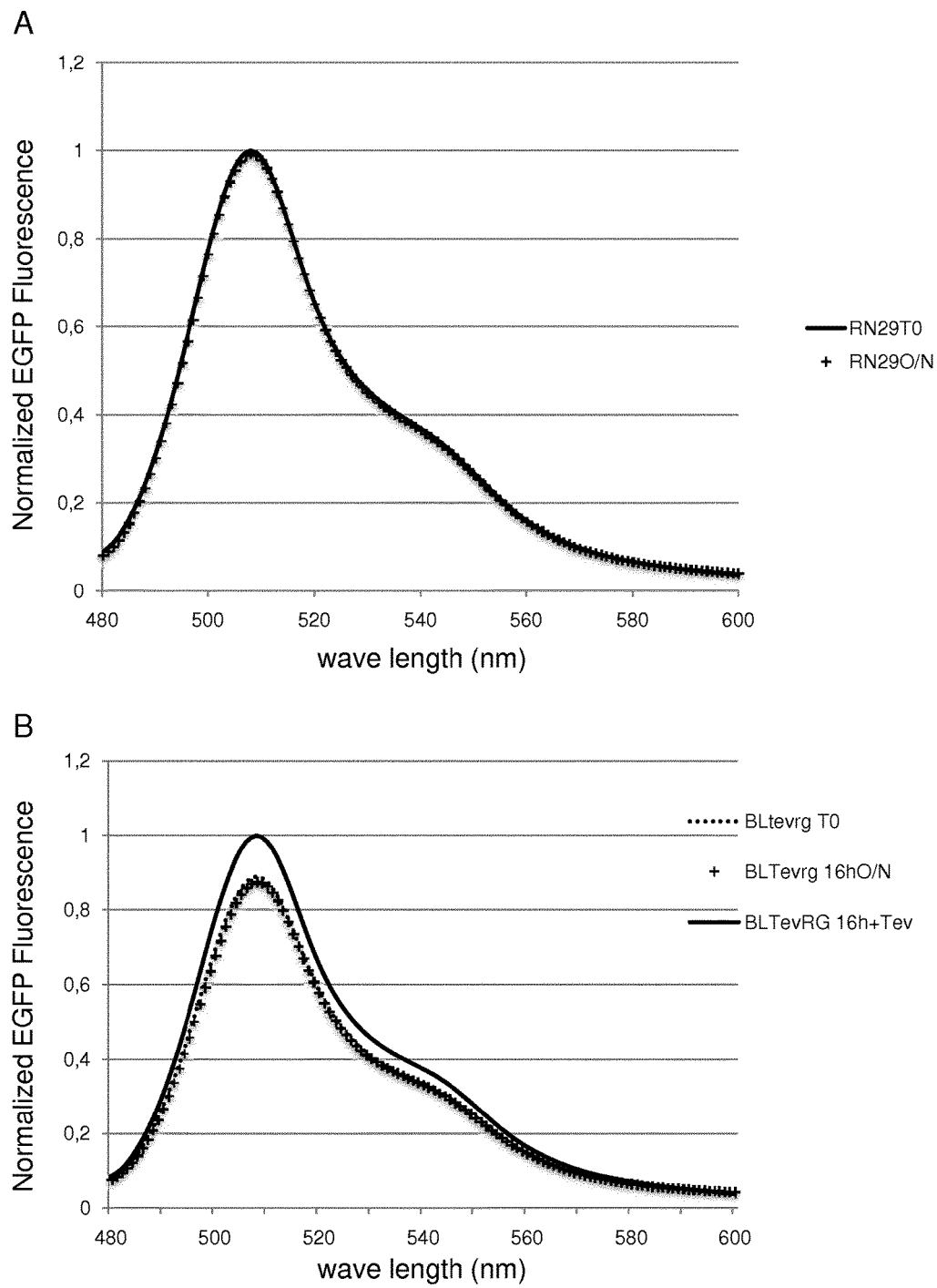
FIG. 5 shows fluorescence spectra recorded from ribosomes of RN29 cells (A) and $BL_{Tev}$rg cells (B) incubated for 16 h at 4° C. in presence and absence of Tev protease at T0 and after 16 h (B).

I.3.1 In Vitro Detection of FRET Using Tev Protease Mediated Acceptor Detachment To make use of fluorescent ribosomes in a classical expression strain, the genetic elements encoding the fusion proteins RPS20-mCherry and RPL19-EGFP were transferred into a BL21 background. After confirming that the mutant strains showed functional protein synthesis, it was determined whether FRET signal can be detected from functional (or even operating) ribosomes. Towards this, a strain containing a tobacco etch virus (Tev) protease cleavage site in between RPS20 and mCherry ($BL_{Tev}$rg/RN46) was designed. This allowed the removal of the acceptor (mCherry) from the ribosome in a timely controllable fashion, such that, in case of FRET, the donor quench reverts and leads to an increase in GFP fluorescence. First, fluorescent ribosomes from $BL_{Tev}$rg were isolated by sucrose cushion centrifugation. The ribosomes (15 pmol) were diluted in reaction buffer and incubated for 16 h at 4° C. in the presence and absence of Tev protease. Before and after incubation, fluorescence emission spectra were collected, showing an increased fluorescence intensity of EGFP after incubation with Tev protease, indicating that after removal of mCherry from the ribosome, FRET did no longer occur. Ribosomes derived from $BL_{Tev}$rg were analyzed before (T0) and after (T16 h) incubation with and without Tev protease (FIG. 5 B). As a control RN29 cells were analyzed before and after addition of Tev (FIG. 5 A). In this case, since the fusion proteins were lacking a Tev cleavage site, the addition of Tev did not affect the fluorescence spectra. Immunoblot analysis of the isolated ribosomes confirmed that only Tev-site containing ribosomes were processed by Tev protease.

I.3.2 In Vivo Detection of FRET Using Tev Protease Mediated Acceptor Detachment

Figure 7:
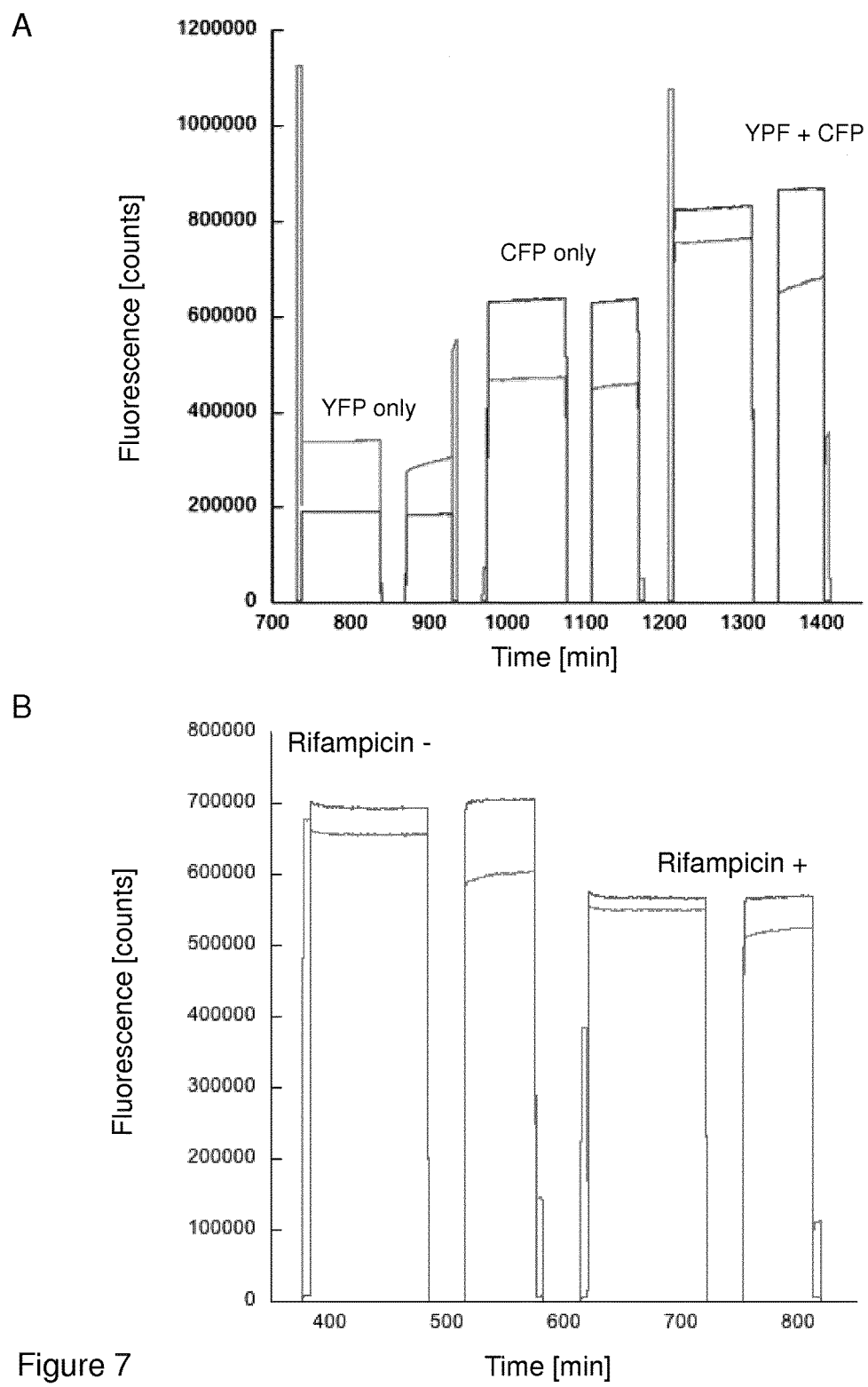
FIG. 7 shows detection of FRET signal in vivo. Stationary cultures of MCy, MCc and MCyc cells were diluted to OD600=0.05 and incubated for 1.5 h at 37° C. Cells were immobilized on the bottom of wells of a 96-well plate (A). All three cell types were analyzed according to the same scheme: 1) yellow and cyan fluorescence was detected simultaneously. 2) Cells were treated with laser light of a wavelength specifically destroying EYFP fluorophores (=bleaching). 3) Yellow and cyan fluorescence was detected simultaneously and changes in the donor (=CFP) fluorescence were determined. FRET efficiency was calculated. In addition, MCyc cells were diluted 1 to 10 and incubated in absence (-Rifampicin) and presence of Rifampicin for 45 min at 37° C. (B). Cells were immobilized on the bottom of wells of a 96-well plate. Cells were analyzed as in (A) and FRET efficiency was calculated.

To determine, whether Tev protease mediated removal of the acceptor mCherry from its position on the small ribosomal subunit is also achievable in vivo, two arabinose inducible vectors encoding wild-type Tev protease and a catalytic inactive variant (TevC151A) were cloned. $BL_{Tev}$rg was transformed with the plasmids pTev and pTevC151A. Stationary cultures of both strains were diluted and transferred to 96-well format in triplicates in the presence and absence of arabinose and analyzed in a Infinite 500 plate reader (Tecan, Männedorf, Switzerland). Before (T0) and after 6 hours (T6 h) of incubation at 30° C. EGFP specific fluorescence intensities were detected and ratios between arabinose induced and non-induced samples were calculated for Tev and Tev C151A expressing cells (FIG. 6). The normalized presentation reveals that expression of Tev protease resulted in a more than 5% stronger EGFP signal than expression of the catalytic inactive variant TevC151A. Additional experiments demonstrated that Tev and TevC151A were produced at same levels upon induction and presence of Tev led to RPS20-Tev-mCherry cleavage, while presence of TevC151A did not. This demonstrates that specific removal of the acceptor mCherry in $BL_{Tev}$rg cells leads to an increase in donor fluorescence, indicating that FRET takes place in vivo. In order to obtain quantitative evidence for FRET in vivo a fluorescence microscope-based in vivo method was used to analyze the reporter strains. For this, further reporter strains were constructed carrying chromosomal knock-ins leading to the production of RPL19-ECFP, RPS20-EYFP, or both. These strains (MCc, MCy, MCyc) performed like the previously tested reporter strains in phenotypic and biochemical characterization. Exponentially growing cells were immobilized on the poly-L-lysine coated glass surface of wells of a 96-well plate and analyzed by acceptor photo-bleaching. A FRET efficiency of 3.8% was calculated. Control experiments using MCc and MCy revealed no FRET (FIG. 7 A). To show that the extend of FRET obtained was due to translating ribosomes, MCyc cells were prepared again and incubated in the absence and presence of the RNA polymerase inhibiting drug Rifampicin. In the presence of Rifampicin transcription is blocked and the majority of cellular mRNA is degraded within minutes. While FRET analysis of the untreated sample resulted in 1.3% FRET, the sample treated with Rifampicin did not exhibit FRET (FIG. 7 B), indicating that the appearance of FRET correlates with translational activity. In summary, the experiments demonstrate that FRET is observed in reporter strains only if i) both fusion proteins are localized to their designated ribosomal positions (i.e. RPL19 and RPS20); and ii) 70S ribosomes are formed in the course of protein translation. Further, FRET signal depends on the correct localization of the fusion proteins within the ribosome. This has been demonstrated in vitro and in vivo using reporter strains harboring different combinations of fluorescent proteins (EGFP/mCherry vs. ECFP/EYFP) and using different methods (fluorescence plate reader vs. fluorescence microscope).

Figure 8:
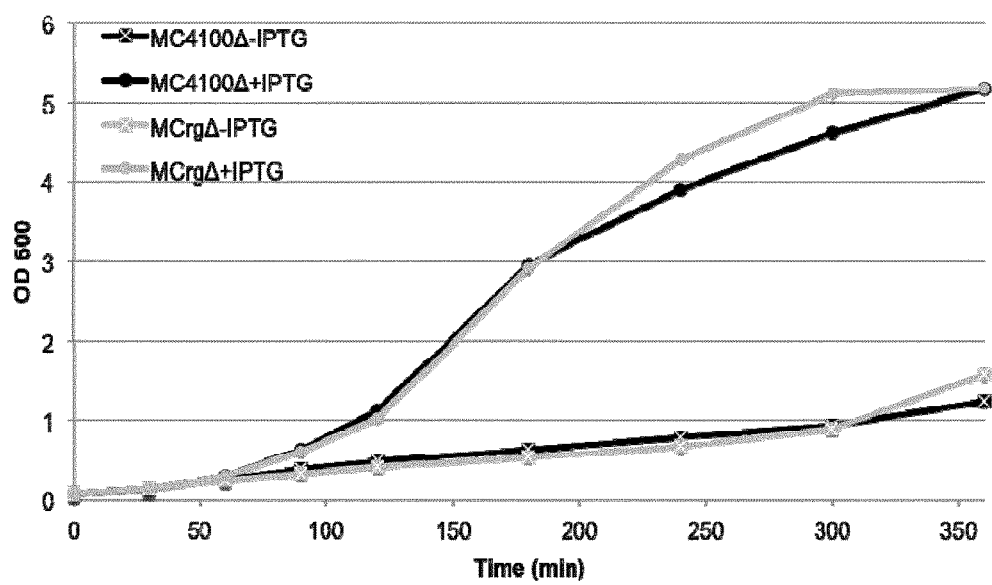
FIG. 8 shows growth curves of conditional rpsQ-Knock-Out cells (MC4100ΔrpsQ und MCrg ΔrpsQ) in the presence and absence of IPTG. In the absence of IPTG, the cells fail to produce RPS17, and show poor growth behavior.
Figure 9:
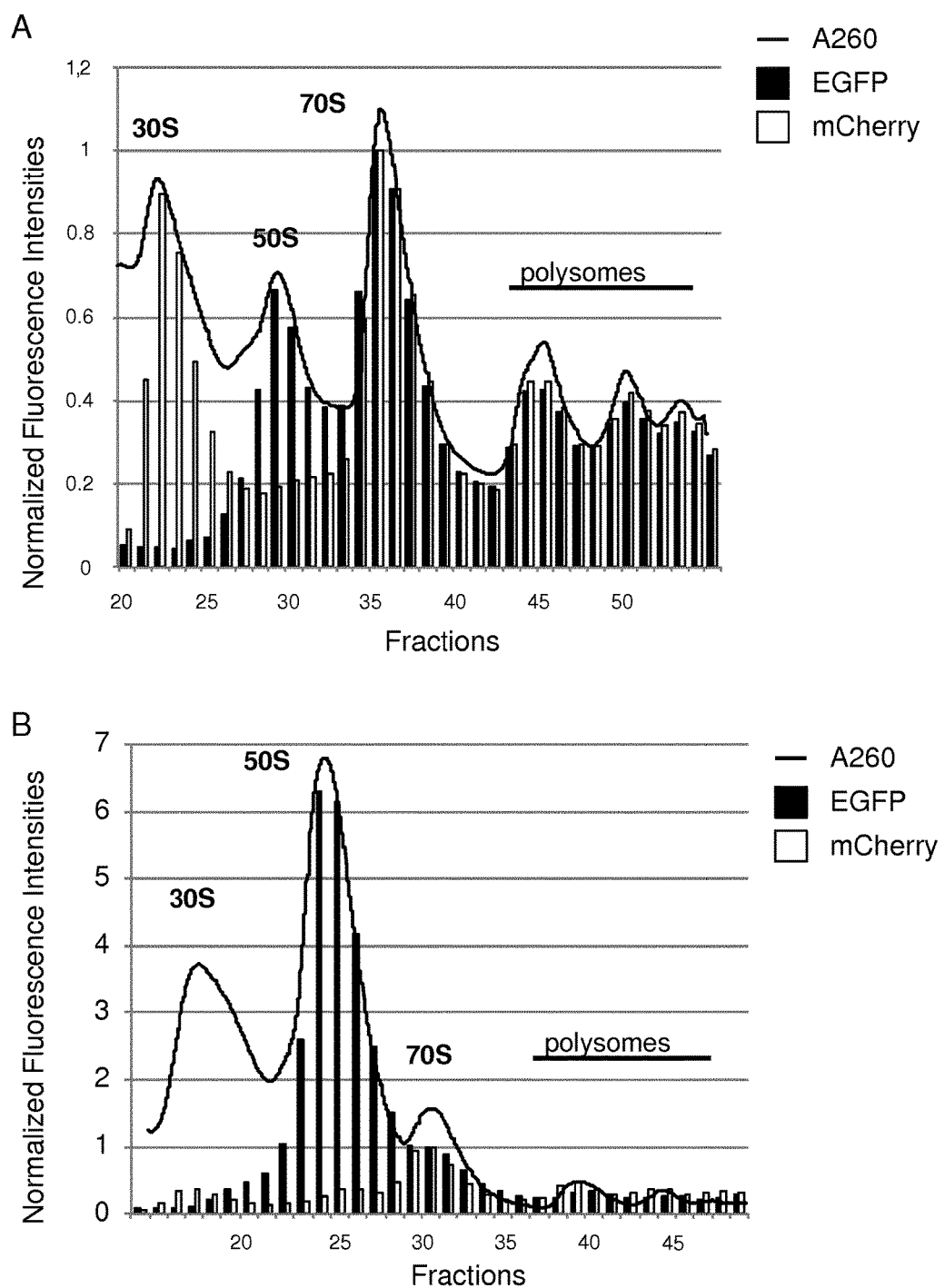
FIG. 9 shows a ribosome profile and fluorescence analysis of sucrose gradient fractions obtained from RN88 cells grown in the presence (A) and absence (B) of IPTG. In the presence of IPTG, the profile is very similar to the one obtained from RN55b (compare FIG. 1), indicating that ectopic expression of rpsQ was sufficient to complement the gene knock-out. The absence of IPTG, in contrast, leads to a reduction of the rpsQ level, which causes severe problems in the biogenesis process of the small ribosomal subunit. The high amounts of 30S particles reflect a species that is obviously defective as indicated by the low amounts of 70S ribosomes and polysomes.

I.4. Use of Reporter Strain RN55b for Detecting Defects in Ribosome Biogenesis and Assembly To prove that strain RN55b is capable of indicating ribosomal subunit biogenesis, a reporter strain was developed lacking RPS17 (RN88), which shows severe growth impairment. RPS17 is an essential ribosomal protein and known to bind rRNA and to interact with early precursors of the small ribosomal subunit. In addition, an Isopropyl-β-D-thiogalactopyranosid (IPTG) inducible vector with wild-type rpsQ was introduced into RN88 cells, such that a wild-type phenotype could be induced by supplement of IPTG. RN88 cells were grown in LB at 37° C. in presence and absence of the inductor IPTG. OD600 values, EGFP and mCherry fluorescence were measured, showing that RN88 displays similar growth behavior as the MC4100 wild-type strain when cultured in the presence of IPTG. However, in the absence of IPTG, growth is significantly reduced as a result of the lack of RPS17 (FIG. 8). Fluorescence analyses showed that as a result of interfering with the biogenesis of the small ribosomal subunit (by conditional knock-out of rpsQ—in the absence of IPTG) the EGFP/mCherry ratio raises significantly, i.e. by a factor of 3.7 (see FIG. 3). This indicates that the generation of the small ribosomal subunit is impaired by the lack of RPS17, while the generation of large ribosomal subunits remains intact. Additionally, cells were grown in LB at 37° C. in the presence and absence of the inductor IPTG, lysed and ribosomes were separated using sucrose gradient centrifugation and fractionation. From these, ribosome profiles were obtained by A260 determination of the sucrose gradient centrifugate and by fluorescent analysis after fractionation. This confirmed that in the absence of RPS17 biogenesis of the small ribosomal subunit is disturbed, with the amount of intact 30S subunit and 70S ribosomes reduced compared to 50S subunits (FIG. 9). In summary, the results demonstrate that the reporter strain RN55b is suitable for detecting defects in ribosome biogenesis and assembly.

I.5. Cultivation of Cells in Multi-well Plates

I.5.1 Optical Density and Fluorescence Time Course Measurements

For the detection of ribosome biogenesis and assembly to be compatible with screening requirements, cells need to grow in multi-well plates. Therefore, cells were transferred to a 96-well plate and incubated in a Infinite F500 plate reader at 30° C. for eight hours. The device is compatible with long-term incubation of cell suspensions. Every 10 minutes, the plate was shaken and A650 (indicating cell density), EGFP fluorescence and mCherry fluorescence were detected in an automated fashion. A650 values increased and reached a plateau after 6 hours, showing that reporter cells grow reliably in 96-well plates. Likewise EGFP and mCherry fluorescence intensities could be reliably measured in the multi-well plate system.

I.5.2 Quantification of Large and Small Ribosomal Subunits

Figure 10:
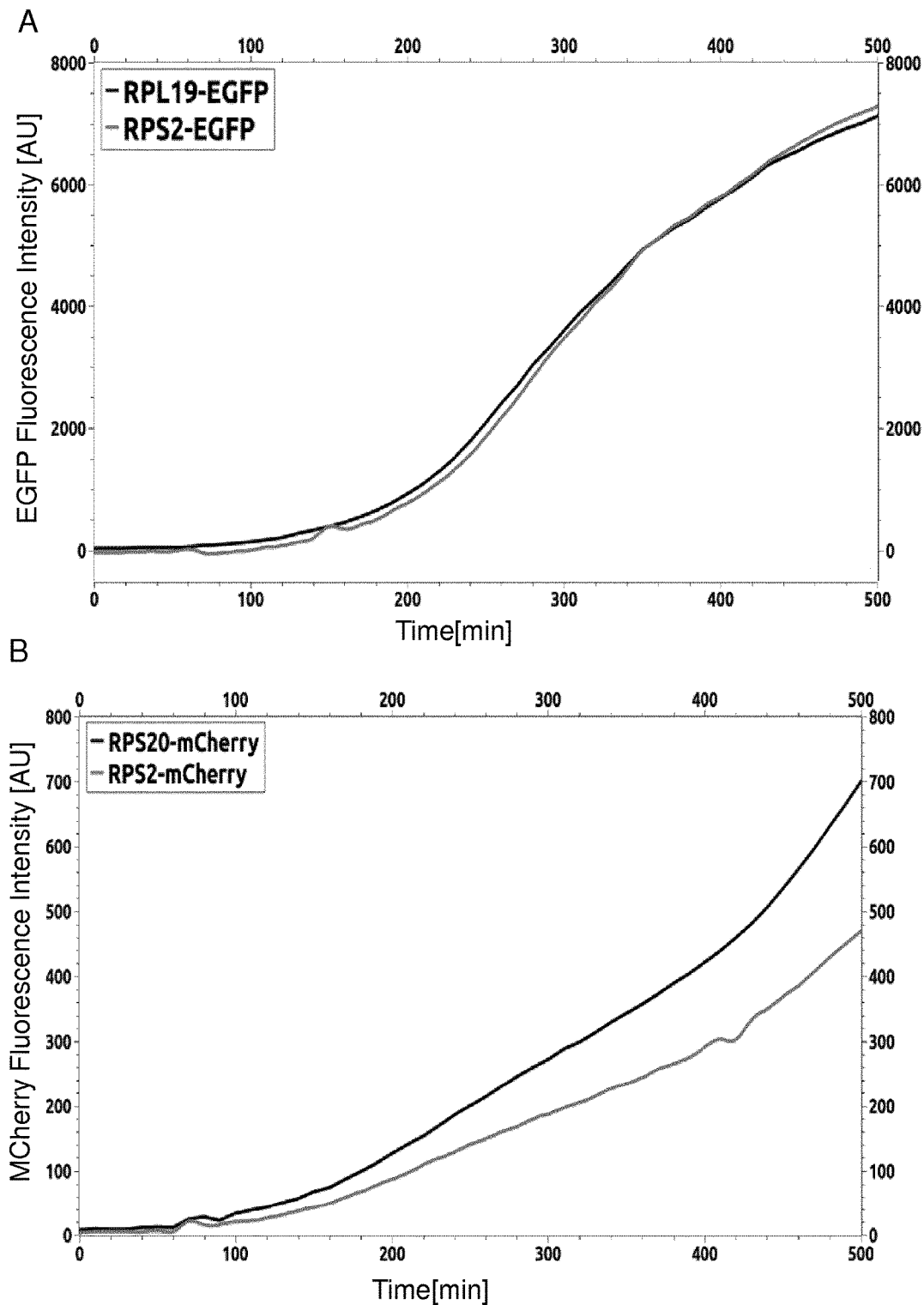
FIG. 10 shows fluorescent signals recorded from different ribosomal fusion proteins for comparison.

Since the amount of a ribosomal protein represents the abundance of the subunit it belongs to, the fluorescence intensity of the fusion protein reflects the quantity of the corresponding subunit. The recording of EGFP and mCherry specific fluorescence intensities over time, however, resulted in curves with different shapes. While EGFP signals produced a sigmoid curve, mCherry signals resulted in a hyperbolic curve. To test whether this was because the ribosomal subunits were produced with different speed and/or in different amounts or because of differences in the photo-spectral properties of the fluorescent proteins, a further knock-in strain expressing RPS2-EGFP (MC-G1/RN56b) was generated and compared to a strain expressing RPL19-EGFP (RN27) (FIG. 10 A). This revealed that the fluorescence signal from both strains is almost identical, suggesting that cellular amounts of RPL19 and RPS2 do not differ. Similar results were obtained with strains expressing RPS2-mCherry and RPS20-mCherry fusion proteins (RN57 and RN34) (FIG. 10 B).

I.5.3 Detection of Ribosome Assembly Defects

Monitoring biogenesis and assembly of ribosomal subunits also allows the detection of abnormalities in ribosome biogenesis and assembly processes. To demonstrate this, cells were treated with antibiotics that are known to have secondary effects on ribosome biogenesis/assembly as e.g. chloramphenicol. Chloramphenicol primarily binds to the large subunit and thereby inhibits the peptidyl transfer reaction. Alongside a resulting shut-down of protein synthesis, accumulating precursor particles of both ribosomal subunits have been observed. Therefore, treatment of cells with chloramphenicol causes precursor accumulation and assembly defects of ribosomal subunits. E. coli MC4100 and MC-RG1 cells were transferred to 96-well plates and incubated at 30° C. in a plate reader. After one hour, wild-type and reporter cells were treated with increasing amounts of chloramphenicol and incubation was continued for another six more hours. A650 values, EGFP and mCherry specific fluorescence intensities were automatically detected. In the absence of chloramphenicol, the growth curve of the reporter strain reached a maximum A650 of 0.5. In the presence of chloramphenicol, in contrast, a dosedependent reduction of cell growth was detected. At concentrations higher than 15.5 µM cells did not grow any further. Similarly, EGFP and mCherry fluorescence decreased with increasing concentrations of chloramphenicol. Similar results were obtained using the reporter strain MC-RG2 (RN55b) expressing L19-EGFP and S2-mCherry fusion proteins. This shows that fusion proteins comprising ribosomal proteins and fluorescent proteins are suitable to detect alterations in ribosome biogenesis and assembly. In addition, defects in ribosome biogenesis and assembly were traced using a genetic approach. Several cofactors are known to play a role in ribosome biogenesis and their knock-outs and/or ectopic expression causes defects in ribosomal subunit assembly. A possible candidate is the gene ygdP (alternatively rppH or nudH). Knock-outs of this gene have been described to result in increased amounts of 30S, decreased amounts of 50S subunits and reduced levels of 70S ribosomes compared to wild-type strains (Jiang et al., 2007). In vivo fluorescence recordings of the E. coli MC4100rp/S-egfp,rpsB-mcherry-ΔygdP cells growing in 96-well plates were performed and fluorescent signals measured. EGFP/mCherry fluorescence intensity ratios differed clearly when comparing MC4100rp/S-egfp,rpsB-mcherry (RN55b) with MC4100rplS-egfp,rpsB-mcherry-ΔygdP reporter strains. The fluorescence ratio curve of the knock-out strain exhibited an angular point that shows up later (after approx. 380 vs. 250 minutes) and was far below the maximum of the wild-type reporter strain. The overall decreased EGFP/mCherry fluorescence ratio values of the knock-out strain compared to the RN55b reporter strain are caused by proportional lower EGFP fluorescence intensities. In summary, fluorescence recordings of reporter strains are suitable to detect changes in the level of ribosomal subunits, e.g. due to biogenesis defects.

I.5.4 Expansion of the Reporter System to High-Throughput

Figure 11:
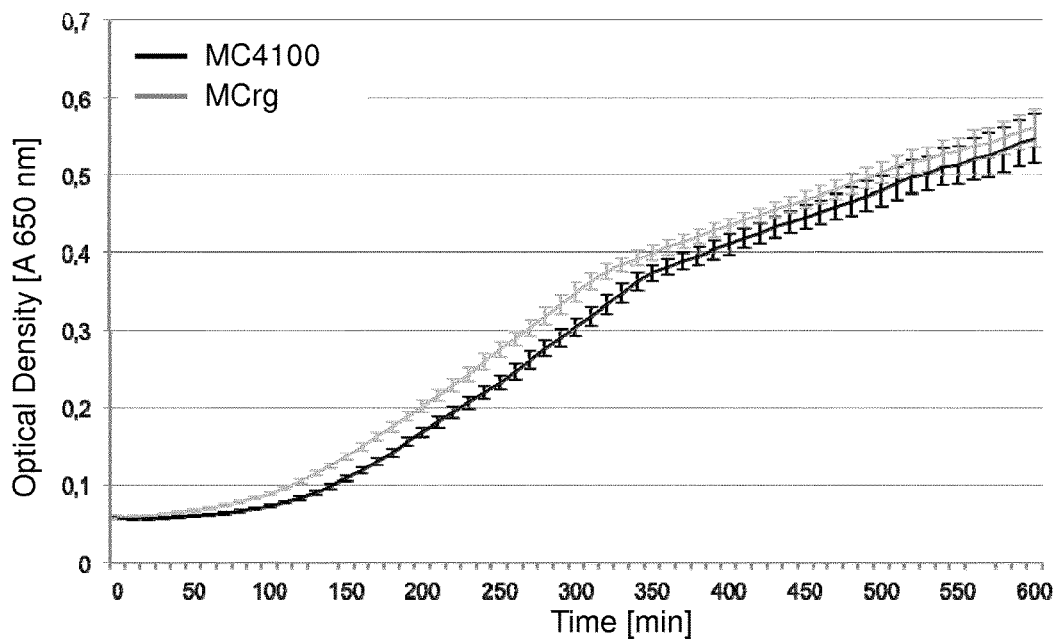
FIG. 11 shows optical density (A) of MC4100 wild-type and the MCrg reporter strain suspensions and fluorescence (B) measurements taken from the MCrg reporter strain in 384 well plates. Fluorescence intensity curves are background corrected using MC4100 wild-type cells. Error bars indicate standard deviation.
Figure 11:
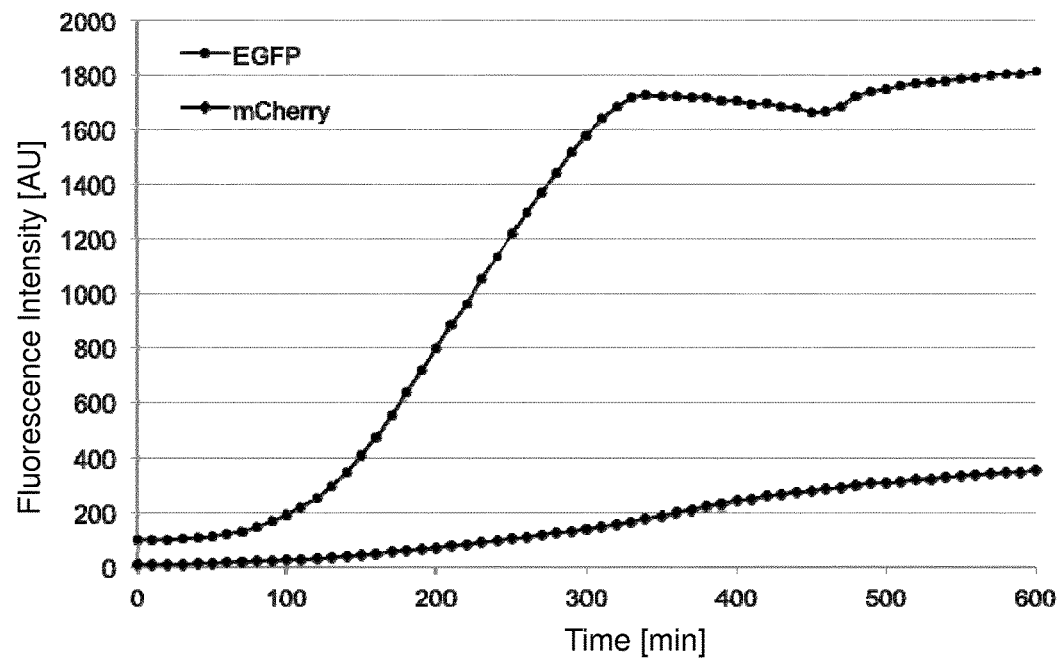

Chemical compound libraries are often provided in 384-well plates. Therefore, it was determined whether E. coli reporter cells can be cultures in 384-well plates and still allow reliable recordings of their EGFP/mCherry fluorescence intensities. A pipetting robot of the type FreedomEvo (Tecan, Männedorf, Switzerland) was programmed to manage the automated loading of the multi-well plates with wild-type and reporter cells. 50 µl E. coli MC4100 wild-type and 50 µl MCrg reporter cells were transferred into the 384-wells and incubated in the Infinite 500 fluorescence plate reader. A650 values and fluorescence intensities were detected, showing that the reporter cells can be cultured and monitored in 384 well plates in a fully automated fashion, thus, fulfilling common high-throughput screening requirements (FIG. 11).

II. E. coli Expressing Fusion Proteins of Early Assembling Ribosomal Proteins of the Small and Large Ribosomal Subunit In order to generate a reporter strain to monitor ribosome assembly landscapes, ribosomal protein candidates from each subunit were selected by the following parameters: i) distant from functional sites, ii) accessible to C-terminal tagging with fluorescent proteins, iii) early assembly proteins and iv) subject of feedback regulation. The ribosomal proteins S15 and L1 fulfill all these criteria: Their surface exposed C-termini allow convenient tagging (with mCherry and mAzami). Even though they are not essential, growth would be severely hampered if the fusion proteins do not fully complement the wild type protein's function. According to in vivo ribosome assembly maps, both are early assembly proteins and consequently present in ribosomal particles of each state of maturation. In addition feedback regulation by autogenous control ensures they are not produced in excess.

II.1. Physiological and Biochemical Characterization of the Engineered Strains

Figure 12:
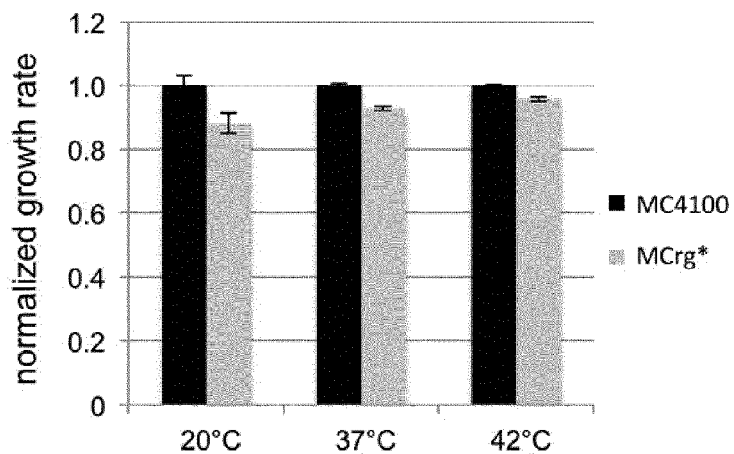
FIG. 12 shows physiological and biochemical characterization. (A) Cells as indicated were grown at 20, 37 and 42° C. to stationary phase. Growth rates were calculated and normalized values are given for each strain at each incubation temperature, N=3. (B) Ribosomes from the indicated strains were isolated by sucrose cushion centrifugation and subjected to western blot analysis using S15 and L1 specific antisera. Asterisks denote unspecific protein bands.
Figure 12:
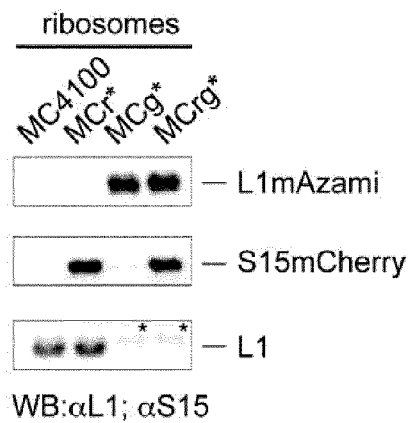

To exclude that tagging of r-proteins with FPs interferes with regular cell functions and growth, the reporter strains MCr* (RN93.1) and MCg* (RN119.1) were analyzed in more detail. Spot tests revealed that growth of the genetically engineered strains did not differ from that of the wild type strain at various temperatures (FIG. 12). Likewise growth rate of MCrg* at 37° C. was within the range of the wild type strain (FIG. 12A). Next, the protein content of MCr*, MCg* and MCrg* (RN115)-derived ribosomes was analyzed by SDS-PAGE and immunoblotting (FIG. 12B). While MCr* and MCg* ribosomes contained one fusion protein (migrating at 37 and 57 kDa, respectively), two fusion proteins were observed in MCrg* ribosomes. Collectively, the data indicate that growth behavior and functional competence of the ribosomes of MCrg* are similar to those of the parental strain.

Figure 13:
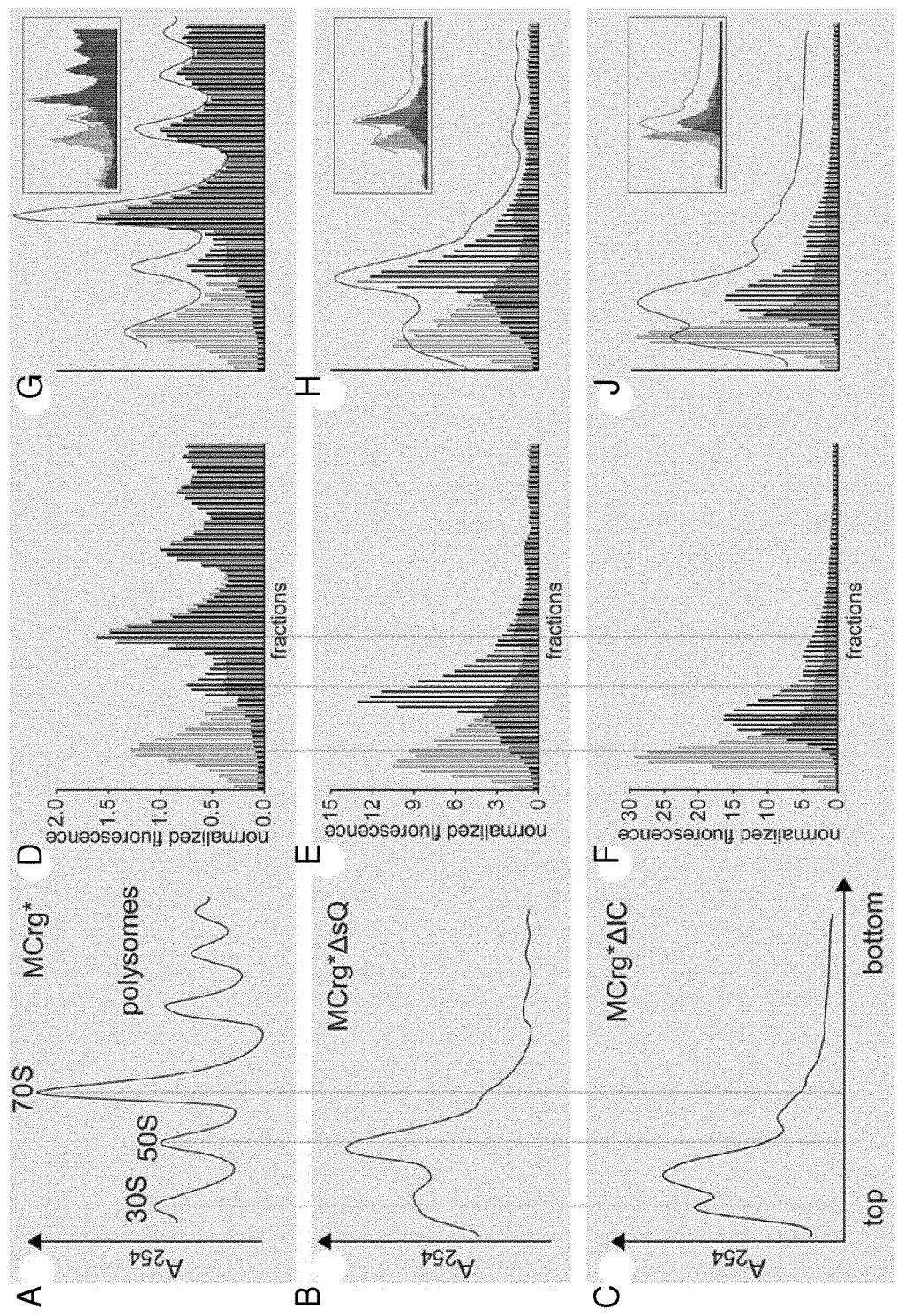
FIG. 13 shows cells, that were grown in M9 medium at 37° C. to OD600=0.4 and harvested. Lysates were subjected to sucrose gradient centrifugation. Centrifugates were analyzed by A254 detection and fractionated. Polysome profiles derived from: (A) MCrg*, (B) MCrg*ΔsQ, (C) MCrg*ΔIC. Sucrose gradient fractions of samples A-F were analyzed for mAzami- and mCherry specific fluorescence and normalized results are given in bar charts for: (D) MCrg*(E) MCrg*□sQ (F) MCrg*ΔIC. Superposition of A254 profiles and corresponding fluorescence bar charts: (G) MCrg*, (H) MCrg*ΔsQ, (J) MCrg*ΔIC. The inserts show fluorescence analysis of all available fractions from each sucrose gradient run. Bars with black lines: normalized mCherry fluorescence; Black bars: normalized mAzami fluorescence. Fluorescence was normalized to the first polysome peak ("disome") where subunits are supposed to be present in 1:1 ratio

II.2. Generation of Ribosome Subunit Specific Assembly Defects and In Vitro Analysis To generate assembly defects of either the small or the large ribosomal subunit, conditional gene knock outs of rpsQ (encoding S17) and rplC (encoding L3), respectively, were generated in the reporter strain background. The resulting strains (MCrg*ΔsQ and MCrg*ΔlC) carried plasmids containing wild type copies of the genes deleted from the chromosome under control of an IPTG inducible promoter. The withdrawal of IPTG in liquid cultures should result in impaired growth and in subunit specific assembly defects as soon as the number of intact ribosomes becomes limiting. MCrg*, MCrg*ΔsQ (RN116) and -ΔlC (RN117) cells were grown in the absence of IPTG to mid-logarithmic phase and the ribosomes examined by sucrose gradient ultracentrifugation and polysome profile analysis (FIGS. 13A-C). MCrg* ribosomes showed the expected pattern consisting of 30S-, 50S-, 70S-, and polysome peaks (FIG. 13A), whereas depletion of rpsQ (FIG. 13B) led to reduced amounts of 70S ribosomes and polysomes and increased the 50S compared to the 30S peak. Likewise, depletion of rplC reduced the amount of 70S ribosomes and led to increased amounts of solitary large and small subunits (FIG. 13C). This was consistent because the absence of rpsQ and rplC, respectively, should result in defective small and large ribosomal subunits. Consequently, the reduced number of functional subunits limited the amount of monosomes and polysomes. Fluorometric analysis of the sucrose fractions provided fluorescence profiles of MCrg*, MCrg*ΔsQ and -ΔlC derived ribosomes (FIGS. 13D-F). Comparing A254 and fluorescence profiles of MCrg* ribosomes by overlay (FIG. 13G) revealed a reasonable coincidence of the individual peaks. When considering the entire profile, including early low molecular weight fractions (FIG. 13G insert), high fluorescence signals at the left side of the diagram reflect natural early-assembly intermediates of ribosomal subunits. When analyzing A254 and fluorescence profiles of MCrg*ΔsQ ribosomes by overlay (FIG. 13H) several aspects attracted attention: The red fluorescence peak—representing the small subunit—was decreased in intensity (compared with FIG. 13G) and in addition left shifted due to absence of rpsQ. The green fluorescence peak—representing the large subunit—was eventually slightly left shifted and showed a shoulder at the left side overlapping with the red peak, indicating defective large ribosomal subunits. This was first evidence that a selective assembly defect of the small subunit is associated with a defect in the large subunit. Finally, the insert showed that there was no increased fluorescence in the low molecular weight fractions, indicating proper autogenous control of S15-mCherry and L1-mAzami. Combined analysis of A254 and fluorescence profiles of MCrg*ΔlC ribosomes (FIG. 13J) revealed a decrease in the green fluorescence peak, which was in addition clearly left shifted, due to assembly defects in the absence of rplC. In the A254 profile the peak of the large subunit appeared higher than the peak of the small subunit. This is presumably the case because peaks of both subunits are overlapping each other (FIG. 13F) thereby producing an apparently dominant peak of the large subunit. Investigation of the low molecular weight fractions in the insert showed strict feedback regulation of S15-mCherry and L1-mAzami. In summary, assembly defects of the small and large ribosomal subunit could be provoked and were readily detectable by fluorescence analysis of sucrose gradient centrifugates.

II.2 In Vivo Analysis of Subunit Specific Assembly Defects

Figure 14:
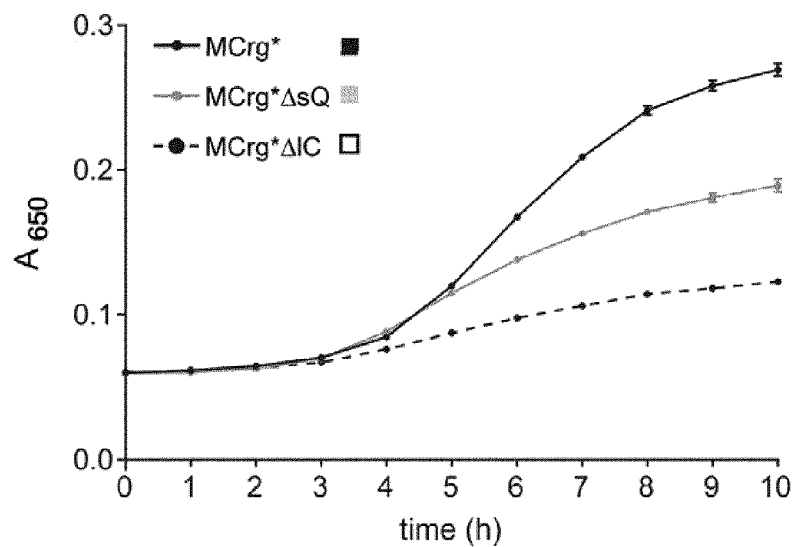
FIG. 14 shows growth in 384-well pates and fully automated fluorescence analysis of reporter strains. Aliquots of MCrg*, MCrg*ΔsQ and MCrg*ΔIC cultures were transferred into 384-well plates in quadruplicates. Cells were grown in M9 medium at 37° C. for 10 hours. Measurements were made in one-hour intervals. (A) $A_{650}$ values were determined and (B) mAzami and mCherry fluorescence emission were detected and ratios were calculated for MCrg*, MCrg*ΔsQ and MCrg*ΔIC. Fluorescence ratios of MCrg* were normalized to 1. Data points given in the growth curves and fluorescence ratios are mean values; n=4, error bars show s.d.
Figure 14:
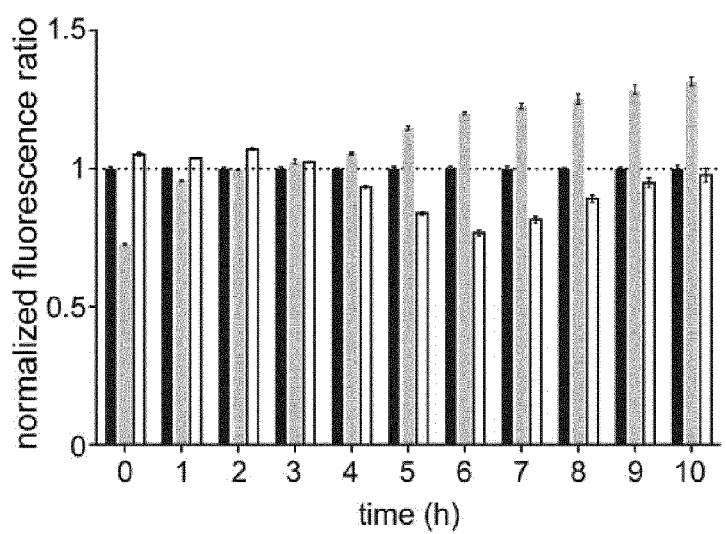

Further on, it was investigated whether subunit assembly defects are detectable by fluorescence readout in vivo using MCrg*. Fluorescent labeling of the early assembly r-proteins L1 and S15 results in fluorescent subunits of all stages of maturation. Since both subunits are systemically produced in equal amounts any shift in the fluorescence ratios is supposed to be a consequence of subunit specific degradation. An assembly defect of the large subunit should reduce the amount of green fluorescence and consequently lower the normalized fluorescence emission ratio of mAzami/mCherry, while an assembly defect of the small subunit in turn should increase the ratio. MCrg*, MCrg*ΔsQ and MCrg*ΔlC cells were transferred to 384-well plates and incubated at 37° C. for 10 hours in M9 medium. Fully automated sample handling was possible, using a robotic platform equipped with incubator, micro plate reader and robotic arm. Both $A_{650}$ values and fluorescence intensities were measured (FIG. 14) in one-hour intervals. From the latter normalized fluorescence ratios were calculated. While MCrg* grew unperturbed, MCrg*ΔsQ and MCrg*ΔlC cells showed impaired growth and reached lower cell densities after 10 hours (FIG. 14A). The background corrected and normalized fluorescence ratios of MCrgΔlC reached a minimum of 0.8 after 6 hours, whereas the ratios of MCrgΔsQ increased instead reaching a maximum of 1.3 after 9 hours (FIG. 14B). This shows that even though depletion of rplC and rpsQ, respectively, caused severe assembly defects of ribosomal subunits, ratios did not change drastically due to accumulation of defective assembly intermediates.

II.3 Probing MCrg* with Ribosome-targeting Antibiotics

Figure 15:
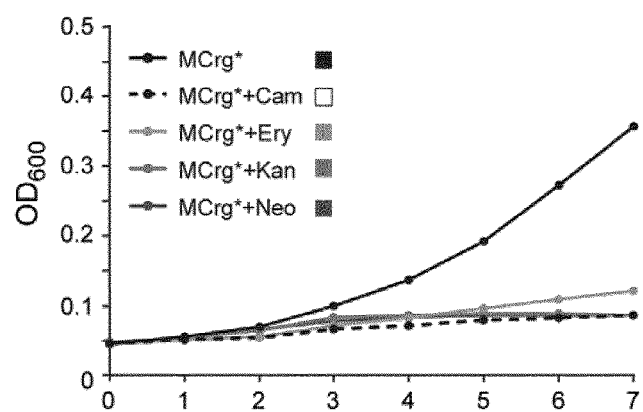
FIG. 15 shows results of MCrg* upon treatment with inhibitors of translation. Whole-cell analyses (A-B): MCrg* cells were cultured in at 25° C. in M9 medium for 7 hours in the absence and presence of antibiotics, as indicated. Samples were taken every hour. (A) $OD_{600}$ values were determined and (B) mAzami and mCherry fluorescence emission were detected and ratios were calculated. Fluorescence ratios of MCrg* were normalized to 1. Exemplary growth curves are given and fluorescence ratios are means from three independent experiments; error bars show s.d. Analyses of isolated ribosomal particles (C-H and J-M): Sucrose density gradient (10-25%) centrifugation profiles from (C) control cells with no antibiotic (none), (D) chloramphenicol (Cam), (E) erythromycin (Ery), (F) kanamycin (Kan) and (G) neomycin (Neo) treated cells. Sucrose gradient fractions from (C) to (G) were analyzed for fluorescence by a micro plate reader. $A_{254}$ profiles and fluorescence bar charts were superimposed for (H) control cells with no antibiotic (none), (J) chloramphenicol (Cam), (K) erythromycin (Ery), (L) kanamycin (kan) and (M) neomycin (Neo) treated cells. Cells in presence and absence of antibiotics were cultured in LB medium at 25° C. for 3 hours before subsequent polysome analysis. Left shifted peaks of the large subunit are indicated by horizontal arrows, abnormal portions of the small subunit by vertical arrows; Bars with black lines: normalized mCherry fluorescence; Black bars: normalized mAzami fluorescence. Fluorescence was normalized to the first polysome peak ("disome") where subunits are present in 1:1 ratio.
Figure 15:
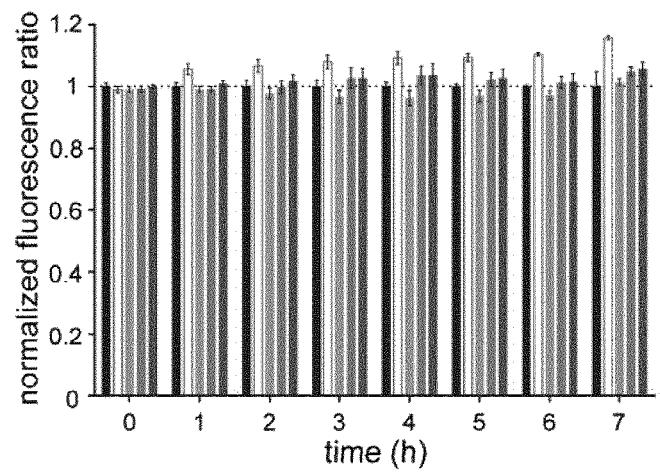
Figure 15:
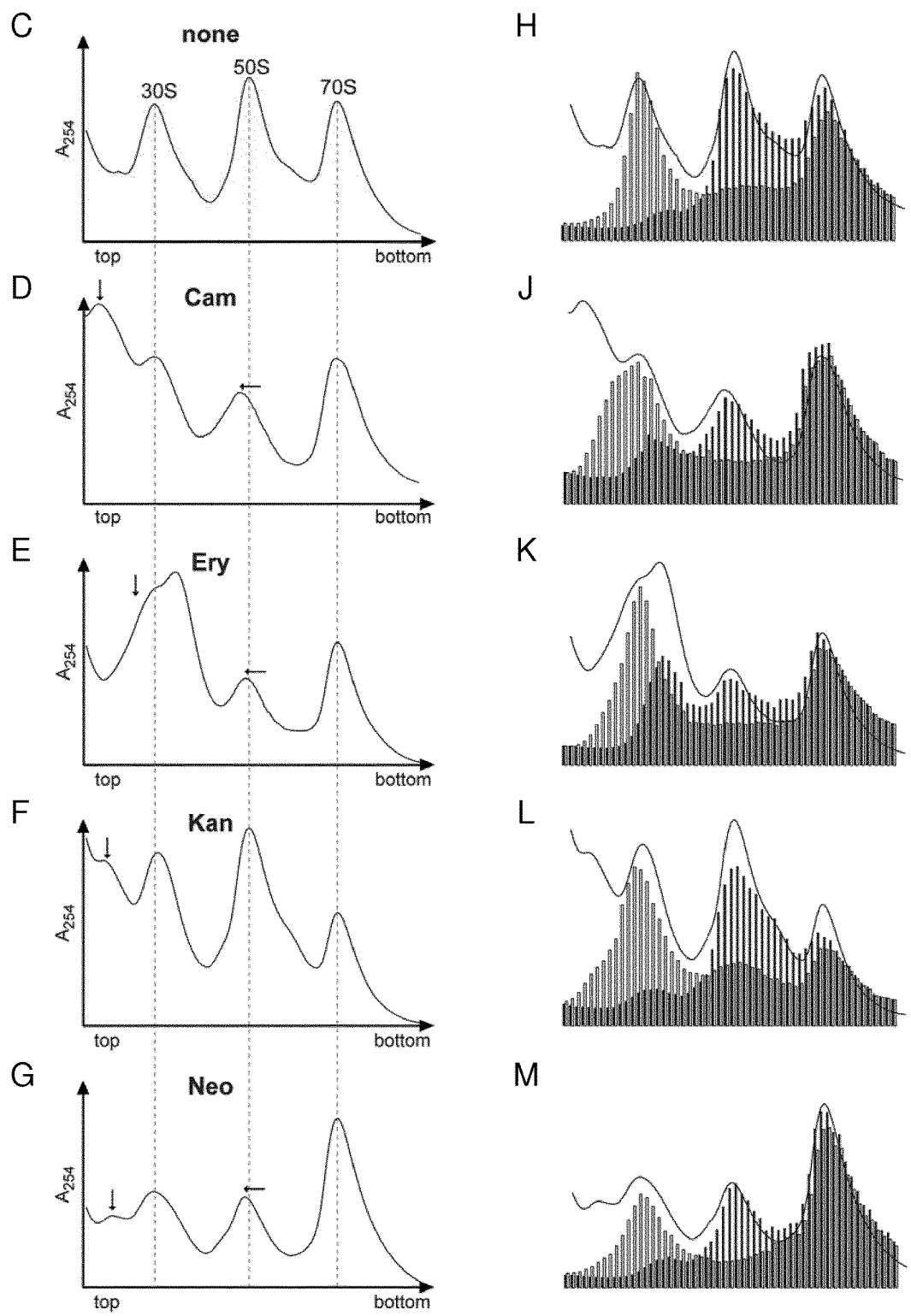

Using MCrg*, it was investigated, whether treatment of cells with ribosome targeting antibiotics results in assembly defects of both ribosomal subunits. The antibiotics tested were chloramphenicol, erythromycin and neomycin, which are known to cause assembly defects of both ribosomal subunits, and kanamycin, which was so far not investigated for its potential to cause ribosome assembly defects. MCrg* cells were cultured in M9 medium for seven hours in the absence or presence of chloramphenicol (7 μg/ml), erythromycin (100 μg/ml), kanamycin (7 μg/ml) or neomycin (7 μg/ml). While treatment with all of them led to impaired cell growth (FIG. 15A), chloramphenicol caused the strongest growth defects. Fluorometric analysis revealed that the normalized fluorescence ratio in the presence of erythromycin decreased continuously reaching 0.95 after 5 hours. Both kanamycin and neomycin treated did not show a significant change in the fluorescence ratio at all (FIG. 15B). Treatment with chloramphenicol, by contrast, led to an increased fluorescence ratio, with a maximum of 1.20 after 7 hours. This suggests that treatment of cells with the antibiotic erythromycin led to a relative reduction in the amount of the large subunit, while treatment with chloramphenicol decreased the relative amounts of the small subunit. This hypothesis was tested by analyzing ribosome profiles obtained from MCrg* cells that grew in the presence of the antibiotics or without (FIG. 15C-G). FIG. 15C shows the $A_{254}$ profile of ribosomes derived from non treated cells. The 70S peak and the polysomes (not shown) are reduced in intensity since no chloramphenicol was added prior to harvesting to prevent 70S run off. Ribosomes derived from chloramphenicol (FIG. 15D) or erythromycin (FIG. 15E) treated cells showed reduced and left shifted 50S peaks. Chloramphenicol treatment caused an additional peak (left-lateral of 30S), while after erythromycin treatment the 30S peak had a shoulder on the left. Treatment with kanamycin had no apparent influence on the 50S peak but provoked an additional peak left-lateral of the 30S peak (FIG. 15F). Neomycin treatment caused a slight reduction and left shift of the 50S peak and an additional peak on the left of the 30S peak.

When focusing on the overlay diagrams (combining A254 and fluorescence read outs) (FIG. 15H, J-M), ribosome profiles from non treated cells are basically congruent (FIG. 15H). Profiles from chloramphenicol and in particular erythromycin treated cells reveal a portion of green fluorescence within the region of the 30S peak (FIG. 15J-K). Ribosome profiles derived from kanamycin and neomycin treated cells possess green fluorescent peaks of weaker intensity but at similar positions within the profile (FIG. 15L-M). These peaks of green fluorescence presumably represent defective assembly intermediates of the large subunit that are caused by all the antibiotics used in this study, but to different extend. Comparison of the red fluorescent peaks (FIG. 15H, J-M) indicates that treatment with all antibiotics produced a more or less pronounced shoulder on the left. To analyze eventual defects of the small subunit in more detail, the red fluorescence profiles were aligned and the one derived from non treated cells was compared with all the others obtained from antibiotic treated cells. This revealed that treatment with all four antibiotics caused distinct left-sided shoulders of the red fluorescence peak, indicating small subunit assembly defects. A more thorough analysis including quantitation of the 16S and 23S rRNA within the sucrose fractions confirmed the presence of assembly intermediates.

In summary, the in vivo studies demonstrated that ribosome assembly defects were detectable in great detail when analyzing fractions of sucrose ultracentrifugates fluorometrically. Assembly defects caused by gene depletions (rplC and rpsQ) or by treatment of reporter cells with four different ribosome-targeting antibiotics revealed the presence of differing defective assembly intermediates of both ribosomal subunits.

III. *E. coli* Expressing Fusion Proteins of Two Different Ribosomal Proteins of the Same Ribosomal Subunit To investigate in more detail the effects of compounds such as antibiotics on ribosomal subunit assembly, further reporter strains (MCrgL/RN120.1 and MCrgS/RN121.1) were developed. These strains specifically allow the quantification of subunit assembly defects. MCrgL expresses one early (RPL1) and one late (RPL19) assembling ribosomal protein of the large subunit labelled by mCherry and mAzami, respectively. Likewise, MCrgS expresses one early (RPS15) and one late (RPS2) assembling ribosomal protein of the small subunit labelled by mCherry and mAzami, respectively. To analyze potential differences in growth more precisely, wild type and reporter strains were grown to stationary phase at different temperatures and growth rates were calculated. This revealed that the growth rate of MCrgL and MCrgS were within the range of the wild type strain at 37° C. as well as 42° C. Additionally, cells were grown in M9 medium at 37° C. to $OD_{600}$=0.4 and cell lysates subjected to sucrose gradient centrifugation. The centrifugates were analyzed by $A_{254}$ detection and fractionated. Results are shown in FIG. 16.

IV. Methods

IV.6.1 Lambda-Red Recombineering and Knock-Out/-In Generation

To facilitate the stable integration of linear DNA into the genome via homologous recombination, the *E. coli* strain DY330 was employed as host strain. The DNA sequences for genomical integration were created by PCR amplification of the constructs with primers containing overhangs of approximately 50 bp in length homologous to the upstream and downstream loci of the target gene on the bacterial chromosome. In this way, Knock-Outs of the genes rpsT, rpsQ, rplC and rplS were created by introducing a PCR amplified kanamycin resistance cassette in place of the original gene. All fluorescent protein tagged versions of ribosomal proteins were created in the same manner. The following vectors were used for transgene generation: pRN14 (link-EGFP) (SEQ ID NO.: 17), pRN14 (link-mCherry) (SEQ ID NO.: 18), pRN14 (link-mAzami green) (SEQ ID NO.: 19), pRN14 (link-ECFP(A206K)) (SEQ ID NO.: 20), pRN14 (link-EYFP(A206K)) (SEQ ID NO.: 21), pMRBAD-Tev-mCherry (SEQ ID NO.: 22), and pRN14 (Tev-EYFP(A206K)) (SEQ ID NO.: 23). *E. coli* DY330 cells were cultured at 30° C. and 190 rpm in a water shaker until an OD600 of 0.6-0.8 was reached and then shifted to 42° C. for 15 minutes to induce the temperature dependent expression of the homologous recombination facilitating lambda prophage genes. A non-induced control was detained as additional control. Cells were transformed using electroporation.

VI.6.2 Polysome Profiles and Subunit Separation

*E. coli* cells were inoculated from stationary cultures and incubated until mid-logarithmic phase (OD600=0.6-0.8). In order to record polysome profiles, cells were sedimented, resuspended and lysed. After centrifugation, lysates of 10 A260 units were loaded onto 5-45% sucrose gradients for polysome profiles or 10-40% gradients for subunit separation. Ultracentrifugation was performed at 41.000 rpm (3 h; polysome profiles) or 23.000 rpm (16 h, subunit separation). Ribosomal components in the gradients were analyzed by recording the A254 values and collecting 200 μl and 50 μl fractions, respectively, that were later examined in 96-well plates on fluorescence by using a plate reader.

IV.6.3 Fluorescence Time Courses in Multi-Well Plates

Cells grown to stationary phase were diluted to an OD600 of 0.05 and transferred into 96-well plates, such that each well contained an initial volume of 100 μl. In the case of 384-well plates, 50 μl of cells were transferred in each well from trays harboring 50 ml of cell suspension. Non-fluorescent wild-type strain MC4100 was used to obtain background values for later subtraction. Cells were further incubated in the plate reader for several hours and fluorescence as well as A650 data were collected every 10 minutes. Mean values were calculated and MC4100 fluorescence background values were subtracted from the reporter strain values.

Device and measurement parameters were as follows:

| Parameter | Value |
| --- | --- |
| Absorbance | 650 nm; 10 reads; 5 ms settle time |
| Amount of pre-cycles | 7 |
| Amount of cycles | 61 |
| EGFP Fluorescence | Exc.: 485 +/− 20 nm |
|  | Em.: 535 +/− 25 nm |
|  | Manual gain = 40; 10 flashes |
| mCherry Fluorescence | Exc.: 535 +/− 25 nm |
|  | Em.: 612 +/− 10 nm |
|  | Manual gain = 40; 10 flashes |
| Temperature | 30° C. |
| Shaking parameters | Before each measurement |
|  | 3 s, linear mode, 2 mm amplitude |
| Time between two measurements | 10 minutes |

IV.6.4 FRET Analysis

Cells were grown in LB at 37° C. and subsequently seeded in poly-L-lysine coated wells of 96-well plates. Fluorescence of FRET pairs, e.g ECFP and EYFP specific fluorescence was detected before and after acceptor photobleaching (APB). When FRET occurs, the donor fluorescence (ECFP) was increased upon bleaching of the acceptor (EYFP). As control, reporter cells were treated with Rifampicin, a specific inhibitor of RNA polymerase. After Rifampicin treatment no more mRNAs were produced, existing ones underwent natural turnover and after about ten minutes the level of mRNAs was massively decreased. Accordingly, Rifampicin treatment reduced FRET.

REFERENCES

Datsenko K A, Wanner B L.; Proc Natl Acad Sci USA. 2000 Jun. 6; 97(12):6640-5.; One-step inactivation of chromosomal genes in *Escherichia coli* K-12 using PCR products.

Jiang M, Sullivan S M, Walker A K, Strahler J R, Andrews P C, Maddock J R.; J Bacteriol. 2007 May; 189(9):3434-44. Epub 2007 Mar. 2.; Identification of novel *Escherichia coli* ribosome-associated proteins using isobaric tags and multidimensional protein identification techniques.

Shajani Z, Sykes M T, Williamson J R.; Annu Rev Biochem. 2011 Jun. 7; 80:501-26. doi: 10.1146/annurev-biochem-062608-160432.; Assembly of bacterial ribosomes.

Stöter M, Niederlein A, Barsacchi R, Meyenhofer F, Brandi H, Bickle M.; Methods Mol Biol. 2013; 986:105-22. doi: 10.1007/978-1-62703-311-4_8.; CellProfiler and KNIME: open source tools for high content screening.

The invention claimed is:

1. A prokaryotic cell expressing
  a first fusion protein comprising a first ribosomal protein, an amino acid linker and a first fluorescent protein, and
  a second fusion protein comprising a second ribosomal protein, an amino acid linker and a second fluorescent protein,
  wherein the first fluorescent protein and the second fluorescent protein are different and clearly distinguishable,
  wherein the first fusion protein is expressed from the endogenous gene locus of the first ribosomal protein and the second fusion protein is expressed from the endogenous gene locus of the second ribosomal protein.

2. The cell of claim 1, wherein the first ribosomal protein and the second ribosomal protein are different ribosomal proteins of a small ribosomal subunit or different ribosomal proteins of a large ribosomal subunit.

3. The cell of claim 1, wherein the first ribosomal protein is a protein of a small ribosomal subunit and the second ribosomal protein is a protein of a large ribosomal subunit.

4. The cell of claim 1, wherein the first fusion protein and the second fusion protein are located towards the surface of the assembled ribosome.

5. The cell of any claim 1, wherein the first and the second fluorescent protein are each selected from the group consisting of EBFP, ECFP, mTurquoise, mAzami-green, EGFP, sfGFP, Tag-GFP2, EYFP, Venus, mCherry, Tag-RFP and mKate2.

6. The cell of claim 1, wherein the cell is selected from the group consisting of *Escherichia coli, Salmonella spec, Bacillus subtilis, Thermus thermophilus, Staphylococcus aureus*, and *Streptococcus pneumoniae*.

7. The cell of claim 1, wherein the ribosomal protein is a small ribosomal subunit protein selected from the group consisting of RPS2, RPS3,RPS5, RPS6, RPS10, RPS15, RPS16, RPS17, RPS18 1, RPS19 and RPS20 and/or the ribosomal protein is as large ribosomal subunit protein selected from the group consisting of RPL1, RPL2, RPL3, RPL4, RPL5, RPL6, RPL9, RPL10, RPL11, RPL13, RPL14, RPL15, RPL16, RPL17, RPL18, RPL19, RPL20, RPL21, RPL22, RPL23, RPL24, RPL25, RPL27, RPL30, RPL31, RPL32, RPL33 and RPL34.

8. A method for identifying a compound which interferes with ribosome biogenesis, assembly and/or degradation, said method comprising:
   a) culturing the prokaryotic cell according to claim 1,
   b) measuring the fluorescence signal of the first and second fluorescent protein,
   c) adding the compound to the cell, and
   d) re-measuring the fluorescence signal of the first and second fluorescent protein,
   wherein a change in the fluorescence signal measured in step d) when compared to the fluorescence signal measure in step b) of the first and/or second fluorescent protein indicates that the compound interferes with ribosome biogenesis, assembly and/or degradation.

9. The method of claim 8, wherein steps b) and d) further comprise measuring cell density.

10. A method of screening a library of compounds to identify one or more members having antibiotic properties, said method comprising:
    a) culturing the prokaryotic cell according to claim 1,
    b) measuring the fluorescence signal of the first and second fluorescent protein,
    c) contacting the cell with at least one compound of the library, and
    d) re-measuring the fluorescence signal of the first and second fluorescent protein,
    wherein a change in the fluorescence signal measured in step d) when compared to the fluorescence signal measured in step b) of the first and/or second fluorescent protein indicates that the compound has antibiotic properties.

11. A method for monitoring ribosome biogenesis, assembly and/or degradation comprising
    a) culturing prokaryotic cells according to claim 1, and
    b) monitoring the fluorescence signal of the first and second fluorescent protein,
    wherein a change in the fluorescence signal observed in step b) indicates an alteration in ribosome biogenesis, assembly and/or degradation.

12. The method of claim 11, wherein the monitoring comprises harvesting and lysing the cells and measuring the fluorescence signal of the first and second fluorescent protein in the cell lysate.

13. The method of claim 11, wherein the monitoring comprises isolating the ribosomes and measuring the fluorescence signal of the first and second fluorescent protein in the isolated ribosomes.

14. A gene construct comprising a first element encoding a first ribosomal protein fused to a first fluorescent protein by an amino acid linker, and a second element encoding a second ribosomal protein fused to a second fluorescent protein by an amino acid linker.

15. A kit comprising
    (I) a prokaryotic cell expressing
        (i) a first fusion protein comprising a protein of a small ribosomal subunit, an amino acid linker and a first fluorescent protein from the endogenous gene locus of the protein of the small ribosomal subunit, and
        (ii) a second fusion protein comprising a protein of a large ribosomal subunit, an amino acid linker and a second fluorescent protein from the endogenous gene locus of the protein of the large ribosomal subunit, and
    (II) a prokaryotic cell expressing
        (i) a fusion protein comprising a first ribosomal protein, an amino acid linker and a first fluorescent protein from the endogenous gene locus of the first ribosomal protein and
        (ii) a second fusion protein comprising a second ribosomal protein, an amino acid linker and a second fluorescent protein from the endogenous gene locus of the second ribosomal protein,
    wherein the first ribosomal protein and the second ribosomal protein are different ribosomal proteins of the small or large ribosomal subunit.

* * * * *

UNITED STATES PATENT AND TRADEMARK OFFICE
CERTIFICATE OF CORRECTION

PATENT NO. : 9,708,602 B2
APPLICATION NO. : 14/894262
DATED : July 18, 2017
INVENTOR(S) : Rainer Nikolay and Elke Deuerling Page 1 of 1

It is certified that error appears in the above-identified patent and that said Letters Patent is hereby corrected as shown below:

In the Claims

Column 83, Line 23, Claim 7, please delete "RPS17, RPS18 1, RPS19" and insert -- RPS17, RPS18, RPS19 -- therefor.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*